United States Patent [19]

Sugimoto et al.

[11] Patent Number: 4,895,841
[45] Date of Patent: Jan. 23, 1990

[54] CYCLIC AMINE COMPOUNDS WITH ACTIVITY AGAINST ACETYLCHOLINESTERASE

[75] Inventors: Hachiro Sugimoto, Ushiku, Japan; Yutaka Tsuchiya, Fort Lee, N.J.; Kunizou Higurashi, Tokyo, Japan; Norio Karibe, Tsukuba, Japan; Youichi Iimura, Tsukuba, Japan; Atsushi Sasaki, Tsukuba, Japan; Yoshiharu Yamanishi, Ryugasaki, Japan; Hiroo Ogura, Tsuchiura, Japan; Shin Araki, Tsukuba, Japan; Takashi Kosasa, Tsukuba, Japan; Atsuhiko Kubota, Tsukuba, Japan; Michiko Kosasa, Tsukuba, Japan; Kiyomi Yamatsu, Kamakura, Japan

[73] Assignee: Eisai Co., Ltd., Tokyo, Japan

[21] Appl. No.: 209,339

[22] Filed: Jun. 20, 1988

[30] Foreign Application Priority Data

Jun. 22, 1987 [JP] Japan ................................. 62-155058

[51] Int. Cl.$^4$ ..................... A61K 31/55; C07D 405/06
[52] U.S. Cl. .................................... 514/212; 514/319; 514/321; 514/408; 514/422; 514/429; 540/484; 540/596; 540/611; 540/612; 546/197; 546/206; 548/400; 548/526; 548/578

[58] Field of Search ................ 546/206, 197; 548/578, 548/400, 526; 540/484, 596, 611, 612; 514/212, 429, 319, 321, 408, 422

[56] References Cited

U.S. PATENT DOCUMENTS 3,476,759 11/1969 Paragamian ........................ 546/206

Primary Examiner—Richard A. Schwartz
Attorney, Agent, or Firm—Flynn, Thiel, Boutell & Tanis

[57] ABSTRACT

A cyclic amine compound is defined by the formula:

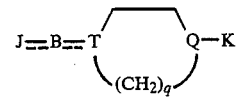

in which J is indanyl, indanonyl, indenyl, indenonyl, indanedionyl, tetralonyl, benzosuberonyl, indanolyl or a divalent group thereof, K is phenyl, an arylalkyl or cynnamyl, B is —(CHR22)r—, R22 being H or methyl, —CO—(CHR22)r—, =(CH—CH=CH)b—, =CH—(CH2)c— or =(CH—CH)d= and the ring including T and Q is piperidine. The compound is useful to treat senile dementia.

13 Claims, No Drawings

CYCLIC AMINE COMPOUNDS WITH ACTIVITY AGAINST ACETYLCHOLINESTERASE

The invention relates to a cyclic amine compound, a therapeutical composition and medical treatment of senile dementia.

Statement of Prior Arts

With a rapid increase in the population of aged people, the establishment of the therapy for senile dementia, such as Alzheimer senile dementia, is eagerly desired.

Various attempts have been made to treat the senile dementia with a drug. So far, however, there has been no drug which is very useful for the treatment of these diseases.

Studies on the development of therapeutic agents for these diseases have been made from various aspects. Particularly, since Alzheimer senile dementia is accompanied by the lowering in cholinergic hypofunction, the development of the therapeutic agent from the aspect of an acetylcholine precursor and an acetylcholinesterase inhibitor was proposed and has in fact been attempted. Representative examples of the anticholinesterase inhibitors include physostigmine and tetrahydroaminoacridine. However, these drugs have drawbacks such as an unsatisfactory effect and the occurrence of unfavorable side effects. At the present time, there are no decisive therapeutic agents.

In view of the above situation, the present inventors have made extensive and intensive studies on various compounds for many years with a view to developing a drug which has a persistent activity and a high safety.

As a result, the present inventors have found that a piperidine derivative represented by the following general formula (I) can attain the desired object.

Specifically, the compound of the present invention represented by the following general formula (I) has great advantages of having strong and highly selective antiacetylcholinesterase activity, increasing the amount of acetylcholine present in the brain, exhibiting an excellent effect on a model with respect to disturbance of memory, and having a persistent activity and a high safety when compared with physostigmine which is a conventional popular drug in the art, which renders the compound of the present invention very valuable.

The compound of the present invention was found based on the acetylcholinesterase inhibitory action and, therefore, is effective for treatment and prevention of various diseases which are thought to be derived from the deficiency of acetylcholine as a neurotransmitter in vivo.

Examples of such diseases include various kinds of dementia including Alzheimer senile dementia and further include Huntington's chorea, Pick's disease, and ataxia.

Therefore, the objects of the present invention are to provide a novel piperidine derivative effective as a pharmaceutical, particularly for treatment and prevention of central nervous system disease, to provide a process for preparing the same, and to provide a pharmaceutical comprising the same as an effective ingredient.

Summary of the Invention

The invention provides a cyclic amine compound having the following formula (XXV) and a pharmacologically acceptable salt thereof:

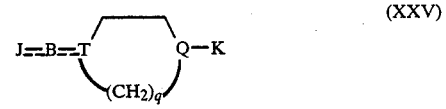

in which J is (a) a group, substituted or unsubstituted, selected from the group consisting of (1) phenyl, (2) pyridyl, (3) pyrazyl, (4) quinolyl, (5) cyclohexyl, (6) quinoxalyl and (7) furyl;

(b) a monovalent or divalent group, in which the phenyl may have a substituent(s), selected from the group consisting of (1) indanyl, (2) indanonyl, (3) indenyl, (4) indenonyl, (5) indanedionyl, (6) tetralonyl, (7) benzosuberonyl, (8) indanolyl and (9) $C_6H_5$—CO—CH($CH_3$)—;

(c) a monovalent group derived from a cyclic amide compound;

(d) a lower alkyl or (e) a group of $R^{21}$—CH=CH— in which $R^{21}$ is hydrogen or a lower alkoxycarbonyl;

B is —(CHR$^{22}$)$_r$—, —CO—(CHR$^{22}$)$_r$—, —NR$^4$—(CHR$^{22}$)$_r$—, $R^4$ being hydrogen, a lower alkyl, an acyl, a lower alkylsulfonyl, phenyl, a substituted phenyl, benzyl or a substituted benzyl, —CO—NR$^5$—(CHR$^{22}$)$_r$—, $R^5$ being hydrogen, a lower alkyl or phenyl, —CH=CH—(CHR$^{22}$)$_r$—, —OCOO—(CHR$^{22}$)$_r$—, —OOC—NH—(CHR$^{22}$)$_r$—, —NH—CO—(CHR$^{22}$)$_r$—, —CH$_2$—CO—NH—(CHR$^{22}$)$_r$—, —(CH$_2$)$_2$—NH—(CHR$^{22}$)$_r$—, —CH(OH)—(CHR$^{22}$)$_r$—, r being zero or an integer of 1 to 10, R22 being hydrogen or methyl so that one alkylene group may have no methyl branch or one or more methyl branch, =(CH—CH=CH)$_b$—, b being an integer of 1 to 3, =CH—(CH$_2$)$_c$—, c being zero or an integer of 1 to 9, =(CH—CH)$_d$=, d being zero or an integer of 1 to 5; —CO—CH=CH—CH$_2$—, —CO—CH$_2$—CH(OH)—CH$_2$—, —CH(CH$_3$)—CO—NH—CH$_2$—, —CH=CH—CO—NH—(CH$_2$)$_2$—, —NH—, —O—, —S—, a dialkylaminoalkylcarbonyl or a lower alkoxycarbonyl;

T is a nitrogen or carbon;

Q is nitrogen, carbon or

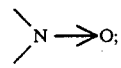

and q is an integer of 1 to 3;

K is hydrogen, phenyl, a substituted phenyl, an arylalkyl in which the phenyl may have a substituent, cinnamyl, a lower alkyl, pyridylmethyl, a cycloalkylalkyl, adamantanemethyl, furylmenthyl, a cycloalkyl, a lower alkoxycarbonyl or an acyl; and shows a single bond or a double bond.

In the compounds having the formula (XXV), it is preferable that J is (a) or (b). In the definition (b), monovalent groups of (2), (3) and (5) and divalent groups of (2) are preferable. In the definition of B, —(CHR22)r—, =(CH—CH=CH)b—, =CH—(CH2)c— and =(CH—CH)d= are preferable. These preferable groups of (B) may be connected with (b) of J, in particular (2) of (b).

It is preferable in the formula (XXV) that Q is nitrogen, T is carbon and q is 1 or 3; and Q is carbon, T is nitrogen and q is 2. It is most preferable that Q is nitrogen, T is carbon and q is 2.

It is preferable that K is a phenylalkyl or a phenylalkyl having a substituent(s) on the phenyl.

Preferable compounds of the invention include:
1-benzyl-4-((5,6-dimethoxy-1-indanon)-2-yl)methylpiperidine,
1-benzyl-4-((5,6-dimethoxy-1-indanon)-2-ylidenyl)methylpiperidine,
1-benzyl-4-((5-methoxy-1-indanon)-2-yl)methylpiperidine,
1-benzyl-4-((5,6-diethoxy-1-indanon)-2-yl)methylpiperidine,
1-benzyl-4-((5,6-methnylenedioxy-1-indanon)-2-yl)methylpiperidine,
1-(m-nitrobenzyl)-4-((5,6-dimethoxy-1-indanon)-2-yl)methylpiperidine,
1-cyclohexymethyl-4-((5,6-dimethoxy-1-indanon)-2-yl)methylpiperidine,
1-(m-florobenzyl)-4-((5,6-dimethoxy-1-indanon)-2-yl)methylpiperidine,
1-benzyl-4-((5,6-dimethoxy-1-indanon)-2-yl)propylpiperidine,
1-benzyl-4-((5-isopropoxy-6-methoxy-1-indanon)-2-yl)methylpiperidine and
1-benzyl-4-((5,6-dimethoxy-1-oxoindanon)-2-yl)propenylpiperidine, having the below shown formula, shown in Example 224.

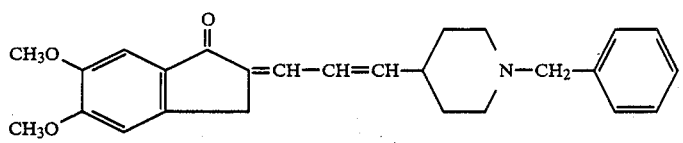

In addition, the invention provides a therapeutical composition which comprises a pharmacologically effective amount of the cyclic amine compound having the formula (XXV) or a pharmacologically acceptable salt thereof and a pharmacologically acceptable carrier and then a method for preventing and treating a disease due to the acetylcholinesterase activity by administering to a human patient the cyclic amine compound having the formula (XXV) or a pharmacologically acceptable salt thereof.

The preferable compound has the above shown formula in which J is (b). The group (b) includes ten groups having the respective formulae shown below. S is hydrogen or a substituent such as a lower alkyl having 1 to 6 carbon atoms and a lower alkoxy having 1 to 6 carbon atoms. Among the substituents, methoxy is most preferable. t is an integer of 1 to 4. The phenyl is most preferred to have 1 to 3 methoxy groups thereon. $(S)_t$ may form methylene dioxy group or ethylene dioxy group on two adjacent carbon atoms of the phenyl group.

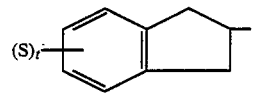

indanyl

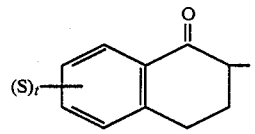

tetralonyl

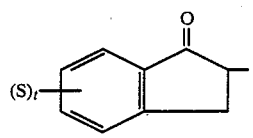

indanonyl

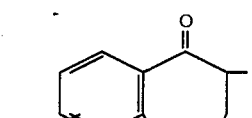

benzosuberonyl

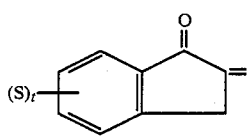

indanonylidenyl

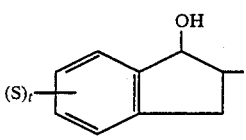

indanolyl

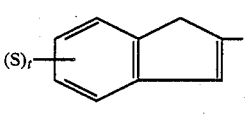

indenyl

-continued

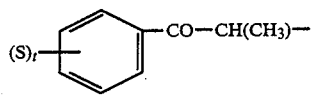

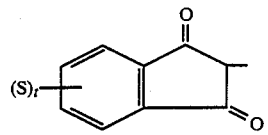

indanedionyl

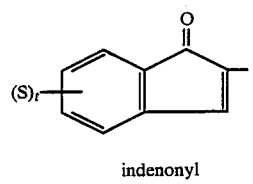

indenonyl

A preferable definition of B includes —$(CHR^{22})_r$—, —CO—$(CHR^{22})_r$—, =(CH—CH=CH)$_b$—, =CH—$(CH_2)_c$— and =(CH—CH)$_d$=. The group of —$(CHR^{22})_r$— in which $R^{22}$ is hydrogen and r is an integer of 1 to 3 and then the group of =CH—$(CH_2)_c$— are most preferable.

In the above defined cyclic amine compound of the invention, it is preferable that J in the formula is (b) the monovalent or divalent group. In the definition (b), indanonyl, indanedionyl and indenyl are most preferable, optionally having a substituent(s) on the phenyl.

In the definition B, —$(CHR^{22})_r$— and =CH—$(CH_2)_c$— are preferable.

In the ring including T and Q, it may be a 5-, 6- or 7-membered ring. It is preferable that Q is nitrogen, T is carbon or nitrogen and n is 2; Q is nitrogen, T is carbon and n is 1 or 3; and Q is carbon, T is nitrogen and n is 2.

In the definition K, phenyl, an arylalkyl and cinnamyl are preferable, optionally having a substituent(s) on the phenyl.

The invention will be explained in detail in view of the piperidine compounds which fall within the scope of the above defined cyclic amine compound. The explanation applies to the entire invention of the cyclic amine compound.

The piperidine compound is defined by the formula (I):

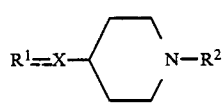

(I)

wherein $R^1$ is the following substituted or unsubstituted group: ① a phenyl group, ② a pyridyl group, ③ a pyrazyl group, ④ a quinolyl group, ⑤ an indanyl group, ⑥ a cyclohexyl group, ⑦ a quinoxalyl group, or ⑧ a furyl group; a monovalent or divalent group derived from an indanone having an unsubstituted or substituted phenyl ring; a monovalent group derived from a cyclic amide compound; a lower alkyl group or a group represented by the formula $R^3$—CH=C—

(wherein $R^3$ is a hydrogen atom or a lower alkoxycarbonyl group),

X is a group represented by the formula —$(CH_2)_n$—, a group represented by the formula

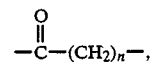

a group represented by the formula

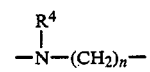

(wherein $R^4$ is a hydrogen atom, a lower alkyl group, an acyl group, a lower alkylsulfonyl group, or a substituted or unsubstituted phenyl or benzyl group), a group represented by the formula

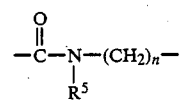

(wherein $R^5$ is a hydrogen atom, a lower alkyl group, or a phenyl group), a group represented by the formula —CH=CH—$(CH_2)_n$—, a group represented by the formula

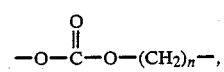

a group represented by the formula

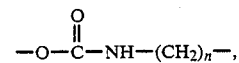

a group represented by the formula

—CH=CH—CH=CO—, a group represented by the formula

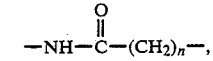

a group represented by the formula

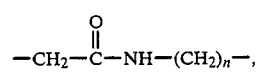

a group represented by the formula

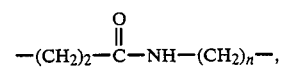

a group represented by the formula

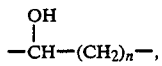

a group represented by the formula

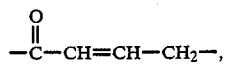

a group represented by the formula

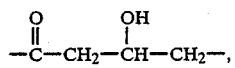

a group represented by the formula

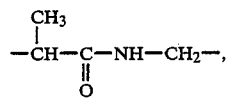

a group represented by the formula

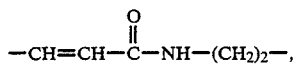

a dialkylaminoalkylcarbonyl group, or a lower alkoxycarbonyl group, provided that n's in the above definition of X are each independently an integer of 0 to 6, $R^2$ is a substituted or unsubstituted phenyl group, a substituted or unsubstituted arylalkyl group, a cinnamyl group, a lower alkyl group, a pyridylmethyl group, a cycloalkylalkyl group, an adamantanemethyl group, or a furoylmethyl group, and a symbol,

=== in the above general formula, means a single bond or a double bond.

The term "lower alkyl group" used in the above definition of $R^1$, $R^2$, $R^4$ and $R^5$ with respect to the compound (I) of the present invention is intended to mean a straight-chain or branched alkyl group having 1 to 6 carbon atoms, and examples thereof include methyl, ethyl, propyl, isopropyl, butyl, isobutyl, sec-butyl, tert-butyl, pentyl (amyl), isopenthyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimenthylbutyl, 2,2-dimethylbutyl, 1,3-dimethylbutyl, 2,3-dimenthylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl groups. Among them, methyl, ethyl, propyl, isopropyl groups etc, are preferable. A methyl group is the most preferable.

Examples of the substituent involved in the expression "the following substituted or unsubstituted group: ① a phenyl group, ② a pyridyl group, ③ a pyrazyl group, ④ a quinolyl group, ⑤ an indanyl group, ⑥ a cyclohexyl group, ⑦ a quinoxalyl group, or ⑧ a furyl group" in the definition of $R^1$ include lower alkyl groups having 1 to 6 carbon atoms, such as methyl, ethyl, n-propyl, isopropyl, n-butyl, isobutyl, and tert-butyl groups; lower alkoxy group corresponding to the above-described lower alkyl groups, such as methoxy and ethoxy groups; a nitro group; halogen atoms such as chlorine, bromine, and fluorine; a carboxyl group; lower alkoxycarbonyl groups corresponding to the above-described lower alkoxy groups, such as methoxycarbonyl, ethoxycarbonyl, isopropoxycarbonyl, n-propoxycarbonyl, and n-butyloxycarbonyl groups; an amino group; a lower monoalkylamino group; a lower dialkylamino group, a carbamoyl group; acylamino groups derived from aliphatic saturated monocarboxylic acids having 1 to 6 carbon atoms, such as acetylamino, propionylamino, butyrylamino, isobutyrylamino, valerylamino, and pivaloylamino groups; cycloalkyloxycarbonyl groups such as a cyclohexyloxycarbonyl group; lower alkylaminocarbonyl groups such as methylaminocarbonyl and ethylaminocarbonyl groups; lower alkylcarbonyloxy groups corresponding to the above-defined lower alkyl groups, such as methylcarbonyloxy, ethylcarbonyloxy, and n-propylcarbonyloxy groups; halogentated lower alkyl groups including a trifluoromethyl group; a hydroxyl group; a formyl group; and lower alkoxy lower alkyl groups such as ethoxymethyl, methoxymethyl, and methoxyethyl groups. The "lower alkyl groups" and "lower alkoxyl groups" in the above description of the substituent include all the groups derived from the above-mentioned groups. The substitutent may be one to three of them which may be the same or different.

Further when the substitutent is a phenyl group, the following group is within the scope of the substituted phenyl group:

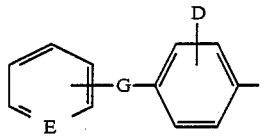

wherein G is a group represented by the formula

a group represented by the formula

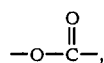

a group represented by the formula —O—, a group represented by the formula

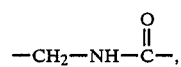

a group represented by the formula —CH₂—O—, a group represented by the formula —CH₂—SO₂—, a group represented by the formula $$-\underset{\underset{OH}{|}}{CH}-,$$

and a group represented by the formula $$-CH_2-\overset{O}{\underset{\|}{S}}-$$

and E is a carbon or nitrogen atom.

Preferable examples of the substituents for the phenyl group among them include lower alkyl, lower alkoxy, nitro, halogenated lower alkyl, lower alkoxycarbonyl, formyl, hydroxyl, and lower alkoxy lower alkyl groups, halogen atoms, and benzoyl and benzylsulfonyl groups. The substituent may be two or more of them which may be the same or different.

Preferable examples of the substituent for the pyridyl group include lower alkyl and amino groups and halogen atoms.

Preferable examples of the substituent for the pyrazyl group include lower alkoxycarbonyl, carboxyl, acylamino, carbamoyl, and cycloalkyloxycarbonyl groups.

With respect to $R^1$, the pyridyl group is preferably a 2-pyridyl, 3-pyridyl, or 4-pyridyl group; the pyrazyl group is preferably a 2-pyrazinyl group; the quinolyl group is preferably a 2-quinolyl or 3-quinolyl group; the quinoxalinyl group is preferable a 2-quinoxalinyl or 3-quinoxalinyl group; and the furyl group is preferably a 2-furyl group.

Specific examples of preferable monovalent or divalent group derived from an indanone having an unsubstituted or substituted phenyl ring include those represented by the following formulae (II) and (III):

(II)

(III)

wherein m's are each an integer of 1 to 4 and A's which may be the same or different are each one of the substituents described in the above items ① to ⑧ of the definition of $R^1$ or a hydrogen atom, preferably a hydrogen atom (i.e. unsubstituted), a lower alkyl group, or a lower alkoxy group, and most preferably the indanone group is unsubstituted or substituted with 1 to 3 methoxy groups.

Examples of the monovalent group derived from a cyclic amide compound include quinazolone, tetrahydroisoquinolinone, tetrahydrobenzodiazepinone, and hexahydrobenzazocinone. However, the monovalent group may be any one having a cyclic amide group in the structural formula thereof and is not limited to the above-described specific examples only. The cyclic amide group may be one derived from a monocyclic or condensed heterocyclic ring. The condensed heterocyclic ring is preferably one formed by condensation with a phenyl ring. In this case, the phenyl ring may be substituted with a lower alkyl group having 1 to 6 carbon atoms, preferably a methyl group, or a lower alkoxy group having 1 to 6 carbon atoms, preferably a methoxy group.

Preferable examples of the monovalent group include the following groups:

(a)

(b)

(c)

(d)

(e)

(f)

(g)

(h)

-continued

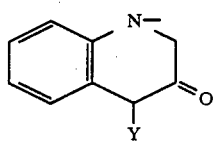 (i)

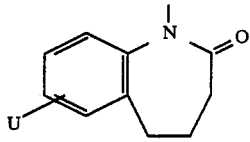 (j)

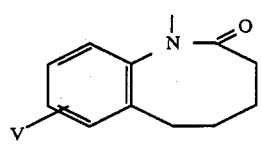 (k)

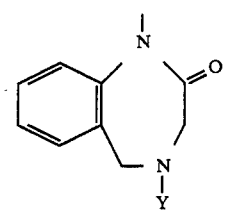 (l)

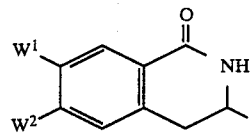 (m)

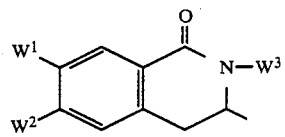 (n)

In the above formulae, Y's in the formulae (i) and (l) are each a hydrogen atom or a lower alkyl group, V in the formula (k) is a hydrogen atom or a lower alkoxy group, $W^1$ and $W^2$ in the formulae (m) and (n) are each a hydrogen atom, a lower alkyl group, or a lower alkoxy group and $W^3$ is a hydrogen atom or a lower alkyl group.

The right-hand ring in each of the formulae (j) and (l) is a seven-membered ring, while the right-hand ring in the formula (k) is an eight-membered ring.

The most preferable examples of the above-defined $R^1$ include a monovalent group derived from an indanone having an unsubstituted or substituted phenyl group and a monovalent group derived from a cyclic amide compound.

The most preferable examples of the above-defined X include a group represented by the formula $-(CH_2)_n-$, a group having an amide group, and groups represented by the above formulae wherein n is 2. Therefore, it is most preferable that any portion of a group represented by the formula $$R'=====X-$$

have a carbonyl or amide group.

The substituents involved in the expressions "a substituted or unsubstituted phenyl group" and "a substituted or unsubstituted arylalkyl group" in the above definition of $R^2$ are the same as those described in the above items ① to ⑧ in the above definition of $R^1$.

The term "arylalkyl group" is intended to mean an unsubstituted benzyl or phenethyl group, etc.

Specific examples of the pyridylmethyl group include 2-pyridylmethyl, 3-pyridylmethyl, and 4-pyridylmethyl groups.

Preferable examples of $R^2$ include benzyl and phenethyl groups. The symbol $$===$$

means either a single or a double bond. This bond is a double bond only when $R^1$ is the above-described divalent group (III) derived from an indanone having an unsubstituted or substituted phenyl ring, while it is a single bond in other cases.

In the present invention, the term "pharmacologically acceptable salt" include those of inorganic acids, such as hydrochloride, sulfate, hydrobromide, and phosphate, and those of organic acids, such as formate, acetate, trifluoroacetate, methanesulfonate, benzenesulfonate, and toluenesulfonate. Further, when a certain kind of substituent is selected, the compound of the present invention may form, e.g., alkali metal salts such as a sodium or potassium salt, alkaline earth metal salts such as a calcium or magnesium salt, organic amine salts such as a salt with trimethylamine, triethylamine, pyridine, picoline, dicyclohexylamine, or N,N'-dibenzylethylenediamine.

Moreover, the compounds of the present invention may have an asymmetric carbon atom depending upon the kind of the substituent and, therefore, have stereoisomers. They are, of course, within the scope of the present invention.

One specific example thereof will now be described. When $R^1$ has an indanone skeleton, the compound of the present invention has an asymmetric carbon atom and, therefore, may have stereoisomers, optical isomers, diastereomers, etc. All of these isomers are within the scope of the present invention.

The compound of the present invention may be prepared by various processes. Representative processes for preparing the compound of the present invention will now be described.

Process A

When X in the general formula (I) is a group represented by the formula

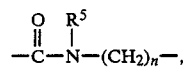

wherein n and $R^5$ are as defined above, the compound of the present invention can be prepared by the following process:

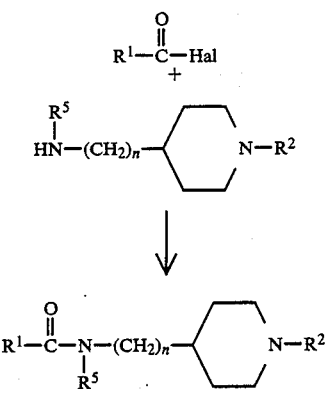

(IV)

(V)

(VI)

Specifically, a compound (VI) which is one of the object compounds of the present invention can easily be prepared by reacting an acyl halide represented by the general formula (IV) with a piperidine derivative represented by the general formula (V) in the presence of a demineralizing agent, such as sodium carbonate, potassium carbonate, sodium hydroxide, potassium hydroxide, sodium hydride, or triethylamine, in an organic solvent, such a chloroform, benzene, toluene, dioxane, tetrahydrofuran, or dimethylformamide (DMF), while cooling the reaction mixture or at room temperature or while heating the reaction mixture.

Process B

When $R^1$ in the general formula (I) is a monovalent or divalent group derived from an indanone having an unsubstituted or substituted phenyl group and X is a group represented by the formula $-(CH_2)_n-$, wherein n is an integer of 1 to 6, the compound of the present invention can be prepared also by the following process:

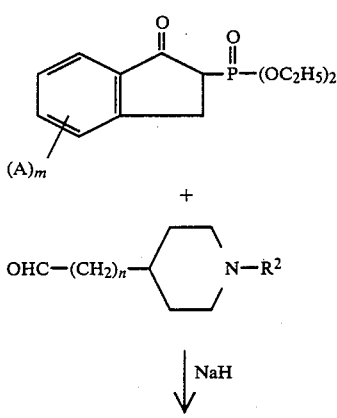

(VII)

(VIII)

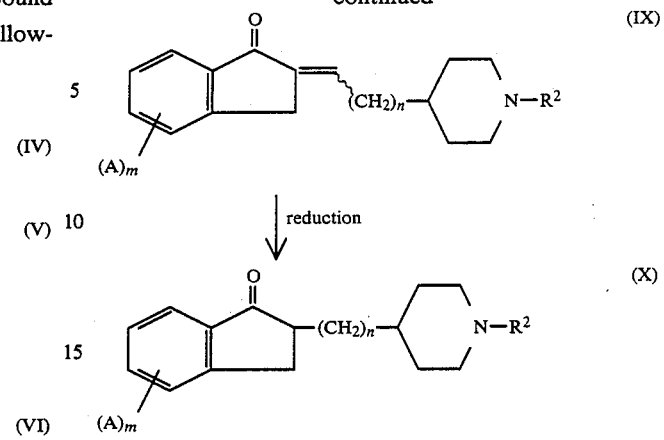

(IX)

(X)

Specifically, a compound (X) which is one of the object compounds can be prepared by reacting a substituted 1-indanon-2-ylphosphonate represented by the general formula (VII) with an aldehyde compound represented by the formula (VIII) (i.e., Wittig reaction) to prepare a compound (IX) which is one of the object compounds and then catalytically reducing said compound (IX).

Examples of the catalyst used in the Wittig reaction include sodium methylate (MeONa), sodium ethylate (EtONa), tert-BuOK, and NaH. Examples of the solvent used in this reaction include tetrahydrofuran (THF), dimethylformamide (DMF), ether, nitromethane, and dimethyl sufoxide (DMSO). A reaction temperature ranging from room temperature to about 100° C. provides favorable results.

A catalytic reduction in the presence of a catalyst composed of palladium-carbon etc. provides favorable results.

The following scheme specifically shows a process for preparing the compound of the present invention, wherein $R^1$ is a group represented by the formula

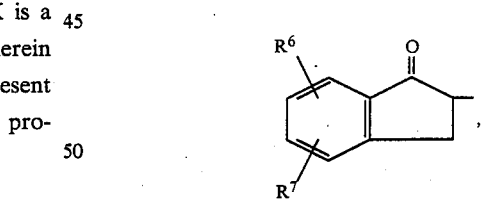

wherein $R^6$ and $R^7$ may be the same or different and are each a hydrogen atom, a lower alkyl group, a lower alkylalkoxy group, or a halogen atom among the groups defined by A, X is a group represented by the formula $-(CH_2)_n-$, wherein n is an integer of 1 to 6, $R^2$ is a group represented by the formula

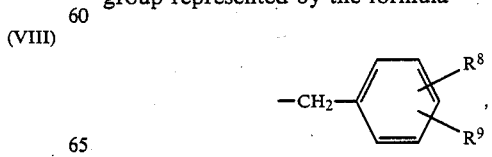

wherein $R^8$ and $R^9$ each have the same meaning as that of $R^6$ and $R^7$:

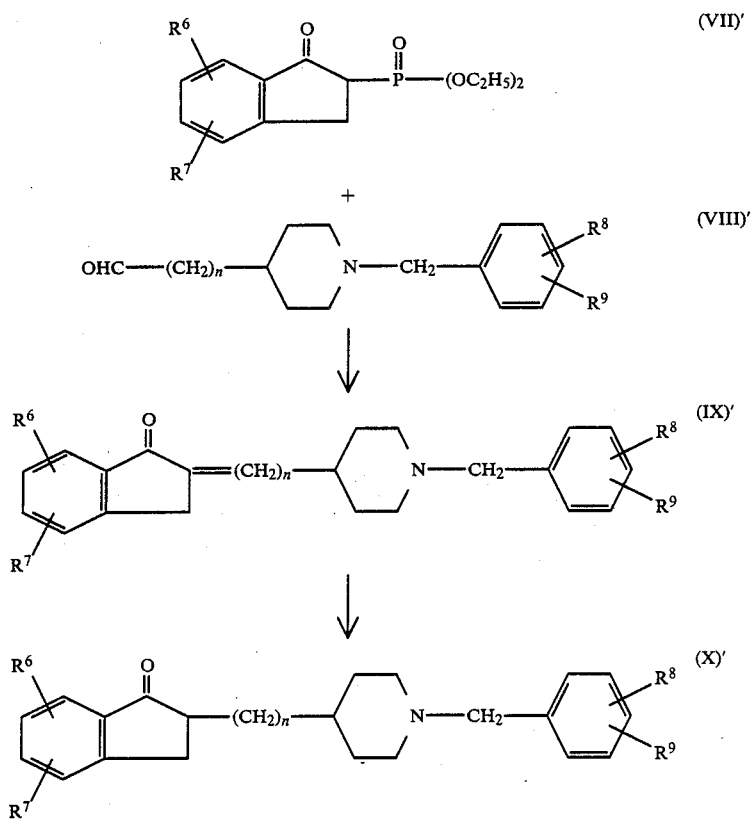

Process C

When $R^1$ in the general formula (I) is a monovalent or divalent group derived from an indanone having an unsubstituted or substituted phenyl group and X is a group represented by the formula —$(CH_2)_n$—, wherein n is an integer of 1 to 6, the compound of the present invention can be prepared also by the following process:

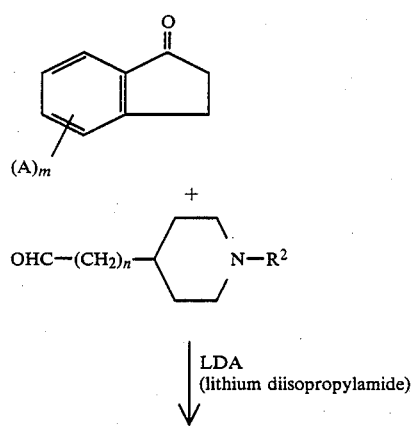

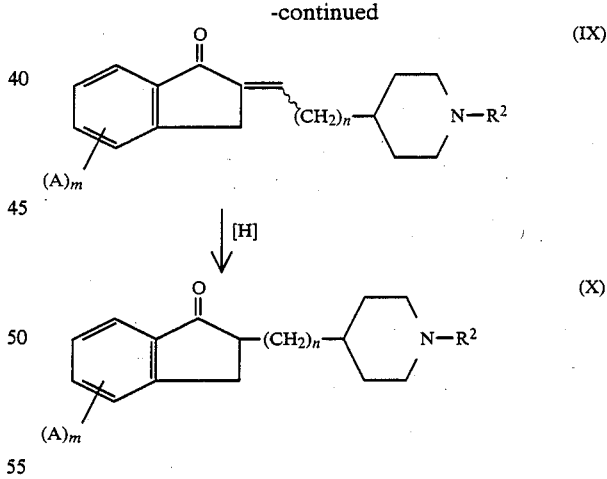

Specifically, for example, diisopropylamine and n-butyllithium/hexane are added to a solvent such as tetrahydrofuran. A substituted 1-indanone represented by the general formula (XI) and hexamethylphosphoric amide are added thereto at a temperature of preferably about −80° C. Then an aldehyde compound represented by the general formula (VIII) are added thereto, followed by a reaction according to an ordinary method. The reaction mixture is subjected to dehydration, thereby preparing a compound (IX). This compound may be catalytically reduced in the same manner as that of the Process B to prepare a compound (X).

A specific example of the Process C will now be described in the same manner as that described in the Process B.

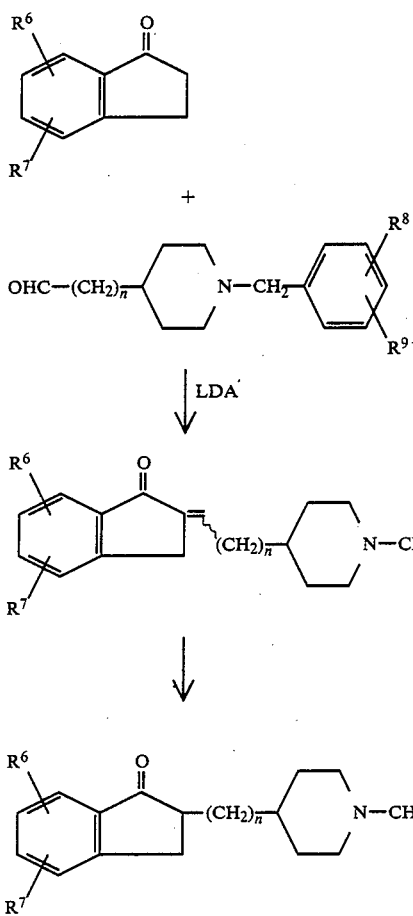

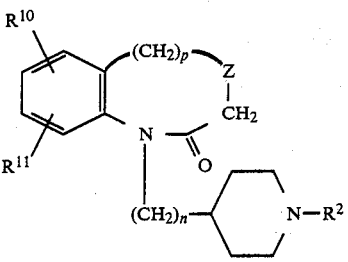

wherein $R^{10}$ and $R^{11}$ are each a hydrogen atom, a lower alkyl group, a lower alkoxy group, or a halogen atom, n is an integer of 1 to 6, p is an integer of 1 to 3 and Z is a group represented by the formula —CH$_2$— or a group represented by the formula

wherein $R^{12}$ is a hydrogen atom or a lower alkyl group.

Specifically, a substituted 1,2,3,4-tetrahydro-5H-1-benzazepin-2-one is allowed to condense with a substituted N-benzyl-4-(2-halognoethyl)piperidine represented by the general formula (XIII) in a solvent, e.g., dimethylformamide, in the presence of, e.g., sodium hydride, thereby preparing a compound (XIV) which is one of the object compounds.

Process E

When $R^1$ is a group represented by the formula

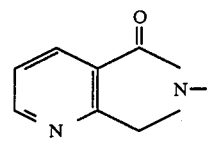

and X is a group represented by the formula —(CH$_2$)$_n$—, the compound of the present invention can be prepared also by the following process:

Process D

When $R^1$ is a monovalent group derived from a cyclic amide compound selected from among quinazolone, tetrahydroisoquinolinone, tetrahydrobenzodiazepinone, and hexahydrobenzazocinone, the compound of the present invention can be prepared also by the following process:

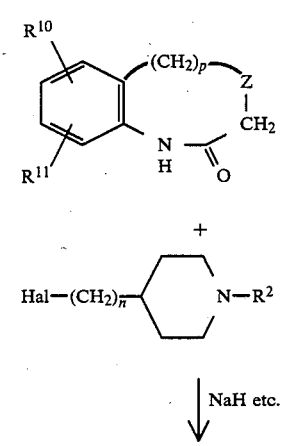

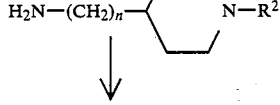

+

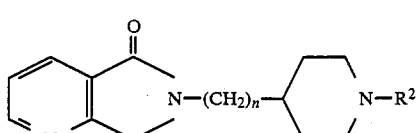

Specifically, 2-hydroxymethylnicotinic acid lactone (XV) is reacted with a substituted N-benzyl (2-aminoethyl)-piperidine represented by the general formula (XVI) by an ordinary method to prepare a compound represented by the general formula (XVII) which is one of the object compounds. The reaction temperature is preferably about 200° C.

Process F

When R¹ in the general formula (I) is a group represented by the formula

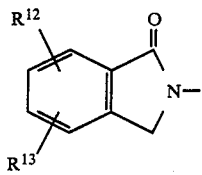

and X is a group represented by the formula —(CH$_2$)$_n$—, the compound of the present invention can be prepared also by the following process:

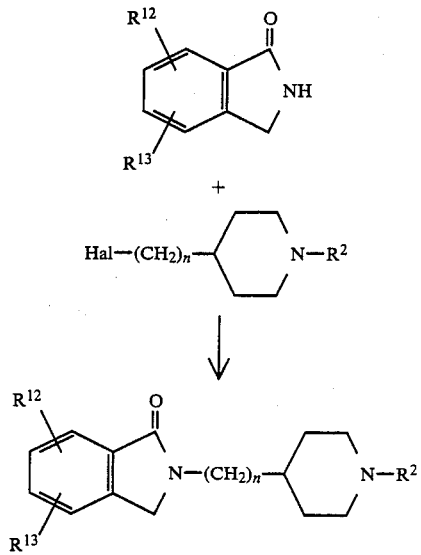

(XVIII)

(XIII)

(XIX)

Specifically, a substituted 2,3-dihydroxypyrrolo(3,4-b)benzene represented by the general formula (XVIII) is reacted with a substituted N-benzyl(2-halogenoethyl)piperidine represented by the general formula (XIII) in the presence of, e.g., sodium hydride, in a solvent, such as dimethylformamide, while heating the reaction mixture, thereby preparing a compound (XIV) which is one of the object compounds.

Process G

When R¹ in the general formula (I) is a group represented by the formula

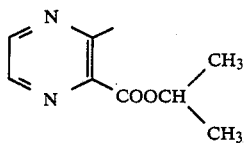

and X is a group represented by the formula —CONH—(CH$_2$)$_n$—, the compound of the present invention can be prepared also by the following process:

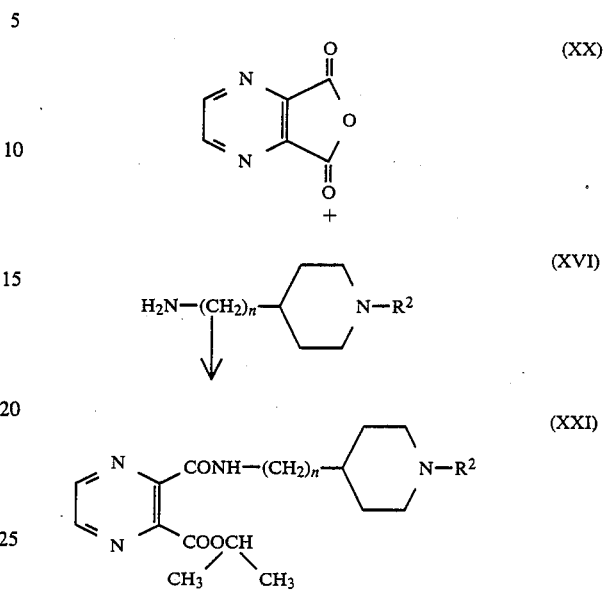

(XX)

(XVI)

(XXI)

Specifically, 2,3-pyrazylcarboxylic anhydride (XX) is added to, e.g., isopropyl alcohol, followed by reflux. The alcohol is distilled off, and the residue is reacted with a substituted N-benzyl(ω-amino-alkyl) piperidine in a solvent, such as tetrahydrofuran, thereby preparing a compound (XXI) which is one of the object compounds.

Process H

When R¹ in the general formula (I) is an unsubstituted or substituted phenyl group and X is a group represented by the formula

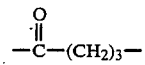

the compound of the present invention can be prepared also by the following process:

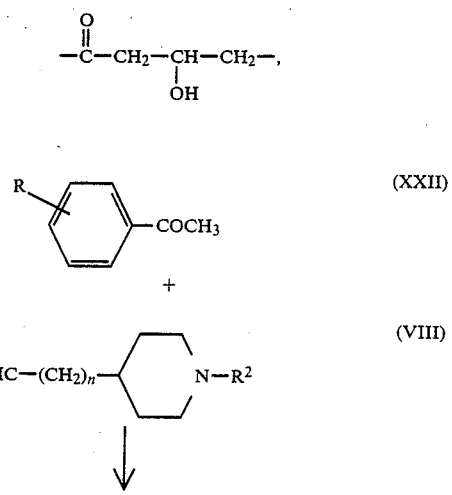

(XXII)

(VIII)

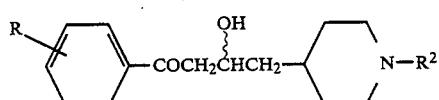 (XXIII)

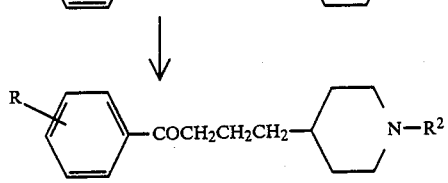 (XXIV)

or a group represented by the formula

Specifically, diisopropylamine and n-butyl-lithium/hexane are added to a solvent such as tetrahydrofuran. In the presence of this mixture, an acetophenone represented by the general formula (XXII) is allowed to condense with a substituted N-benzyl (ω-formylalkyl)-piperidine, thereby preparing a compound (XXIII). This compound is dehydrated in the presence of, e.g., p-toluenesulfonic acid in a solvent, such as toluene, followed by catalytic reduction according to an ordinary method, thereby preparing a compound (XXIV) which is one of the object compounds.

Process I
procedure 1

The cyclic amine compound having the formula (XXV) in which J is (1) indanyl, (2) indanonyl, (5) indanedionyl, (6) tetralonyl, (7) benzosuberonyl or propyophenyl and B is —(CHR22)r—, =(CH—CH=CH)b—, =CH—(CH2)c— or =(CH—CH)d= can be produced by the following procedure. B' is a group where the terminal group containing one carbon atom is excluded from B.

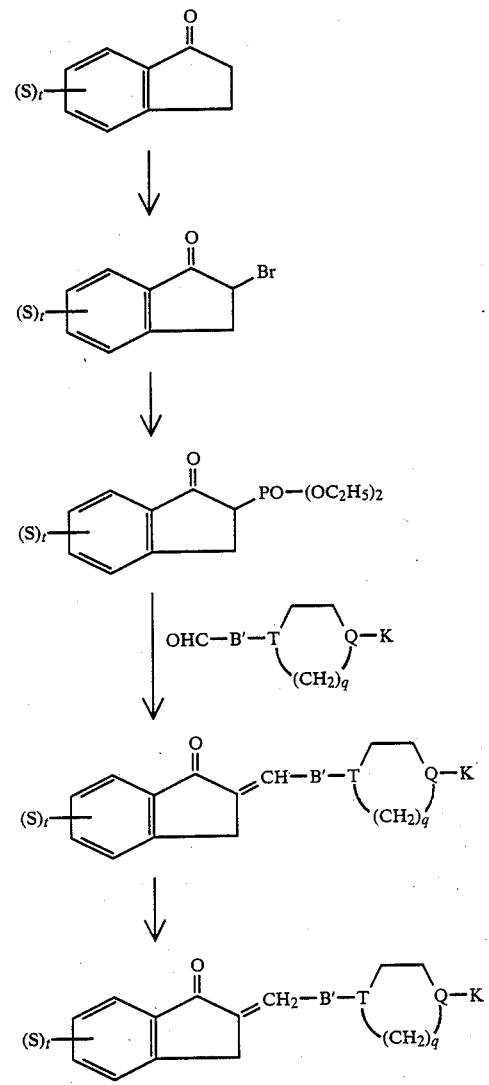

In this procedure, the phosphate is reacted with an aldehyde compound through the Wittig reaction and the product is catalytically reduced. The catalyst to use in the Wittig reaction, includes sodium methylate, sodium ethylate, potassium t-butyrate or sodium hydride. The reaction may be carried out in a solvent such as tetrahydrofuran, dimethylformamide, ether, nitromethane and dimethylsulfoxide at a temperature of the room temperature to 100° C. In the catalytical reduction, it is preferable to use a catalyst such as a catalyst of palladium and carbon, Raney nickel and a catalyst of rhodium and carbon.

In the above shown procedure, one example in which J is indanonyl goes:

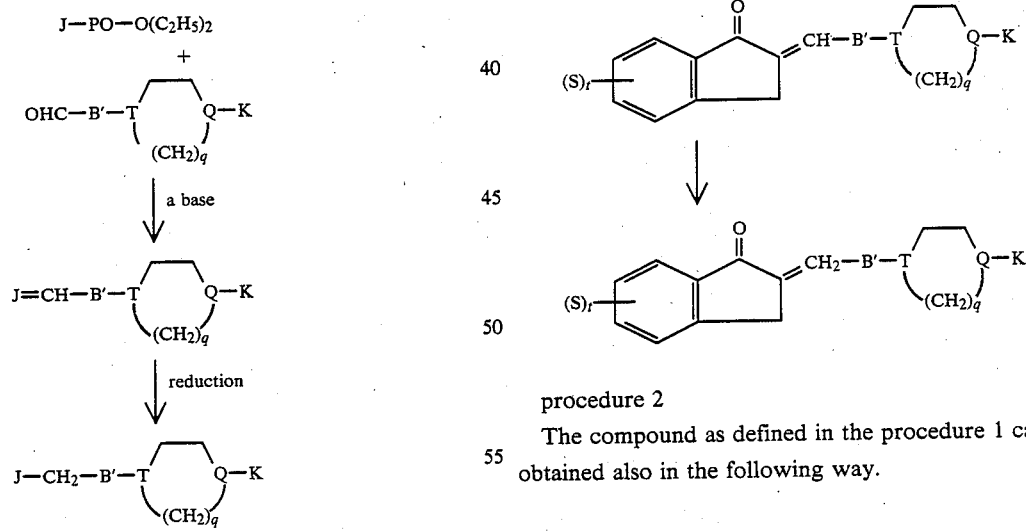

procedure 2

The compound as defined in the procedure 1 can be obtained also in the following way.

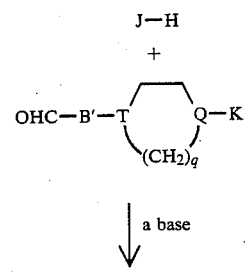

-continued

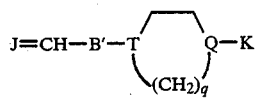

↓ reduction

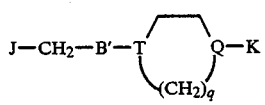

The compound of J–H such as indanone is reacted with an aldehyde by the conventional Aldol condensation to obtain an intended compound. The reaction may be carried out in a solvent such as tetrahydrofuran by first producing lithium di-isopropylamide from diisopropylamine and a n-butylhexane solution of lithium, adding thereto a compound of J–H at a temperature of preferably about minus 80° C., then adding the aldehyde thereto, effecting the reaction in the conventional way, heating the production mixture up to the room temperature to conduct dehydration and obtain the enone body of the intended compound. In another manner, the two reactants are dissolved in a solvent such as tetrahydrofuran, a base such as sodium methylate is added to the solution at about 0° C. and the reaction is effected at the room temperature.

The enone body obtained this way can be reduced to obtain the intended compound.

One example in which J is indanonyl, B is —(CH$_2$)$_r$— and T is carbon, Q is nitrogen and q is 2 goes:

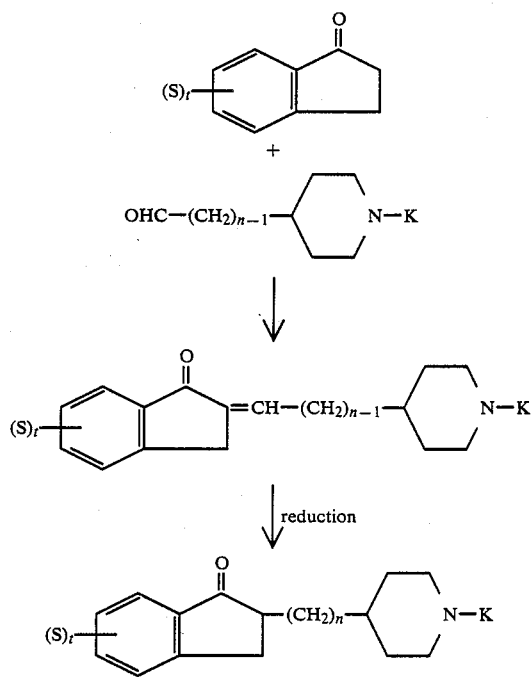

Process J

The compound having indanol is produced by the following procedure. This procedure applies to the compound having indanol having a substituent(s) on the phenyl group.

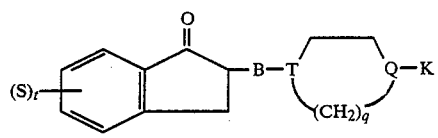

↓ reduction with NaBH$_4$

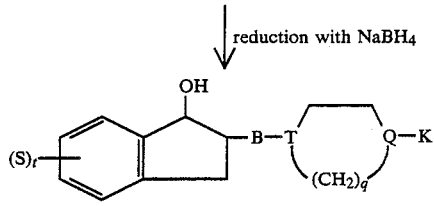

The reduction is effected with sodium boron hydride at 0° C. to the room temperature in a solvent such as methanol.

Process K

The compound having indenyl is produced by the following procedure. This procedure applies to the compound having indenyl having a substituent(s) on the phenyl.

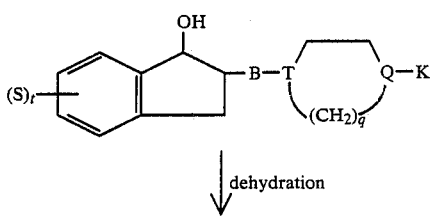

↓ dehydration

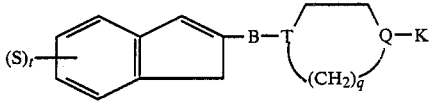

The dehydration is effected conventionally, for example, with hydrochloric acid.

Process L

The compound having indenonyl is produced by the following procedure. This procedure applies to the compound having indenonyl having a substituent(s) on the phenyl.

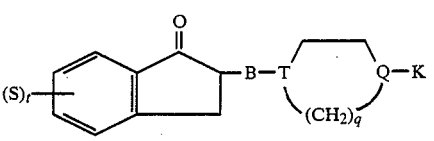

↓ NBS

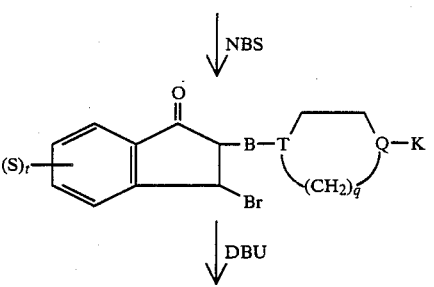

↓ DBU

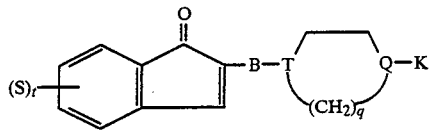

The above shown starting compound having indanone is heated for reflux in a solvent such as carbon tetrachloride in the presence of N-bromosuccinic imide (NBS) and benzoyl peroxide to obtain its bromide and the bromide is heated for reflux in a solvent such as tetrahydrofuran with 1,8-diazabicyclo(5.4.0)undec-7-ene (DBU) to conduct the beta-elimination and obtain the indenone compound. The bromide may be replaced by another halogenated compound.

The indanone compound, as used in the above shown processes I, J, K and L, is available in the commertial market and is produced by the following procedures.

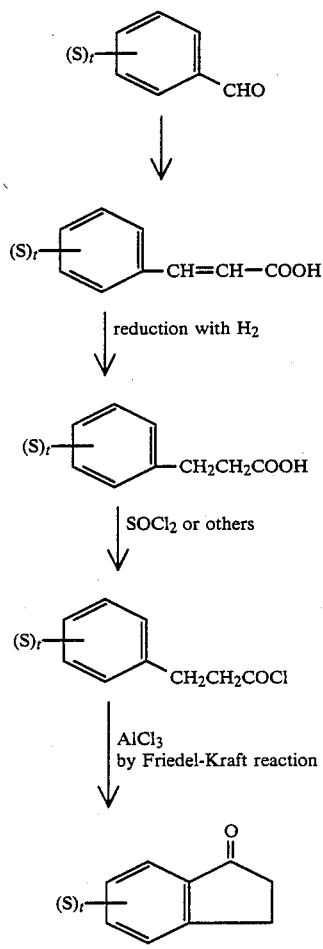

The aldehyde compound used above is produced by the following procedures.

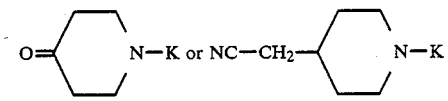

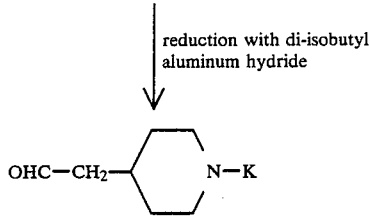

The above shown starting compound is converted to its aldehyde and the aldehyde is used for the Wittig reaction to increase the carbon number contained therein. The Wittig reaction is effected repeatedly or combined with another kind of the Wittig reaction. This is obvious to a man skilled in the art. The Wittig agent includes methoxymethylenetriphenylphosphorane to add one carbon atom and formylmethylenetriphenylphosphorane to add two carbon atoms. Methoxymethylenetriphenylphosphorane is obtained by the reaction between methoxymethylenetriphenylphosphonium chloride and n-butyl lithium in ether or tetrahydrofuran. Then a ketone compound or an aldehyde compound is added to the product mixture to obtain its methoxyvinyl compound and the resulting mixture is treated with an acid to obtain a corresponding aldehyde. One example goes:

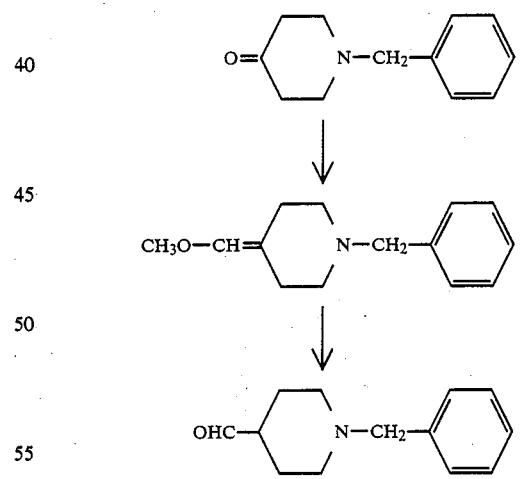

When formylmethylenetriphenylphosphorane is used, a solution of a starting ketone or aldehyde in ether, tetrahydrofuran or benzene is mixed with this Wittig agent and the mixture is heated for reflux to obtain an intended compound.

The obtained unsaturated aldehyde compound may be converted to its saturated compound by the catalytic reduction using a catalyst of palladium and carbon, Raney nickel or a catalyst of rhodium and carbon. One example goes:

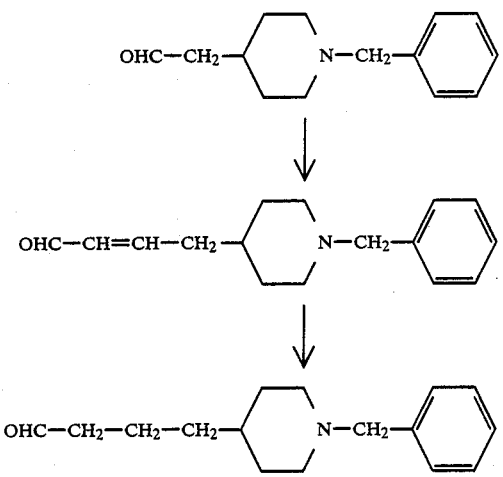

The compounds thus prepared and acid addition salts thereof represented by the general formula (I) are useful for treatment of various kinds of senile dementia, in particular senile dementia of the Alzheimer type.

The invention will be described in view of its therapeutical usefulness together with pharmacologically experimental data.

Experimental Example 1

In vitro acetylcholinesterase inhibitory action

A mouse brain homogenate was used as an acetylcholinesterase source and the esterase activity thereof was determined according to the method of Ellman et al.

Ellman, G. L., Courtney, K. D., Andres, V., and Featherstone, R. M., (1961) Biochem. Pharmacol., 7, 88–95.

Acetylthiocholine as a substrate, a sample to detect and DTNB were added to the mouse brain homogenate, followed by incubation. The amount of a yellow substance formed by the reaction between the thiocholine and DTNB was determined in the absorbance at 412 nm in terms of the acetylcholinesterase activity.

The acetylcholinesterase inhibitory activity of the sample was expressed in terms of inhibitory concentration 50% ($IC_{50}$).

The results are shown in Table 1.

TABLE 1

| Compound | AChE inhibitory activity $IC_{50}$ ($\mu M$) | Compound | AChE inhibitory activity $IC_{50}$ ($\mu M$) |
|---|---|---|---|
| 1 | 0.23 | 31 | 0.025 |
| 4 | 0.0053 | 33 | 0.030 |
| 5 | 0.10 | 45 | 0.36 |
| 6 | 0.017 | 48 | 0.019 |
| 8 | 0.013 | 52 | 0.80 |
| 9 | 0.051 | 54 | 1.0 |
| 10 | 0.009 | 56 | 0.017 |
| 11 | 0.068 | 62 | 0.0075 |
| 12 | 0.040 | 65 | 0.0016 |
| 13 | 0.026 | 67 | 0.10 |
| 14 | 0.038 | 70 | 0.28 |
| 15 | 0.094 | 72 | 0.020 |
| 17 | 0.052 | 89 | 0.018 |
| 18 | 0.68 | 90 | 0.035 |
| 19 | 0.064 | 95 | 0.085 |
| 20 | 0.54 | 101 | 0.11 |
| 21 | 50 | 120 | 0.19 |
| 23 | 0.072 | 124 | 2.8 |
| 24 | 1.1 | 176 | 0.004 |
| 26 | 24 | | |
| 27 | 0.41 | | |
| 29 | 0.15 | | |

Experimental Example 2

Ex vivo acetylcholinesterase inhibitory action

A sample to detect was orally administered to rats. After one hour of the administration, the cerebral hemispheres were dissected and homogenized, followed by the determination of the acetylcholinesterase activity. The group of rats treated with physiological saline was used as the control. Inhibition of AChE by samples ex vivo was expressed in terms of inhibition percent of the control value. Results are shown in Table 2

Experimental Example 3

Action on passive avoidance learning impairment induced by scopolamine

See Z. Bokolanecky & Jarvik: Int. J. Neuropharmacol, 6, 217–222(1967).

Male Wistar rats were used as the test animal and a step-through light and dark box was used as an apparatus. A sample to detect was orally administered one hour before the training and the rats were treated with 0.5 mg/kg (i.p.) of scopolamine 30 min. before the training. In a training experiment, the animal was placed into a light room and, just after the animal had entered into a dark room, a guillotine door was closed, followed by delivery of an electric shock from the gid of the floor. After six hours, the animal was again placed into a light room for a retention experiment, and the time taken for the animal to enter the dark room was measured for evaluation of the effect of the sample.

The difference in the response time between the physiological saline administration group and the scopolamine administration group was taken as 100%, and the effect of the sample was expressed in terms of the percentage antagonism by the sample (Reverse %).

The results are shown in Table 3.

TABLE 2

| Compd. No. | Dose (mg/kg) | AChE inhibitory action (%) |
|---|---|---|
| Saline | | 0 |
| 4 | 1 | 5* |
| | 3 | 17** |
| | 10 | 36** |
| | 30 | 47** |
| 15 | 10 | 5 |
| | 30 | 14** |
| | 100 | 18** |

TABLE 3

| Compd. No. | Dose (mg/kg) | Reverse % |
|---|---|---|
| 4 | 0.125 | 55 |
| | 0.25 | 36 |
| 13 | 0.25 | 39 |

TABLE 3-continued

| Compd. No. | Dose (mg/kg) | Reverse % |
|---|---|---|
|  | 0.5 | 27 |
| 15 | 1.0 | 51 |
|  | 2.0 | 30 |
| 19 | 0.5 | 37 |
|  | 1.0 | 39 |
| 69 | 0.5 | 22 |
|  | 1.0 | 38 |

The number of animals per dose was 10 to 17.
NE: non-effective

The above-described pharmacological experiments revealed that the compound of the present invention had a potent acetylcholinesterase inhibitory action.

Among the compounds (I) of the present invention, the compound wherein $R^1$ is a group (II) or (III) derived from an indanone having an unsubstituted or substituted phenyl ring is preferable, and the compound wherein $R^1$ is a group represented by the general formula (II) are the most preferable. Specifically, particularly a compound wherein $R^1$ is a group derived from an indanone having an unsubstituted or substituted phenyl ring has characteristics such as remarkable difference from the conventional acetylcholinesterase inhibitor in the structure, advantages with respect to the manufacture of pharmaceutical preparations by virtue of the potent acetylcholinesterase inhibitory action, large width between the main and the side effects, persistent activity, high water solubility, excellent stability, advantage in formulating into preparations, high bioavailability and excellent penetration into the brain.

Therefore, the objects of the present invention are to provide a novel compound effective for various kinds of dementia and the sequelae of cerebrovascular disease, to provide a process for preparing the same, and to provide a novel pharmaceutical comprising the same as an effective ingredient.

Representative compounds of the present invention (Compd. Nos. 4, 13, 15, 19, and 69 in the above Table 3) were applied to toxicity tests on rats. As a result, all the compounds exhibited a toxicity of 100 mg/kg or more, i.e., exhibited no serious toxicity.

The compound of the present invention is effective for treatment, prevention, remission, improvement, etc. of various kinds of senile dementia, particularly senile dementia of the Alzheimer type; cerebrovascular disease accompanying cerebral apoplexy, e.g. cerebral hemorrhage or cerebral infarcts, cerebral arteriosclerosis, head injury, etc.; and aprosexia, disturbance of speech, hypobulia, emotional changes, recent memory disturbance, hallucinatory-paranoid syndrome, behavioral changes, etc. accompanying encephalitis, cerebral palsy, etc.

Further, the compound of the present invention has a strong and highly selective anticholinesterase action, which renders the compound of the present invention useful also as a pharmaceutical based on this kind of action.

Specifically, the compound of the present invention is effective for, for example, Huntington's chorea, Pick's disease and delayed ataxia or tardive dyskinesia other than senile dementia of the Alzheimer type.

When the compound of the present invention is used as a pharmaceutical for these diseases, it may be orally or parenterally administered. In general, it is parenterally administered in the form of injections, such as intravenous, subcutaneous, and intramuscular injections, suppositories, or sublingual tablets. The dose will remarkably vary depending upon the symptom; age, sex, weight, and sensitivity of patients; method of administration; time and intervals of administration and properties, dispensing, and kind of pharmaceutical preparations; kind of effective ingredients, etc., so that there is no particular limitation with respect to the dose. Normally the compound may be administered in a dose of about 0.1 to 300 mg, preferably 1 to 100 mg, per day per adult, ordinarily in one to four portions.

Pharmaceutical preparations in the dosage form of, e.g., injections, suppositories, sublingual tablets, tablets, and capsules are prepared according to a method which is commonly accepted in the art.

In preparing injections, the effective ingredient is blended, if necessary, with a pH modifier, a buffer, a suspending agent, a solubilizing agent, a stabilizer, a tonicity agent, a preservative, etc., followed by preparation of an intravenous, subcutaneous, or intramuscular injection according to an ordinary method. In this case, if necessary, it is possible to lyophilize these preparations according to an ordinary method.

Examples of the suspending agents include methylcellulose, Polysorbate 80, hydroxyethylcellulose, acacia, powdered tragacanth, sodium carboxymethylcellulose, and polyoxyethylene sorbitan monolaurate.

Examples of the solubilizing agent include polyoxyethylene hydrogenated castor oil, Polysorbate 80, nicotinamide, polyoxyethylene sorbitan monolaurate, Macrogol, and an ethyl ester of castor oil fatty acid.

Examples of the stabilizer include sodium sulfite, sodium metasulfite, and ether, and examples of the preservative include methyl p-hydroxybenzoate, ethyl p-hydroxybenzoate, sorbic acid, phenol, cresol, and chlorocresol.

EXAMPLES

The present invention will now be described in more detail with reference to the following Examples. It is needless to say that the technical scope of the invention of the present invention is not limited to these Examples only.

In the following examples, all of the NMR values are those of the compounds measured in free form.

EXAMPLE 1

1-Benzyl-4-[2-[(1-indanon)-2-yl]]ethylpiperidine hydrochloride

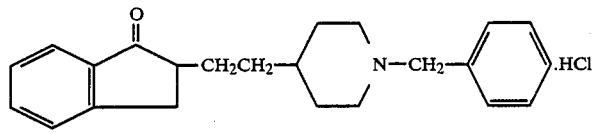

0.37 g of 1-benzyl-4-[2-[1-indanon)-2-yl]]-ethylpiperidine was dissolved in 10 ml of methanol, followed by addition of 0.1 g of 5% rhodium-carbon. The mixture was hydrogenated at room temperature under atmospheric pressure for 24 hr. The catalyst was filtered off, and the filtrate was concentrated in vacuo. The residue was purified by making use of a silica gel column (methylene chloride:methanol=200:1). The eluate was concentrated vacuo, and the residue was dissolved in methylene chloride. A 10% solution of hydrochloric acid in ethyl acetate was added to the resulting solution, followed by concentration in vacuo to obtain a crystal, which was recrystallized from methanol/IPE to obtain 0.33 g (yield: 80%) of the title compound having the following properties:

m.p. (°C.): 224°-225° C.
elementary analysis: $C_{23}H_{27}NO.HCl$

|  | C | H | N |
| --- | --- | --- | --- |
| calculated (%) | 74.68 | 7.63 | 3.79 |
| found (%) | 74.66 | 7.65 | 3.77 |

EXAMPLE 2

1-Benzyl-4-[2-[(1-indanon)-2-ylidenyl]]ethylpiperidine hydrochloride

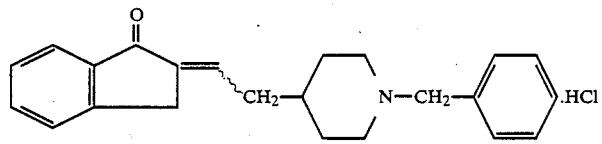

0.32 g of 60% sodium hydride was washed with hexane, and 10 ml of THF was added thereto. A solution of 2.12 g of diethyl 1-indanon-2-ylphosphonate in 30 ml of THF was dropwise added thereto at 0° C. The mixture was stirred at room temperature for 30 min and again cooled to 0° C., followed by addition of a solution of 3.43 g of 1-benzyl-4-piperidineacetoaldehyde in 10 ml of DMF. The mixture was stirred at room temperature for 2 hr and at 50° C. for 2 hr and then refluxed for 2 hr while heating the mixture. Methanol and 20% sulfuric acid were added at 0° C. to the reaction mixture. 10 min after the addition, the reaction mixture was made basic with an aqueous sodium hydroxide solution and extracted with ethyl acetate. The organic phase was washed with a saturated saline solution, dried over magnesium sulfate, and concentrated in vacuo. The resulting residue was purified by making use of a silica gel column (methylene chloride:methanol=500:1). The eluate was concentrated in vacuo, and the residue was dissolved in methylene chloride. A 10% solution of hydrochloric acid in ethyl acetate was added to the resulting solution, followed by concentration in vacuo to obtain 0.78 g (yield: 27%) of the title compound. 1.37 of diethyl 1-indanon-2-ylphosphorate was also recovered.

molecular formula; $C_{23}H_{25}NO.HCl$
$^1H$—NMR(CDCl$_3$) δ; 1.10~2.13 (7H, m), 2.26 (2H, t), 2.88 (2H, bd), 3.48 (2H, s), 6.72~7.07 (2H, m), 7.30 (5H, s), 7.10~8.00 (5H, m)

EXAMPLE 3

1-benzyl-4-piperidine-carboaldehyde having the formula:

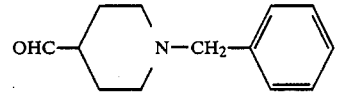

was prepared in the following way.

26 grams of methoxymethylene-triphenylphosophonium chloride was suspended in 200 ml of anhydrous ether. 1.6M solution in hexane of n-butyl lithium was added dropwise to the suspension at the room temperature. The mixture was stirred at the room temperature for 30 minutes and cooled down to 0° C. Then 30 ml of a solution in anhydrous ether of 14.35 g of 1-benzyl-4-piperidone was added to the mixture. It was stirred at the room temperature for 3 hours and filtrated to remove out the insoluble. The filtrate liquid was concentrated at a reduced pressure. The obtained concentrate was dissolved in ether and extracted with 1N hydrochloric acid. An aqueous solution of sodium hydroxide was added to the extract to have pH value of 12. The resultant was extracted with methylene chloride. The extract was dried with magnesium sulfate and concentrated at a reduced pressure. The residue was purified with a column filled with silica gel to obtain 5.50 g of an oil with a yield of 33 percent.

The oil was incorporated into 40 ml of methanol and 40 ml of 1N hydrochloric acid was added to the solution. It was heated so as to make reflux for 3 hours and then concentrated at a reduced pressure. The residue was dissolved in water. An aqueous solution of sodium hydroxide was added to the solution to have a pH value of 12 and the solution was extracted with methylene chloride. The extract was washed with saturated salt solution and dried with magnesium sulfate. It was further concentrated at a reduced pressure and the residue was purified in a column charged with silica gel. 2.77 g of the intended compound was obtained with a yield of 54 percent. In analysis, its molecular formula was found to be C13H17NO and 1H—NMR (CDCl3) δ, 1.40–2.40 (7H, m), 2.78 (2H, dt), 3.45 (2H, S), 7.20 (5H, S), 9.51 (1H, d).

The compound may be produced according to the methods shown in (1) Arm. Kim. Zh., 36(9), 614–17 (1983) by R. A. Kuroyan, A. I. Markosyan, G. M. Snkhchyan and S. A. Vartangan and (2) Ind. Chim. Belge, 32, 64–5 (1967) by B. Hermans and P. Van Daele.

1-Benzyl-4-[(5,6-dimethoxy-1-indanon)-2-ylidenyl-methylpiperidine hydrochloride

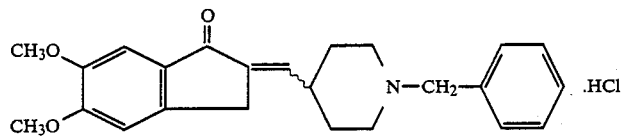

This reaction was conducted in an argon atmosphere.

2.05 ml of diisopropylamine was added to 10 ml of anhydrous THF, followed by addition of 9.12 ml of a 1.6M solution of n-butyllithium in hexane at 0° C. The mixture was stirred at 0° C. for 10 min and then cooled to −78° C., and a solution of 2.55 g of 5,6-dimethoxy-1-indanone in 30 ml of anhydrous THF and 2.31 ml of hexamethyl-phosphoric amide were added thereto. The mixture was stirred at −78° C. for 15 min, and a solution of 2.70 g of 1-benzyl-4-piperidinecarboaldehyde in 30 ml of anhydrous THF was added thereto. The temperature of the mixture was gradually raised to room temperature, followed by stirring for 2 hr. An aqueous 1% ammonium chloride solution was added thereto, and the organic phase was separated. The water phase was extracted with ethyl acetate, and the organic phases were combined with each other. The combined organic phase was washed with a saturated saline solution, dried over magnesium sulfate, and concentrated in vacuo. The resulting residue was purified by making use of a silica gel column (methylene chloride:methanol=500-:1-100: 1). The eluate was concentrated in vacuo, and the residue was dissolved in methylene chloride. A 10% solution of hydrochloric acid in ethyl acetate was added to the resulting solution, followed by concentration in vacuo to obtain a crystal, which was recrystallized from methanol/IPE to obtain 3.40 g (yield: 62%) of the title compound having the following properties:

m.p. (°C.): 237°–238° C. (dec.)
elementary analysis: C24H7NO3.HCl

|  | C | H | N |
| --- | --- | --- | --- |
| calculated (%) | 69.64 | 6.82 | 3.38 |
| found (%) | 69.51 | 6.78 | 3.30 |

EXAMPLE 4

1-Benzyl-4-[(5,6-dimethoxy-1-indanon)-2-yl]-methylpiperidine hydrochloride

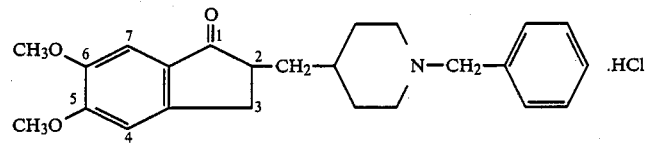

0.4 g of 1-benzyl-4-[(5,6-dimethoxy-1-indanon)-2-ylidenyl]methylpiperidine was dissolved in 16 ml of THF, followed by addition of 0.04 g of 10% palladium-carbon. The mixture was hydrogenated at room temperature under atmospheric pressure for 6 hr. The catalyst was filtered off, and the filtrate was concentrated in vacuo. The residue was purified by making use of a silica gel column (methylene chloride: methanol=50: 1). The eluate was concentrated in vacuo, and the residue was dissolved in methylene chloride. A 10% solution of hydrochloric acid in ethyl acetate was added to the resulting solution, followed by concentration in vacuo to obtain a crystal, which was recrystallized from methanol/IPE to obtain 0.36 g (yield: 82%) of the title compound having the following properties:

m.p. (°C.): 211°–212° C. (dec.) elementary analysis: C24H29NO3.HCl

|  | C | H | N |
| --- | --- | --- | --- |
| calculated (%) | 69.30 | 7.27 | 3.37 |
| found (%) | 69.33 | 7.15 | 3.22 |

EXAMPLE 5

2-[4′-(1′-Benzylpiperidine)ethyl]-2,3-dihydro-1-oxypyrrolo[3,4-b]pyridine dihydrochloride

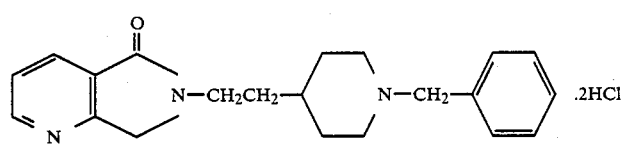

12.6 g of 2-hydroxymethylnicotinic acid lactone and 40 g of 4-(2-aminoethyl)benzylpiperazine were stirred in a sealed tube at 200° C. for 7 hr. Thereafter, the reaction mixture was purified by making use of a silica gel column, and a hydrochloride of the purified product was prepared by an ordinary method, thereby preparing 6.37 g of dihydrochloride of the object compound.

m.p. (°C.): 143.5°–145° C.

elementary analysis: $C_{21}H_{25}N_3O \cdot 2HCl$

|  | C | H | N |
|---|---|---|---|
| calculated (%) | 61.77 | 6.66 | 10.29 |
| found (%) | 61.49 | 6.68 | 9.98 |

EXAMPLE 6

2-[4'-Benzylpiperidine)ethyl]-2,3-dihydro-5,6-dimethoxyoxypyrrolo[3,4-]benzene hydrochloride

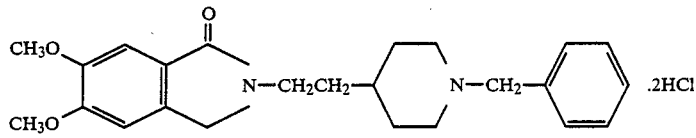

0.5 g of 2,3-dihydro-5,6-dimethoxyoxypyrrolo[3,4-b]benzene was dissolved together with a catalytic amount of potassium iodide in DMF. 0.21 g of sodium hydride (60%) was added to the resulting solution while cooling and stirring the solution. Thereafter, 1 g of 2,3-dihydro-5,6-dimethoxyoxypyrrolo[3,4-b]-benzene was added thereto, and the mixture was stirred at 80° C. for 4 hr. After the completion of the stirring, H$_2$O was added thereto, followed by extraction with chloroform. The chloroform phase was washed with water and dried (over MgSO$_4$). The solvent was distilled off, and the residue was purified with silica gel, thereby preparing an oleaginous object compound. A hydrochloride of the object compound was prepared by an ordinary method, thereby obtaining about 0.2 g of a creamy crystal.

molecular formula; $C_{24}H_{30}N_2O_3 \cdot 2HCl$, $^1$H—NMR(CDCl$_3$) δ; 1.12~3.4 (9H, m), 2.72~3.00 (2H, m), 3.48 (2H, s), 3.62 (2H, t), 3.95 (6H, s), 4.26 (2H, s), 6.90 (1H, s), 7.28 (6H, s),

EXAMPLE 7

4-[N-(o-Aminobenzyl)ethyl]-1-benzylpiperidine

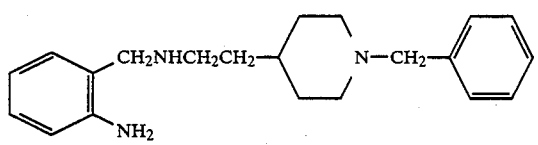

30 g of 2-nitrobenzaldehyde, 21.4 g of 1-benzyl-4-aminoethylpiperidine, and 100 ml of methanol were stirred in a nitrogen stream at room temperature for 3 hr. The resulting reaction mixture was cooled with ice, and a solution of 16 g of sodium borohydride in 30 ml of MeOH was dropwise added thereto. The reaction was allowed to proceed at room temperature for an additional 1 hr. The reaction mixture was poured into water, extracted with methyl chloride, extracted three times with 150 ml of 10% hydrochloric acid, and washed with methylene chloride. Sodium carbonate was added to the water phase to adjust a pH value to 10, followed by extraction with methylene chloride. The extract was dried over anhydrous magnesium sulfate, and the solvent was distilled off in vacuo, thereby preparing 28.4 g of 1-benzyl-4-[N-(o-nitrobenzyl)ethyl]piperidine.

This compound was dissolved in 100 ml of methanol and hydrogenated in the presence of 3 g of 10% palladium-carbon (hydrous) at a pressure of 4 kg/cm$^2$, thereby preparing 25.6 of the title compound.

molecular formula; $C_{21}H_{29}N_3$, $^1$H—NMR(CDCl$_3$) δ; 1.0~2.1 (9H, m), 2.64 (2H, t), 2.90 (2H, m), 3.47 (2H, s), 6.65 (2H, m), 7.02 (2H, m), 7.30 (5H, s),

EXAMPLE 8

3-[2-(1-Benzyl-4-piperidyl)ethyl-2-(1H,3H)-quinazolinone

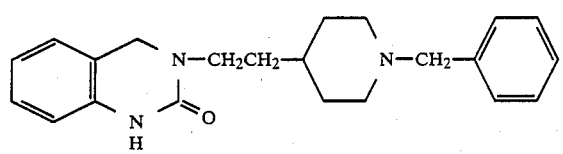

25.6 g of 4-[N-(o-aminobenzyl)ethyl]-1-benzyl-piperidine, 15 g of 1,1'-carbonyldiimidazole, and 100 ml of methanol were heated under reflux for 12 hr. After the completion of the reaction, the reaction mixture was poured into water, extracted with methylene chloride and dried over magnesium sulfate. The solvent was distilled off in vacuo therefrom.

The residue was purified by silica gel column chromatography (5% MeOH—CH$_2$Cl$_2$) and recrystallized twice from ethyl acetate, thereby preparing 3.0 g the title compound.

molecular formula; $C_{22}H_{27}N_3O$, $^1$H—NMR(CDCl$_3$) δ; 1.0~2.1 (9H, m), 2.7~3.0 (2H, m), 3.2~3.6 (4H, m), 4.4 (2H, s), 6.5~7.4 (8H, m), 7.75 (1H, s),

EXAMPLE 9

1-[4'-(1'-Benzylpiperidine)ethyl-1,2,3,4-tetrahydro-4-methyl-5H-[1,4]-benzodiazepin-2-one dihydrochloride

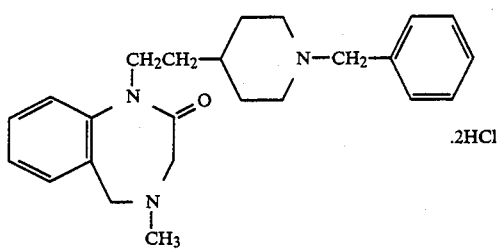

.2HCl 0.35 g of sodium hydride was suspended in 0.5 ml of dimethylformamide (DMF). The suspension was stirred while cooling it with ice, and 0.52 g of 1,2,3,4-tetrahydro-4-methyl-5H-[1,4]-benzodiazepin-2-one dissolved in 3 ml of DMF was dropwise added thereto, followed by stirring at room temperature for 30 min. 0.81 g of N-benzyl-4-(2-chloromethyl)piperidine hydrochloride dissolved in 3 ml of DMF was dropwise added thereto, and the mixture was stirred at 60 to 70° C. for 7 hr. The reaction mixture was poured into ice/water and extracted with methylene chloride. The extract was washed with a saturated saline solution and dried over magnesium sulfate. The solvent was distilled off in vacuo. The residue was purified by silica gel column chromatography. A hydrochloride of the purified product was prepared by an ordinary method. Thus there was obtained 0.17 g of a pale yellow amorphous substance (yield: 13.5%).

molecular formula; $C_{24}H_{31}N_3O \cdot 2HCl$, $^1H$—NMR(CDCl$_3$) δ; 1.25~2.02 (9H, m), 2.52 (3H, s), 2.79~2.95 (2H, bd), 3.10 (2H, s), 3.48 (2H, s), 3.54 (2H, s), 3.91 (2H, bt), 7.14~7.45 (9H, m),

EXAMPLE 10

1-[4'-(1'-Benzylpiperidine)ethyl]-1,2,3,4-tetrahydro-5H-1-benzazepin-2-one hydrochloride

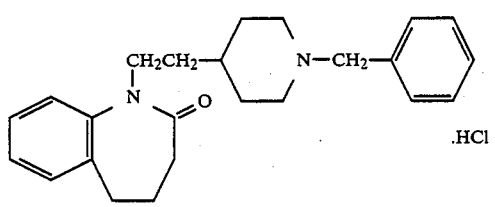

.HCl 0.27 g of sodium hydride was suspended in 0.5 ml of dimethylformamide (DMF). The suspension was stirred while cooling it with ice. 0.60 g of 1,2,3,4-tetrahydro-5H-1-benzazepin-2-one dissolved in 4 ml of DMF was dropwise added thereto. The mixture was heated at 60° C. for 15 min and then cooled with ice 1.02 g of N-benzyl-4-(2-chloromethyl)piperidine hydrochloride was added thereto, and the mixture was stirred at 60° C. for 3.5 Hr. The reaction mixture was left to stand for cooling, poured into ice/water, and extracted with methylene chloride. The extract was washed with water and dried over magnesium sulfate. The solvent was distilled off in vacuo. The residue was purified by silica gel column chromatography. A hydrochloride of the purified product was prepared by an ordinary method. Thus there was obtained 1.40 g of the title compound (yield: 94.8%).

molecular formula; $C_{24}H_{30}N_2O \cdot HCl$, $^1H$—NMR(CDCl$_3$) δ; 1.20~1.92 (11H, m), 2.20~2.24 (4H, bs), 2.60~2.88 (4H, m), 3.44 (2H, s), 7.12~7.24 (9H, m),

EXAMPLE 11

N-[4-(1'-Benzylpiperidyl)ethyl]-5,6,11,12-tetrahydrodibenzo[b,f]azocin-6-one hydrochloride

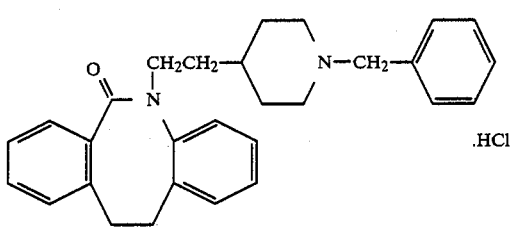

.HCl 2.24 g of 5,6,11,12-tetrahydrobenzo[b,f]azocin-6-one and 60% sodium hydride were added to 20 ml of dimethylformamide. The mixture was stirred at 60° C. for 1 hr, and 0.7 g of 1-benzyl-4-chloroethylpiperidine was added thereto, followed by the reaction for an additional 3.5 hr.

The reaction mixture was poured into 20 ml of water, extracted with ethyl acetate, washed with a saturated saline solution, and dried over magnesium sulfate. The solvent was distilled off therefrom in vacuo.

The residue was purified by silica gel column chromatography (5% MeOH in CH$_2$Cl$_2$), thereby preparing 0.6 g of the title compound.

molecular formula; $C_{29}H_{32}N_2O \cdot HCl$, $^1H$—NMR(CDCl$_3$) δ; 1.1~2.2 (9H, m), 3.7~4.1 (4H, m), 4.15~4.5 (2H, m), 4.46 (2H, s), 6.8~7.4 (13H, m)

EXAMPLE 12

10-[4'-(1'-Benzylpiperidine)ethyl]-10,11-dihydro-5-methyl-5H-dibenzo[b,e][1,4]diazepin-11-one hydrochloride

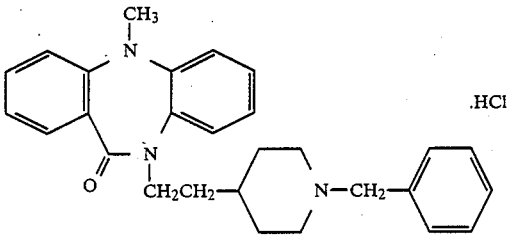

.HCl 0.25 g of sodium hydride was suspended in dimethylformamide (DMF). The suspension was stirred while cooling it with ice. 0.58 g of 10,11-dihydro-5-methyl-5H-dibenzo[b,e][1,4]diazepin-11one dissolved in 5 ml of DMF was dropwise added thereto. The mixture was stirred at 40° to 50° C. for 20 min and then cooled with ice. 0.71 g of 4-(aminoethyl)-1-benzylpiperidine was added thereto, and the mixture was stirred at 45° to 55°

C. for 6 hr. The reaction mixture was poured into ice-/water and extracted with methylene chloride. The organic phase was washed with a saturated saline solution and dried over magnesium sulfate. The solvent was distilled off in vacuo. The residue was purified by silica gel column chromatography. A hydrochloride of the purified product was prepared by an ordinary method. Thus there was obtained 0.78 g of a pale yellow amorphous substance (yield: 65.4%).

|  | C | H | N |
|---|---|---|---|
| calculated (%) | 60.58 | 7.07 | 12.29 |
| found (%) | 60.54 | 7.00 | 12.29 |

EXAMPLE 14

N-[4'-(1'-(p-Hydroxybenzyl)piperidine)ethyl]-2-quinoxalinecarboxylic amide hydrochloride

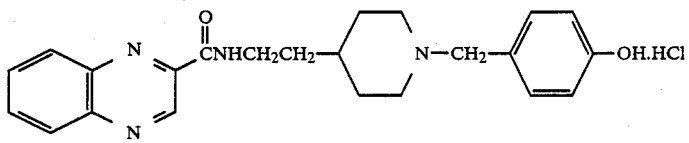

molecular formula; $C_{28}H_{31}N_3O \cdot HCl$
$^1H$—NMR(CDCl$_3$) δ; 1.20~1.91 (11H, m) 2.60~3.00 (2H, bs), 3.22 (3H, s), 3.41 (2H, s), 6.87~7.08 (3H, m), 7.08 (9H, m), 7.64 (1H, dd)

EXAMPLE 13

Isopropyl 3-[[4'-(1'-benzylpiperidine)propionyl]amino]-2-pyrazinecarboxylate hydrochloride

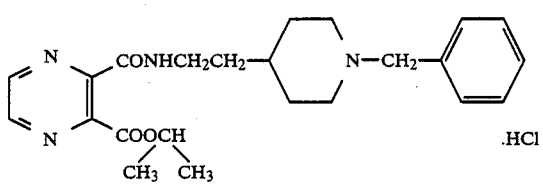

18 g of 2,3-pyrazinecarboxylic anhydride was added to 200 ml of isopropyl alcohol, and the mixture was refluxed for 1 hr. Thereafter, the alcohol was distilled off therefrom. The resulting solid was dissolved in THF, and 30.6 g of 4-(2-aminoethyl)-benzylpiperidine and 21 g of 1-hydroxybenzotriazole were added thereto. The mixture was stirred while cooling, and 29.7 g of DCC was added to the mixture, followed by a reaction at room temperature overnight. The reaction mixture was filtered and THF was distilled off from the filtrate, followed by addition of methylene chloride. The mixture was washed with an aqueous saturated potassium carbonate solution and then with a saline solution and dried. The solvent was distilled off therefrom. The residue was purified by making use of a silica gel column. The resulting crystal was recrystallized from ether-hexane, thereby preparing 8.81 g of a white crystal of the object compound. A hydrochloride of the compound was prepared by an ordinary method.
elementary analysis: $C_{23}H_{30}N_4O_3 \cdot HCl \cdot \frac{1}{2}H_2O$, 2 g of 2-quinoxalinecarboxylic acid chloride was reacted with 2.52 g of 1-(p-methoxybenzyl)-4-piperidineethylamine in the presence of 2 g of triethylamine in THF at room temperature. The reaction mixture was post-treated by an ordinary method and purified by column chromatography, thereby preparing 2.5 g of N-[4'-(1'-(p-methoxybenzyl)piperidine)ethyl]-2-quinoxalinecarboxylic amide.

This compound was dissolved in 1 g of methylene chloride and reacted with BBr$_3$ for demethylation. The product was purified by column chromatography, thereby preparing 0.3 g of a product. A hydrochloride of the product was prepared to obtain 0.2 g of a creamy crystal.
molecular formula; $C_{23}H_{26}N_4O_2 \cdot HCl$
$^1H$—NMR(CDCl$_3$) δ; 1.08~1.92 (9H, m, 2.84~3.18 (2H, m), 3.24~3.64 (2H, m), 3.52 (2H, s), 6.60 (2H, d), 7.05 (2H, d), 7.17 (2H, s), 7.64~8.14 (4H, m), 9.53 (1H, m)

EXAMPLE 15

N-[4'-(1'-Benzylpiperidyl)ethyl]-2-quinoxalinecarboxylic amide

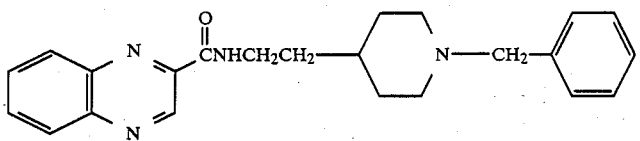

40 q of 2-quinoxaloyl chloride was added to a mixture of 4.6 g of 1-benzyl-4-aminoethylpiperidine, 50 ml of pyridine, and 4-dimethylaminopyridine while stirring the mixture at room temperature, followed by a reaction for 3 hr. Thereafter, the reaction mixture was poured into water, extracted with methylene chloride, and dried over anhydrous magnesium sulfate. The solvent was distilled off therefrom.

The residue was purified by silica gel chromatography (5% MeOH-CH$_2$Cl$_2$) and recrystallized from ethyl acetate, thereby preparing 3.0 g of the title compound.
molecular formula; $C_{23}H_{26}N_4O_2 \cdot HCl$
$^1H$—NMR(CDCl$_3$) δ; 1.16~2.20 (9H, m), 2.76~3.04 (2H, m), 3.49 (2H, s), 3.48~3.68 (2H, t), 7.13~7.40 (5H, m), 7.70~8.26 (4H, m), 9.64 (1H, s)

EXAMPLE 16

1-Benzyl-4-(N'-phenylaminoethyl)piperidine

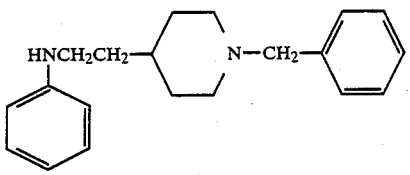

47 g of 4-(N-benzoylpiperidyl) acetate, 8 ml of thionyl chloride, and 20 ml of benzene were heated under reflux for 2 hr. Thereafter, the solvent was distilled off in vacuo.

The residue was dissolved in 20 ml of THF. The resulting solution was dropwise added to a mixture of 1.86 g of aniline, 10 g of triethylamine, and 30 ml of THF while cooling the mixture with ice and, at the same time, stirring the mixture, followed by a reaction at room temperature for about 11 hr. The reaction mixture was poured into water and extracted with methylene chloride. The extract was washed with a saturated saline solution and dried over magnesium sulfate. The solvent was distilled off in vacuo. The residue was purified by silica gel chromatography (5% MeOH in $CH_2Cl_2$) to prepare 0.9 g of 4-(N-benzoylpiperidyl)acetanilide.

0.9 of 4-(N-benzoylpiperidyl)acetanilide was dissolved in 10 ml of THF. A solution of 0.38 g of lithium aluminum hydride in 30 ml of THF was dropwise added to the resulting solution while cooling and stirring the solution. The mixture was heated under reflux for additional 1 hr. After the completion of the reaction, water was added thereto. The resulting precipitate was removed by filtration. The filtrate was extracted with ethyl acetate, washed with a saturated saline solution, and dried over anhydrous magnesium sulfate. The solvent was distilled off in vacuo to prepare 0.7 of 1-benzyl-4-(N'-phenylaminoethyl)piperidine.

molecular formula; $C_{20}H_{26}N_2$ $^1H$—NMR($CDCl_3$) δ; 1.0~2.2 (9H, m), 2.85 (2H, m), 3.10 (2H, t), 3.44 (2H, s), 3.7 (1H, bs), 6.4~6.8 (3H, m), 7.0~7.4 (7H, m),

EXAMPLE 17

N-[4'-(1'-Benzylpiperidyl)ethyl]acetanilide

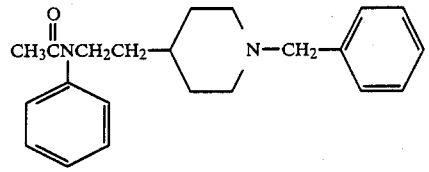

0.4 g of acetyl chloride was dropwise added to a mixture of 0.7 g of 1-benzyl-4-(N'-phenylaminoethyl)piperidine, 2.0 g of triethylamine, and 20 ml of THF while cooling the mixture with ice under stirring.

The reaction was allowed to proceed at room temperature for 3 hr, and 20 ml of water was added thereto, followed by extraction with methylene chloride. The extract was washed with a saturated saline solution and dried over anhydrous magnesium sulfate. The solvent was distilled off therefrom in vacuo. The residue was purified by column chromatography (5% MeOH in $CH_2Cl_2$), thereby preparing the title compound.

molecular formula; $C_{23}H_{28}N_2O$, $^1H$—NMR($CDCl_3$) δ; 1.0~2.1 (12H, m), 2.6~3.0 (2H, m), 3.39 (2H, s), 3.67 (2H, t), 6.9~7.5 (10H, m),

EXAMPLE 18

N-(3'5'-Dimethoxyphenyl)-N-[4'-(1'--benzylpiperidyl)-ethyl]-4-fluorocinnamamide hydrichloride

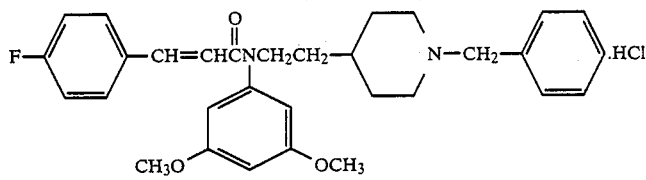

0.51 g of p-fluorocinnamoyl chloride was added to a mixture of 1.0 g of 1-benzyl-4-[N'-(3'5'-dimethoxyphenyl)aminoethyl]piperidine, 2.0 g of triethylamine, and 20 ml of THF while cooling the mixture with ice under stirring. The reaction was allowed to proceed at room temperature for 2 hr. Thereafter the reaction mixture was poured into water, extracted with ethyl acetate, washed with a saturated saline solution, and dried over anhydrous magnesium sulfate. The solvent was distilled off therefrom in vacuo.

The residue was purified by silica gel chromatography (5% MeOH in $CH_2Cl_2$). A hydrochloride of the product was prepared by an ordinary method, thereby obtaining 0.9 g of the title compound.

molecular formula; $C_{31}H_{35}N_2O_3F \cdot HCl$, $^1H$—NMR($CDCl_3$) δ; 1.1~2.1 (9H, m), 2.7~3.0 (2H, bd), 3.51 (2H, s), 3.83 (8H, m), 6.1~6.4 (4H, m), 6.9~7.8 (10H, m)

EXAMPLE 19

N-[4'-(1'-Benzylpiperidine)ethyl]-N-phenylnicotinamid dihydrochloride

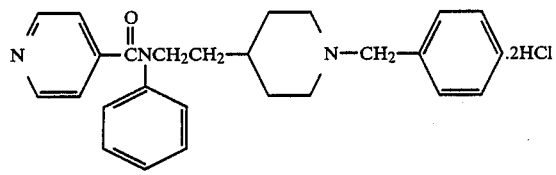

0.70 g of N-[4'-(1'-benzylpiperdine)ethyl]-aniline and a catalytic amount of 4-(N,N-dimethylamino)pyridine were dissolved in 30 ml of pyridine. The resulting solution was stirred while cooling it with ice. 0.85 of isonicotinoyl chloride was added thereto, followed by stirring for 3.5 hr. The solvent was distilled off in vacuo. The residue was purified by making use of a silica gel column. A dihydrochloride of the purified product was prepared by an ordinary method. Thus there was obtained 0.75 g of a pale yellow amorphous substance (yield: 73.0%).

molecular formula; $C_{26}H_{29}N_3O.2HCl$, $^1H-NMR(CDCl_3)$ δ; 1.13~2.01 (9H, m), 2.81 (2H, bd), 3.44 (2H, s), 3.88 (2H, bt), 6.84~7.26 (12H, m), 8.31 (2H, d)

EXAMPLE 20

4-(1-Benzylpiperidine)propanailide hydrochloride

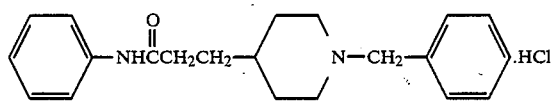

0.5 g of aniline and 1 g of triethylamine were dissolved in THF. 1 g of 4-(1-benzylpiperidine)propionyl chloride was dropwise added to the resulting solution while stirring the solution, followed by a reaction at room temperature for 5 hr. Thereafter the solvent was distilled off and methylene chloride was added to the residue. The resulting solution was washed with water and dried over MgSo4. The solvent was again distilled off and the residue was purified by making use of a silica gel column, thereby preparing the object compound in the form of oleaginous matter. A chloride of this compound was prepared by an ordinary method, thereby obtaining 0.14 g of a white crystal.

m.p. (°C.): 197.5°–198° C.,

Elementary analysis: $C_{21}H_{26}N_2C.HCl$,

|  | C | H | N |
|---|---|---|---|
| calculated (%) | 70.28 | 7.58 | 7.81 |
| found (%) | 70.50 | 7.58 | 7.83 |

EXAMPLE 21

N-[3'-(1'-Benzylpyrrolidine)methyl]benzamide hydrochloride

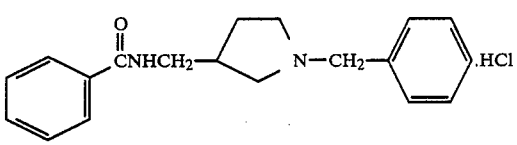

0.74 g of benzyl chloride was reacted with 1 g of 3-(2'-aminomethyl)benzylpyrrolidine in the presence of 1.5 g of triethylamine in THF at room temperature while stirring the reaction system. The reaction mixture was post-treated by an ordinary method and purified by column chromatography, thereby preparing 0.32 g of the object compound. A hydrochloride of the compound was prepared by an ordinary method.

molecular formula; $C_{19}H_{22}N_2O.HCl$, $^1H-NMR(CDCl_3)$δ; 1.48~3.08(7H,m), 3.44(2H,d), 3.62(2H,d), 7.04~7.88(10H,m).

EXAMPLE 22

4-[4'-(N-Benzyl)piperidyl]-3-hydroxy-p-methoxybutyrophenone 2 ml of diisopropylamine was added to 7 ml of THF in a nitrogen stream. 7.6 ml of a 1.6M solution of n-butyllithium in hexane was added thereto at 0° C. The mixture was stirred for 10 min and then cooled to −78° C. A solution of 1.65 g of p-methoxyacetophenone in 10 ml of THF was added thereto, and the mixture was stirred for 20 min. Further, a solution of 2.4 g of 1-benzyl-4-piperidinecarboaldehyde in 10 ml of THF was added thereto, and the mixture was stirred for 10 min. An aqueous 1% ammonium chloride solution was added to the reaction mixture, followed by extraction with methylene chloride. The extract was washed with a saturated saline solution and dried over anhydrous magnesium sulfate. The solvent was distilled off in vacuo. The residue was purified by silica gel column chromatography (5% MeOH—CH2Cl2), thereby preparing 2.0 g of the title compound.

molecular formula; $C_{23}H_{29}NO_3$, $^1H-NMR(CDCl_3)$δ; 1.0~2.2(9H,m), 2.6 ~3.4(5H,m), 3.43(2H,s), 3.81(3H,s), 4.1(1H), 6.83(2H,d), 7.17(5H,s), 7.82(2H,d).

EXAMPLE 23

4-[4'-N-Benzyl)piperidyl]-p-methoxybutyrophenone hydrochloride

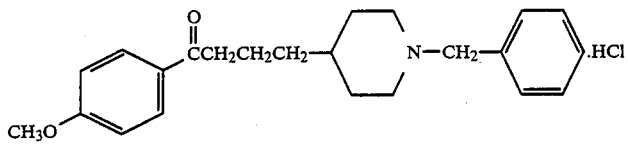

0.54 g of 4-[4'-(N-benzyl)piperidyl]-3-hydroxy-p-methoxybutyrophenone, 0.1 g of p-toluenesulfonic acid, and 30 ml of toluene were heated under reflux for 5 hr by making use of a Dean-Stark reflux condenser. After the completion of the reaction, the reaction mixture was poured into an aqueous potassium carbonate solution, extracted with methylene chloride, and dried over anhydrous magnesium sulfate. The solvent was distilled off in vacuo. The residue was purified by column chromatography (5% MeOH—CH$_2$Cl$_2$) to prepare 0.45 g of 1-benzyl-4-[4-(p-methoxyphenyl)-4-oxobytyl]piperidine. This compound was dissolved in 20 ml of MeOH and 40 g of 10% palladium-carbon (anhydrous) was added thereto to effect hydrogenation at room temperature under atmospheric pressure for 1.5 hr. The insolubles were filtered off, and the solvent was distilled off in vacuo. A hydrochloride of the product was prepared by an ordinary method. The hydrochloride was recrystallized from MeOH-IPE, thereby preparing 0.2 g of the title compound.

molecular formula; $C_{22}H_{29}NO_2 \cdot HCl$, $^1$H-NMR(CDCl$_3$)δ; 1.4~2.3(11H,m), 2.4~2.7(2H,m), 2.95(2H,t), 3.55(2H,s), 3.87(3H,s), 6.93(2H,d), 7.1~7.5(5H,m), 7.94(2H,d).

EXAMPLE 24

N-[4'-(1'-Benzylpiperidine)ethyl]-3-furancarboxylic amide hydrochloride

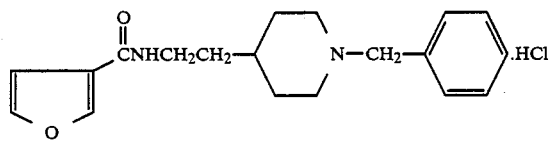

1.64 g of 4-(2-aminoethyl)-1-benzylpiperidine and 2.67 g of potassium carbonate were added to a mixture comprising 40 ml of chloroform and 40 ml of water. The mixture was stirred for 1 hr while cooling it with ice. The organic phase was separated, washed with a saturated saline solution, and dried over magnesium sulfate. The solvent was distilled off in vacuo and the residue was purified by making use of a silica gel column. A hydrochloride of the product was prepared by an ordinary method, thereby obtaining 1.60 g of the title compound in the form of a pale yellow amorphous substance (yield: 61.1%).

molecular formula; $C_{19}H_{24}N_2O_2 \cdot HCl$, $^1$H-NMR(CDCl$_3$)δ; 1.47~2.10(9H,m), 2.81(2H,bd), 3.25~3.47(4H,m), 5.80(1H,bs), 6.51(1H,dd), 7.15~7.19(6H,m), 7.82(1H,dd).

EXAMPLE 25

N-[4'-Benzylpiperidine)ethyl]benzamide

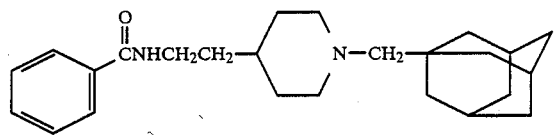

1.47 g of N-(1-adamantanemethyl)-4-(2-aminoethyl)-piperidine and 0.73 g of potassium carbonate were added to a mixture comprising 15 ml of chloroform and 15 ml of water. The mixture was vigorously stirred while cooling it with ice. 0.90 g of benzoyl chloride was added to the mixture, followed by stirring at room temperature overnight. The organic phase was separated, washed with water and a saturated saline solution, and dried over magnesium sulfate. The solvent was distilled off in vacuo. The residue was purified by making use of a silica gel column. The purified product was recrystallized from benzene-n-hexane, thereby preparing 1.47 g of the title compound in the form of a pale yellow plate crystal (yield: 72.6%).

molecular formula; $C_{25}H_{36}N_2O$, $^1$H-NMR(CDCl$_3$)δ; 1.29~2.28(27H,m), 2.72(2H,bs), 3.43(2H,q), 6.01(1H,bs), 7.31~7.43(3H,m), 7.67(1H,dd).

EXAMPLE 26

N-Methyl-N-[4'-(1'-benzylpiperidine)ethyl]benzamide hydrochloride

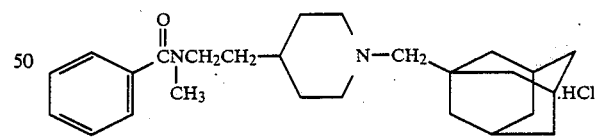

0.18 g of sodium hydride was suspended in 2 ml of tetrahydrofuran (THF). The suspension was stirred while cooling it with ice. A solution of 1.45 g of N-[4'-1'-benzylpiperidine)ethyl]benzamide dissolved in 5 ml of THF was dropwise added thereto. The mixture was stirred at room temperature for 1 hr and again cooled with ice. 0.36 ml of methyl iodide was added thereto, followed by stirring at room temperature overnight. The reaction mixture was poured into ice/water, extracted with chloroform while conducting salting out, washed with a saturated saline solution, and dried over magnesium sulfate. The solvent was distilled off in vacuo and the residue was purified by silica gel chromatography. Thus there was prepared 0.60 g yellow oleaginous matter (yield: 47.0%).

The starting material (0.22 g) remaining unmethylated was recovered (recovery: 15.2%). A hydrochloride of the obtained oleaginous matter was prepared by an ordinary method, thereby obtaining 0.52 g of the title compound in the form of a yellow amorphous substance (yield: 37.6%).

molecular formula; $C_{26}H_{38}N_2O \cdot HCl$, $^1$H-NMR(CDCl$_3$)$\delta$; 0.92~3.60(63H,m), 7.29(5H,s).

EXAMPLE 27

N-[4'-(1'-Cyclohexylmethylpiperidyl)ethyl]-N-methyl-benzamide hydrochloride

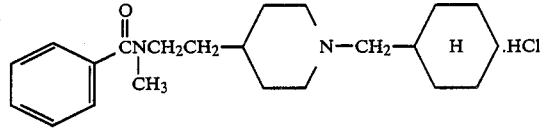

0.6 g of N-methyl-N-(4'-piperidylethyl)benzamide, 1.2 g of cyclohexyl bromide, 2.0 g of sodium bicarbonate, and 30 ml of methyl ethyl ketone were heated under reflux for 7 hr. After the completion of the reaction, water was added to the reaction mixture, followed by extraction with ethyl acetate. The extract was washed with a saturated saline solution and dried over anhydrous magnesium sulfate. The solvent was distilled off in vacuo. The residue was purified by silica gel chromatography (5% MeOH—CH$_2$Cl$_2$), thereby preparing 0.3 g of the title compound.

molecular formula; $C_{22}H_{34}N_2O \cdot HCl$ $^1$H-NMR(CDCl$_3$)$\delta$; 0.8~1.1(20H,m), 1.1~1.6(4H,m), 1.8~2.6(5H,m), 7.4(5H,s).

EXAMPLES 28 to 177

The compounds synthesized in the same manner as that of the Examples 1 to 27 are shown in Tables 4 to 8.

TABLE 4

| Ex. No. | Structural formula | Physicochemical constant (m.p., elem. anal., NMR, etc.) |
|---|---|---|
| 28 | (3,4-dimethoxy indanone with 1-benzylpiperidin-4-yl substituent)·HCl | m.p. (°C); 247~248 (dec.)<br>elem. anal.: C$_{23}$H$_{27}$NO$_3$·HCl<br>　　　　C　　H　　N<br>calcd. (%) 68.73 7.02 3.48<br>found (%) 68.70 6.99 3.35 |
| 29 | (indanone with 1-benzylpiperidin-4-ylmethyl substituent)·HCl | m.p. (°C); 196~197<br>elem. anal.: C$_{22}$H$_{25}$NO·HCl<br>　　　　C　　H　　N<br>calcd. (%) 74.24 7.36 3.94<br>found (%) 74.25 7.56 3.80 |
| 30 | (6-methoxy indanone with 1-benzylpiperidin-4-ylmethyl substituent)·HCl | m.p. (°C); 203~204 (dec.)<br>elem. anal.: C$_{23}$H$_{27}$NO$_2$·HCl<br>　　　　C　　H　　N<br>calcd. (%) 71.58 7.31 3.63<br>found (%) 71.58 7.25 3.65 |
| 31 | (5,6-dimethoxy indanone with 1-benzylpiperidin-4-ylmethyl substituent)·HCl | $^1$H—NMR(CDCl$_3$)δ;<br>1.10~3.40(14H,m)3.48(2h,s), 3.81(3H,s),<br>3.85(3H,s), 3.85(3H,s), 6.25(1H,bs),<br>6.42(1H,bs),7.25(5H,s)<br>mol. form.; C$_{24}$H$_{29}$NO$_3$·HCl |
| 32 | (4,7-dimethoxy indanone with 1-benzylpiperidin-4-ylmethyl substituent)·HCl | $^1$H—NMR(CDCl$_3$)δ;<br>1.05~3.40(14H,m), 3.45(2H,s), 3.80(3H,s),<br>3.85(3H,s), 6.75(2H,ABq), 7.22(5H,s)<br>mol. form.; C$_{24}$H$_{29}$NO$_3$·HCl |
| 33 | (5,6-dimethoxy indanone with 1-benzylpiperidin-4-ylethyl substituent)·HCl | m.p. (°C); 201~202 (dec.)<br>elem. anal.: C$_{25}$H$_{31}$NO$_3$·HCl<br>　　　　C　　H　　N<br>calcd. (%) 69.83 7.50 3.26<br>found (%) 69.13 7.42 3.31<br>1/5H$_2$O (%) 69.25 7.53 3.23 |

TABLE 4-continued

| Ex. No. | Structural formula | Physicochemical constant (m.p., elem. anal., NMR, etc.) |
|---|---|---|
| 34 | (indanone with 3,4-dimethoxy, 2-substituted with piperidine-N-CH2-phenyl, OH on piperidine) | $^1$H—NMR(CDCl$_3$)δ; 1.10~3.40(11H,m), 3.50(2H,s), 3.85(3H,s), 3.93(3H,s), 4.25(1H,bs), 6.81(1H,s), 7.07(1H,s), 7.22(5H,s) mol. form.; C$_{23}$H$_{27}$NO$_4$ |
| 35 | (indanone with 3,4-dimethoxy, 2-ylidene-piperidine-N-CH2-phenyl)·HCl | m.p. (°C); 225~226 (dec.) elem. anal.: C$_{23}$H$_{25}$NO$_3$·HCl <br>     C    H    N <br> calcd. (%) 69.08 6.55 3.50 <br> found (%) 68.78 6.43 3.50 |
| 36 | (indanone 2-ylidene-piperidine-N-CH2-phenyl)·HCl | m.p. (°C); 169~170 (dec.) elem. anal.: C$_{22}$H$_{23}$NO·HCl <br>     C    H    N <br> calcd. (%) 74.67 6.84 3.96 <br> found (%) 74.42 6.61 3.76 |
| 37 | (6-methoxyindanone 2-(piperidin-4-ylmethylene)-N-CH2-phenyl)·HCl | m.p. (°C); 120~122 elem. anal.: C$_{23}$H$_{25}$NO$_2$·HCl <br>     C    H    N <br> calcd. (%) 71.96 6.83 3.65 <br> found (%) 71.84 6.85 3.46 |
| 38 | (4,6-dimethoxyindanone 2-(piperidin-4-ylmethylene)-N-CH2-phenyl)·HCl | $^1$H—NMR(CDCl$_3$)δ; 1.40~2.40(7H,m), 2.90(2H,bd), 3.48(2H,s), 3.51(2H,bd), 3.82(3H,s), 3.86(3H,s), 6.30 (1H,bd), 6.43(1H,bd), 6.50(1H,bt), 7.23(5H,s) mol. form.; C$_{24}$H$_{27}$NO$_3$·HCl |
| 39 | (4,7-dimethoxyindanone 2-(piperidin-4-ylmethylene)-N-CH2-phenyl)·HCl | $^1$H—NMR(CDCl$_3$)δ; 1.40~2.50(7H,m), 2.86(2H,bd), 3.50(4H,s), 3.90(3H,s), 3.94(3H,s), 6.59(1H,dt), 6.78(2H,ABq), 7.22(5H,s) mol. form.; C$_{24}$H$_{27}$NO$_3$·HCl |

TABLE 4-continued

| Ex. No. | Structural formula | Physicochemical constant (m.p, elem. anal., NMR, etc.) |
|---|---|---|
| 40 | [Structure: dimethoxy indanol with OH, CH₂ linker to piperidine N-CH₂-phenyl · HO₂CCH=CHCO₂H] | ¹H—NMR(CDCl₃)δ; 1.14~2.04(14H,m), 3.49(2H,s), 3.81(6H,s), 4.77(3H,dd), 6.65(1H,d), 6.82(1H,d), 7.23(5H,s) mol. form.; C₂₄H₃₁NO₃·C₄H₄O₄ |
| 41 | [Structure: dimethoxy indanone with CH₂ linker to piperidine N-CH₂-phenyl · HCl] | ¹H—NMR(CDCl₃)δ; 1.10~2.32(9H,m), 2.90(2H,bd), 3.52(4H,s), 3.89(3H,s), 3.93(3H,s), 6.71(1H,tt), 6.84(1H,s), 7.20(1H,s), 7.24(5H,s) mol. form.; C₂₅H₂₉NO₃·HCl |
| 42 | [Structure: phenyl-C(=O)-CH₂CH₂CH₂-piperidine-N-CH₂-phenyl · HCl] | m.p. (°C); 149~150 elem. anal.: C₂₂H₂₇NO·HCl<br>  C    H    N<br>calcd. (%)  73.83  7.88  3.91<br>found (%)   71.29  8.00  3.80<br>7/10H₂O (%) 71.31  8.00  3.78 |
| 43 | [Structure: phenyl-CH(OH)-CH₂CH₂CH₂-piperidine-N-CH₂-phenyl · HCl] | ¹H—NMR(CDCl₃)δ; 1.80~2.03(13H,m), 2.80(3H,bd), 3.43(2H,s), 4.60(1H,t), 7.28(5H,s), 7.30(5H,s) mol. form.; C₂₂H₂₉NO·HCl |
| 44 | [Structure: phenyl-CH(OH)-CH=CHCH₂-piperidine-N-CH₂-phenyl · HCl] | ¹H—NMR(CDCl₃)δ; 1.10~2.13(7H,m), 2.26(2H,t), 2.88(2H,bd), 3.48(2H,s), 6.72~7.07(2H,m), 7.30(5H,s), 7.10~8.00(5H,m) mol. form.; C₂₂H₂₅NO·HCl |
| 45 | [Structure: pyridyl-CH(OH)-CCH₂CH₂CH₂-piperidine-N-CH₂-phenyl · 2HCl] | m.p. (°C); 176~178 elem. anal.: C₂₁H₂₆N₂O·2HCl<br>  C    H    N<br>calcd. (%)  63.80  7.14  7.09<br>found (%)   63.13  7.43  6.88<br>3/10H₂O (%) 62.94  7.19  6.99 |
| 46 | [Structure: pyridyl-C(OH)(OH)CHCH₂-piperidine-N-CH₂-phenyl] | ¹H—NMR(CDCl₃)δ; 1.05~2.15(9H,m), 2.85(2H,bd), 3.02(2H,d), 3.25(1H,bs), 3.47(2H,s), 4.10~4.45(1H,m), 7.21(5H,s), 7.62(2H,dd), 8.70(2H,dd) mol. form.; C₂₁H₂₆N₂O₂ |

TABLE 4-continued

| Ex. No. | Structural formula | Physicochemical constant (m.p., elem. anal., NMR, etc.) |
|---|---|---|
| 47 | pyridine-CH=CHCH₂-C(O)-piperidine-N-CH₂-phenyl · 2HCl | ¹H—NMR(CDCl₃)δ;<br>1.10~2.10(7H,m), 2.25(2H,bd), 2.85(2H,bd), 3.45(2H,bs), 6.59~7.10(2H,m), 7.20(5H,s), 7.56(2H,dd), 8.67(2H,dd)<br>mol. form.; C₂₁H₂₄N₂O.2HCl |
| 48 | pyridine-NHCCH₂CH₂-C(O)-piperidine-N-CH₂-phenyl · 2HCl | m.p. (°C.); 240~240.7<br>elem. anal.: C₂₀H₂₅N₃O.2HCl<br>            C      H      N<br>calcd. (%)  66.75  7.28  11.68<br>found (%)   66.26  7.42  11.37<br>3/20H₂O (%) 66.25  7.31  11.59 |
| 49 | pyridine-NHCCH₂-C(O)-piperidine-N-C(O)-phenyl · HCl | ¹H—NMR(CDCl₃)δ;<br>1.80~2.24(9H,m), 2.96(2H,d), 3.64(1H,m), 4.60(1H,m), 7.20~7.58(6H,m), 8.34(2H,d)<br>mol. form.; C₁₉H₂₁N₃O₂.HCl |
| 50 | O₂N-phenyl-NHCCH₂-C(O)-piperidine-N-CH₂-phenyl · HCl | ¹H—NMR(CDCl₃)δ;<br>1.12~2.20(7H,m), 2.34(2H,d), 2.74~3.01(2H, m), 3.50(2H,s), 7.29(2H,s), 7.71(2H,d), 8.20(2H,d) |

TABLE 5

| Ex. No. | Structural formula | Physicochemical constant (m.p., elem. anal., NMR, etc.) |
|---|---|---|
| 51 | (quinazolinone)-N-CH₂CH₂-(piperidine)-N-CH₂-(phenyl) · 2HCl | m.p. (°C.); 135~140 (dec.)<br>elem. anal.: $C_{22}H_{25}N_3O \cdot 2HCl$<br>        C    H    N<br>calcd. (%)  62.86 6.47 10.00<br>found (%)  59.22 6.63 9.14<br>$3/2 H_2O$ (%) 59.06 6.76 9.39 |
| 52 | (dihydroquinazolinone)-N-CH₂CH₂-(piperidine)-N-CH₂-(phenyl) · 2HCl | m.p. (°C.); 80~82 (dec.)<br>elem. anal.: $C_{22}H_{27}N_3O \cdot 2HCl$<br>        C    H    N<br>calcd. (%)  62.56 6.92 9.95<br>found (%)  60.14 7.313 9.21<br>$1 \cdot H_2O$ (%) 60.00 7.09 9.54 |
| 53 | (isoquinolinone)-N-CH₂CH₂-(piperidine)-N-CH₂-(phenyl) · HCl | $^1H-NMR(CDCl_3)\delta$;<br>1.1~2.2(9H,m), 2.7~3.1(2H,m), 3.50(2H,s)<br>4.03(2H,t), 6.50(1H,m), 6.9~7.9(9H,m),<br>8.47(1H,d)<br>mol. form.; $C_{23}H_{26}N_2O \cdot HCl$ |
| 54 | (dihydroisoquinolinone)-N-CH₂CH₂-(piperidine)-N-CH₂-(phenyl) · HCl | $^1H-NMR(CDCl_3)\delta$;<br>1.1~2.2(9H,m), 2.7~3.1(4H,m), 3.4~3.7<br>(6H,m), 7.0~7.6(8H,m), 8.06(1H,m)<br>mol. form.; $C_{23}H_{28}N_2O \cdot HCl$ |
| 55 | (N-acetyl dihydroquinazolinone)-N-CH₂CH₂-(piperidine)-N-CH₂-(phenyl) · HCl | $^1H-NMR(CDCl_3)\delta$;<br>1.10~2.20(11H,m), 2.27(3H,m), 2.93(2H,bd),<br>3.48~3.70(4H,m), 7.27(5H,s), 7.28~8.12<br>(4H,m)<br>mol. form.; $C_{24}H_{29}N_3O_2 \cdot HCl$ |
| 56 | (isoindolinone)-N-CH₂CH₂-(piperidine)-N-CH₂-(phenyl) · HCl | $^1H-NMR(CDCl_3)\delta$;<br>1.10~2.20(9H,m), 2.93(2H,bd), 3.40~3.65<br>(6H,m), 4.43(2H,s), 7.00~7.50(4H,m),<br>7.31(5H,s)<br>mol. form.; $C_{23}H_{28}N_2O \cdot HCl$ |
| 57 | (tetrahydroisoquinoline)-N-CH₂CH₂-(piperidine)-N-CH₂-(phenyl) · 2HCl | $^1H-NMR(CDCl_3)\delta$;<br>1.10~2.20(9H,m), 2.22~2.97(8H,m), 3.45(2H,<br>s), 3.55(2H,s), 6.90~7.20(4H,m), 7.20(5H,s)<br>mol. form.; $C_{23}H_{30}N_2 \cdot 2HCl$ |
| 58 | (piperidinone)-N-CH₂CH₂-(piperidine)-N-CH₂-(phenyl) · HCl | $^1H-NMR(CDCl_3)\delta$;<br>1.10~2.16(13H,m), 2.16~2.50(2H,m), 2.87<br>(2H,bd), 3.03~3.43(4H,m), 3.48(2H,s),<br>7.27(5H,s)<br>mol. form.; $C_{19}H_{20}N_2O \cdot HCl$ |
| 59 | (methyl-dihydroisoquinolinone)-N-CH₂CH₂-(piperidine)-N-CH₂-(phenyl) · HCl | $^1H-NMR(CDCl_3)\delta$;<br>1.10~2.10(9H,m), 1.46(3H,d), 2.87(2H,bd),<br>3.35~3.72(3H,m), 3.46(2H,s), 4.40(2H,dd),<br>7.00~7.38(4H,m), 7.28(5H,s)<br>mol. form.; $C_{24}H_{30}N_2O \cdot HCl$ |

TABLE 5-continued

| Ex. No. | Structural formula | Physicochemical constant (m.p., elem. anal., NMR, etc.) |
|---|---|---|
| 60 | | $^1$H—NMR(CDCl$_3$)δ; 1.20~2.84(2H,m), 3.44(2H,s), 7.14~7.25 (9H,m) mol. form.; C$_{25}$H$_{32}$N$_2$O.HCl |
| 61 | | $^1$H—NMR(CDCl$_3$)δ; 1.44~1.80(15H,m), 2.96(2H,bs), 2.56(2H,s), 7.08~7.40(9H,m) mol. form.; C$_{23}$H$_{28}$N$_2$O.HCl |
| 62 | | $^1$H—NMR(CDCl$_3$)δ; 1.24~2.50(5H,m), 2.18(2H,bs), 2.54~2.88 (4H,m), 3.44(2H,s), 3.76(3H,s), 6.64~6.76 (2H,m), 6.99(1H,d), 7.20(5H,s) mol. form.; C$_{25}$H$_{32}$N$_2$O$_2$.HCl |
| 63 | | $^1$H—NMR(CDCl$_3$)δ; 1.25~2.20(15H,m), 2.58(2H,bt), 2.86(2H,bs), 3.48(2H,s), 3.75(3H,s), 6.56~6.68(2H,m), 7.00(1H,d), 7.21(5H,s) mol. form.; C$_{25}$H$_{32}$N$_2$O$_2$.HCl |
| 64 | | $^1$H—NMR(CDCl$_3$)δ; 1.38~2.02(12H,m), 2.96(2H,d), 5.60(2H,s), 4.94(4H,m), 7.08~7.36(9H,m) mol. form; C$_{23}$H$_{29}$N$_3$O.HCl |
| 65 | | $^1$H—NMR(CDCl$_3$)δ; 1.32~2.36(15H,m), 2.84~3.02(2H,m), 3.59(2H,s), 4.09(3H,s), 6.72~6.88(2H,m), 7.20~7.44(7H,m) mol. form.; C$_{25}$H$_{32}$N$_2$O$_2$.HCl |
| 66 | | $^1$H—NMR(CDCl$_3$)δ; 1.10~2.10(11H,m), 2.60~3.00(4H,m), 3.45 (2H,s), 3.45~3.80(1H,m), 3.86(6H,s), 6.22 (1H,bs), 6.57(1H,s), 7.20(5H,s), 7.46(1H,s) mol. form.; C$_{25}$H$_{32}$N$_2$O$_3$.HCl |

TABLE 5-continued

| Ex. No. | Structural formula | Physicochemical constant (m.p., elem. anal., NMR, etc.) |
|---|---|---|
| 67 | (3,4-dimethoxy-N-methyl-isoquinolinone with CH₂CH₂-piperidine-N-CH₂-phenyl) ·HCl | $^1$H—NMR(CDCl$_3$)δ; 1.08~2.10(11H,m), 2.50~2.95(4H,m), 3.01 (3H,s), 3.45(2H,s), 3.45~3.60(1H,m), 3.85 (6H,s), 6.52(1H,s), 7.10(1H,s), 7.20(5H,s) mol. form.; C$_{26}$H$_{34}$N$_2$O$_3$·HCl |
| 68 | (3,4-dimethoxy-NH-isoquinolinone with CH₂-piperidine-N-CH₂-phenyl) ·HCl | $^1$H—NMR(CDCl$_3$)δ; 1.02~2.12(9H,m), 2.50~3.05(4H,m), 3.43(2H, s), 3.43~3.85(1H,m), 3.88(6H,s), 6.58(1H, s), 6.50~6.82(1H,m), 7.20(5H,s), 7.46(1H, s) mol. form.; C$_{24}$H$_{30}$N$_2$O$_3$·HCl |
| 69 | (benzodiazepinone with N-CH₂CH₂-piperidine-N-CH₂-phenyl and N-CH₂CH₃) ·2HCl | $^1$H—NMR(CDCl$_3$)δ; 1.17(3H,t), 1.10~2.15(9H,m), 2.68(2H,q) 2.89(2H,bd), 3.14(2H,s), 3.51(2H,s), 3.55(2H,s), 3.87(2H,bt), 7.07~7.35(9H,m) mol. form.; C$_{25}$H$_{33}$N$_3$O·2HCl |

TABLE 6

| Ex. No. | Structural formula | Physicochemical constant (m.p., elem., anal., NMR, etc.) |
|---|---|---|
| 70 | (piperidine-CH₂CH₂-N(benzodiazepinone with N-CH₃)-phenyl·HCl) | ¹H—NMR(CDCl₃)δ; (in free form) 1.01~2.40(9H,m), 2.70~3.30(4H,m), 3.46(3H,s), 3.54(2H,s), 3.90~4.20(2H,m), 6.90~8.20(9H,m) mol. form.; C₂₄H₂₉N₃O₂·HCl |
| 71 | (piperidine-N-CH₂-phenyl, with N-CH₂CH₂ acyl benzene·HCl) | ¹H—NMR(CDCl₃)δ; 1.12~2.12(9H,m), 2.76~3.00(2H,m), 3.50(2H,s), 3.66(2H,t), 4.36(2H,s), 7.08~7.92(9H,m) |
| 72 | (piperidine-N-CH₂-phenyl·HCl; pyrazine-CONHCH₂CH₂-COOC₂H₅) | ¹H—NMR(CDCl₃)δ; 1.08~2.16(9H,m), 1.42(3H,t), 2.76~3.00(2H,m), 3.32~3.62(2H,m), 3.50(2H,m), 4.53(q,2H), 7.12~7.40(5H,m), 7.48~7.72(1H,m), 8.58(1H,d), 8.73(1H,d) |
| 73 | (piperidine-N-CH₂-phenyl·HCl; pyrazine-CONHCH₂CH₂-COOCH₂CH₂CH₃) | ¹H—NMR(CDCl₃)δ; 0.95(3H,t), 1.04~2.10(13H,m), 3.68~4.00 (2H,m), 4.28~4.60(2H,m), 4.48(2H,s), 5.46(3H,s), 7.74(5H,s), 7.48~7.72(1H,m), 8.57(1H,d), 8.71(1H,d) |
| 74 | (piperidine-N-CH₂-phenyl·HCl; pyrazine-CH₃/CONCH₂CH₂-COOEt) | ¹H—NMR(CDCl₃)δ; 1.00~2.06(9H,m), 2.70~2.92(2H,m), 3.00~3.13(2H,m), 3.34~3.60(4H,m), 7.26 (5H,s), 8.52(1H,d), 8.62(1H,d), 8.91(1H,d) |
| 75 | (piperidine-N-CH₂-phenyl·HCl; pyrazine-CH₃/CONCH₂CH₂-COOEt) | ¹H—NMR(CDCl₃)δ; 0.92~2.06(9H,m), 1.40(3H,t), 2.64~2.91 (2H,m), 3.12(3H,s), 3.36~3.72(4H,m), 4.46(2H,q), 7.28(5H,s), 8.73(2H,d) |

TABLE 6-continued

| Ex. No. | Structural formula | Physicochemical constant (m.p., elem. anal., NMR, etc.) |
|---|---|---|
| 76 | (pyrazine with CONHCH₂CH₂-[piperidine-N-CH₂-phenyl·HCl] and COOCH₃) | ¹H—NMR(CDCl₃)δ; 1.10~2.16(9H,m), 2.72~3.02(2H,m), 3.10~3.62(2H,m), 3.51(2H,s), 4.04(3H,s), 7.2~7.48(5H,m), 7.48~7.80(1H,m), 8.60 (1H,d), 8.69(1H,d) |
| 77 | (pyrazine with CONHCH₂CH₂-[piperidine-N-CH₂-phenyl·HCl] and NHCOCH₃) | ¹H—NMR(CDCl₃)δ; 1.04~2.28(9H,m), 2.36(3H,s), 3.44(2H,s), 3.50~3.76(2H,m), 7.12~7.25(5H,m), 9.03(2H,s) |
| 78 | (pyrazine with CONHCH₂CH₂-[piperidine-N-CH₂-phenyl·HCl] and CONH₂) | ¹H—NMR(CDCl₃)δ; 0.96~2.16(9H,m), 2.56~3.00(2H,m), 3.00~3.40(2H,t), 3.44(2H,s), 7.20(5H,s), 8.02(2H,s) |
| 79 | (pyrazine with CONHCH₂CH₂-[piperidine-N-CH₂-phenyl·HCl] and COO-cyclohexyl) | ¹H—NMR(CDCl₃)δ; 1.04~2.24(9H,m), 2.76~3.00(2H,m), 3.34~3.66(2H,m), 3.50(2H,s), 5.04~5.28(1H,m), 7.10~7.36(5H,m), 7.48~7.72(1H,m), 8.54 (1H,d), 8.54(1H,d) |
| 80 | (pyridine with Cl and CONHCH₂CH₂-[piperidine-N-CH₂-phenyl·2HCl]) | ¹H—NMR(CDCl₃)δ; 1.08~2.16(9H,m), 2.76~3.06(2H,m), 3.24~3.68(2H,m), 3.54(2H,s), 7.18~7.46(6H,m), 8.00~8.18(1H,m), 8.28~8.54(1H,m) |
| 81 | (quinoxaline with CH(CH₃)CONHCH₂- [piperidine-N-CH₂-phenyl·HCl]) | ¹H—NMR(CDCl₃)δ; 0.98~2.16(9H,m), 2.60~3.00(2H,m), 3.14(3H,s), 3.32~3.72(4H,m), 7.04~7.32(5H,m), 7.60~7.82(1H,m), 7.84~8.15(2H,m), 9.05(1H,s) |

TABLE 6-continued

| Ex. No. | Structural formula | Physicochemical constant (m.p, elem. anal., NMR, etc.) |
|---|---|---|
| 82 | quinoline-C(=O)-N(CH₃)-CH₂CH₂-[piperidine]-N-CH₂-phenyl · 2HCl | $^1$H—NMR(CDCl$_3$)δ; 1.00~2.05(9H,m), 2.56~3.00(2H,m), 3.08, 3.12(total 3H, each s), 3.30~3.70(4H,m), 7.18,7.21(total 5H, each s), 7.33~8.22 (6H,m) |
| 83 | quinoline-C(=O)-NHCH₂CH₂-[piperidine]-N-CH₂-phenyl · 2HCl | $^1$H—NMR(CDCl$_3$)δ; 1.11~2.09(9H,m), 2.87(2H,bd), 3.20~3.62(4H, m), 7.22(5H,s), 7.41~7.64(3H,m), 8.00(1H, dd), 8.20(2H,s)<br>mol. form.; C$_{24}$H$_{27}$N$_3$O.2HCl |
| 84 | quinoline(3-yl)-C(=O)-NHCH₂CH₂-[piperidine]-N-CH₂-phenyl · 2HCl | m.p. (°C); 197.5~198.5<br>elem. anal.: C$_{24}$H$_{27}$N$_3$O.2HCl<br>    C    H    N<br>calcd. (%) 64.57 6.55 9.41<br>found (%) 64.26 6.58 9.35 |
| 85 | quinoxaline-C(=O)-NHCH₂CH₂-[piperidine]-N-CH₂-phenyl-OCH$_3$ · HCl | m.p. (°C); 174~176.5<br>elem. anal.: C$_{24}$H$_{28}$N$_4$O$_2$.HCl<br>    C    H    N<br>calcd. (%)   65.37 6.63 12.71<br>found (%)   64.96 6.63 12.60<br>1/20H$_2$O (%) 64.97 6.66 12.63 |

TABLE 7

| Ex. No. | Structural formula | Physicochemical constant (m.p., elem. anal., NMR, etc.) |
|---|---|---|
| 86 | (pyrazine with CONHCH₂CH₂-piperidine-N-CH₂-phenyl and CONHEt substituent).HCl | ¹H—NMR(CDCl₃)δ; 0.96~2.24(9H, m), 1.25(3H, t), 2.60~3.08(2H, m), 3.44(2H, s), 3.12~3.15(4H, m), 7.20 (5H, s), 8.44(2H, s) |
| 87 | (quinoline-3-C(O)-N(CH₃)-CH₂CH₂-piperidine-N-CH₂-phenyl).2HCl | ¹H—NMR(CDCl₃)δ; 1.00~2.08(9H, m), 2.70(2H, bd), 3.04(3H, bd), 3.40(2H, bd), 7.17(5H, s), 7.40~7.61(2H, m), 7.66~7.82(2H, m), 7.99~8.11(2H, m), 7.83 (1H, d) mol. form.; $C_{25}H_{29}N_3O \cdot 2HCl$ |
| 88 | (4-nitrobenzoyl-N(phenyl)-CH₂CH₂-piperidine-N-CH₂-phenyl).HCl | ¹H—NMR(CDCl₃)δ; 1.1~2.1(9H, m), 2.7~3.0(2H, m), 3.50(2H, s), 3.90(2H, t), 6.9~7.6(12H, m), 8.03(2H, d) mol. form.; $C_{27}H_{29}N_3O_3 \cdot HCl$ |
| 89 | (4-fluorobenzoyl-N(phenyl)-CH₂CH₂-piperidine-N-CH₂-phenyl).HCl | ¹H—NMR(CDCl₃)δ; 1.1~2.1(9H, m), 2.7~3.0(2H, m), 3.48(2H, s), 3.8~4.0(2H, m), 6.6~7.4(14H, m) mol. form.; $C_{27}H_{29}N_2OF \cdot HCl$ |
| 90 | (benzoyl-N(phenyl)-CH₂CH₂-piperidine-N-CH₂-phenyl).HCl | ¹H—NMR(CDCl₃)δ; 1.1~2.2(9H, m), 2.7~3.0(2H, m), 3.48(2H, s), 3.89(2H, m), 6.8~7.4(15H, m) mol. form.; $C_{27}H_{30}N_2O \cdot HCl$ |
| 91 | CH₃CH₂N(phenyl)CH₂CH₂-piperidine-N-CH₂-phenyl | ¹H—NMR(CDCl₃)δ; 1.16(3H, t), 1.1~2.2(9H, m), 2.7~3.0(2H, m), 3.1~3.4(4H, m), 3.52(2H, s), 6.5~7.4(10H, m) mol. form.; $C_{22}H_{30}N_2$ |
| 92 | (4-methoxybenzoyl-N(phenyl)-CH₂CH₂-piperidine-N-CH₂-phenyl) | ¹H—NMR(CDCl₃)δ; 1.10~2.06(9H, m), 2.82(2H, bd), 3.43(2H, s), 3.58(3H, s), 3.88(2H, bt), 6.50(2H, d), 6.69(2H, d), 6.98(5H, bs), 7.19(5H, s) mol. form.; $C_{28}H_{32}N_2O_2$ |
| 93 | CH₃C(O)N(4-methoxyphenyl)CH₂CH₂-piperidine-N-CH₂-phenyl.HCl | ¹H—NMR(CDCl₃)δ; 1.78(3H, s), 1.0~2.1(9H, m), 2.6~3.0(2H, m), 3.43(2H, s), 3.75(2H, m), 3.73(3H, s), 6.64(4H, dd), 7.26(5H, s) mol. form.; $C_{23}H_{30}N_2O_2 \cdot HCl$ |

TABLE 7-continued

| Ex. No. | Structural formula | Physicochemical constant (m.p., elem. anal., NMR, etc.) |
|---|---|---|
| 94 | (3-methoxyphenyl)-N-(CH₂CH₂-piperidine-N-CH₂-phenyl) with CH₃C(O)N, ·HCl | ¹H—NMR(CDCl₃)δ; 1.1~2.1(9H, m), 1.84(3H, s), 2.7~3.0(2H, m), 3.44(2H, s), 3.5~3.8(2H, m), 3.80(3H, s), 6.5~6.9(3H, m), 7.22(6H, s) mol. form.; C₂₃H₃₀N₂O₂ |
| 95 | pyrazine-C(O)-N(phenyl)-CH₂CH₂-piperidine-N-CH₂-phenyl, ·HCl | ¹H—NMR(CDCl₃)δ; 1.16~2.16(9H, m), 2.68~2.98(2H, m), 3.49(2H, s), 3.84~4.09(2H, t), 6.91~7.40 (10H, m), 8.22~8.44(2H, m), 8.62(1H, s) |
| 96 | cyclohexyl-C(O)-N(phenyl)-CH₂CH₂-piperidine-N-CH₂-phenyl, ·HCl | ¹H—NMR(CDCl₃)δ; 1.98~2.26(20H, m), 2.85(2H, bd), 3.48(2H, s), 3.62(2H, bt), 6.96~7.40(9H, m) mol. form.; C₂₇H₃₆N₂O·HCl |
| 97 | CH₃-S(O)₂-N(phenyl)-CH₂CH₂-piperidine-N-CH₂-phenyl, ·HCl | ¹H—NMR(CDCl₃)δ; 0.90~2.10(9H, m), 2.65~2.98(2H, m), 2.83 (3H, s), 3.47(2H, s), 3.52~9.92(2H, m), 7.26(5H, s), 7.26~7.43(5H, m) mol. form.; C₂₁H₂₀N₂O₂S·HCl |
| 98 | CH₃CH₂C(O)-N(phenyl)-CH₂CH₂-piperidine-N-CH₂-phenyl, ·HCl | ¹H—NMR(CDCl₃)δ; 1.02(3H, t), 1.10~2.00(9H, m), 1.98(2H, q), 2.80(2H, bd), 3.43(2H, s), 3.55~3.80(2H, m), 6.97~7.40(5H, m), 7.20 (5H, s) mol. form.; C₂₃H₃₀N₂O·HCl |
| 99 | (CH₃)₂N-C(O)-N(phenyl)-CH₂CH₂-piperidine-N-CH₂-phenyl, ·2HCl | ¹H—NMR(CDCl₃)δ; 1.0~2.1(9H, m), 2.18(6H, s), 2.6~3.0(4H, m), 3.38(2H, s), 3.4~3.8(2H, m), 6.9~7.5(10H, m) mol. form.; C₂₄H₃₃N₃O·2HCl |
| 100 | CH₃CH₂O-C(O)-N(phenyl)-CH₂CH₂-piperidine-N-CH₂-phenyl, ·HCl | ¹H—NMR(CDCl₃)δ; 1.17(3H, t), 1.1~2.1(9H, m), 2.6~2.9(2H, m), 3.40(2H, s), 3.4~3.8(2H, m), 4.08(2H, t), 7.19(10H, s) mol. form.; C₂₃₃₀N₂O₂·HCl |
| 101 | CH₃C(O)-N(4-pyridyl)-CH₂CH₂-piperidine-N-CH₂-phenyl | ¹H—NMR(CDCl₃)δ; 1.24~1.81(9H, m), 2.0(3H, s), 2.82~2.96 (2H, d), 3.54(2H, s), 3.80(2H, m), 7.18 (2H, dd), 7.36(5H, s), 8.70(2H, dd) mol. form.; C₂₁H₂₇N₃O |

TABLE 7-continued

| Ex. No. | Structural formula | Physicochemical constant (m.p., elem. anal., NMR, etc.) |
|---|---|---|
| 102 | [3-chlorophenyl-N(COCH₃)-CH₂CH₂-(4-piperidyl)-N-CH₂-phenyl]·HCl | ¹H—NMR(CDCl₃)δ; 1.83(3H, s), 1.0~2.2(9H, m), 2.6~3.0(2H, m), 3.43(2H, s), 3.66(3H, t), 6.8~7.4(9H, m) mol. form.; $C_{22}H_{27}N_2OCl·HCl$ |
| 103 | [phenyl-N(COCH=CH₂)-CH₂CH₂-(4-piperidyl)-N-CH₂-phenyl]·HCl | ¹H—NMR(CDCl₃)δ; 1.16~2.06(9H, m), 2.83(2H, bd), 3.47(2H, s), 3.78(2H, bt), 5.42(1H, dd), 5.90(1H, dd), 6.20(1H, dd), 6.99~7.40(10H, m) mol. form.; $C_{23}H_{28}N_2O·HCl$ |
| 104 | [4-fluorophenyl-N(COCH₃)-CH₂CH₂-(4-piperidyl)-N-CH₂-phenyl]·HCl | ¹H—NMR—(CDCl₃)δ; 1.14~2.03(12H, m), 2.83(2H, bd), 3.44(2H, s), 3.64(2H, bt), 7.00(2H, s), 7.08(2H, s), 7.22(5H, s) mol. form.; $C_{22}H_{27}FN_2O·HCl$ |
| 105 | [3-fluorophenyl-N(COCH₃)-CH₂CH₂-(4-piperidyl)-N-CH₂-phenyl]·HCl | ¹H—NMR(CDCl₃)δ; 1.15~1.95(12H, m), 2.84(2H, bd), 3.65(2H, s), 3.67(2H, bt), 6.75~7.07(3H, m), 7.23(6H, s) mol. form.; $C_{22}H_{27}FN_2O·HCl$ |
| 106 | [3-methoxyphenyl-N(CO-4-pyridyl)-CH₂CH₂-(4-piperidyl)-N-CH₂-phenyl]·2HCl | ¹H—NMR(CDCl₃)δ; 1.0~2.1(9H, m), 2.6~3.0(2H, m), 3.43(2H, s), 3.85(2H, m), 6.4~6.7(3H, m), 6.9~7.3(8H, m), 8.34(2H, d) mol. form.; $C_{27}H_{31}N_3O_2·2HCl$ |
| 107 | [3-fluorophenyl-N(CO-4-pyridyl)-CH₂CH₂-(4-piperidyl)-N-CH₂-phenyl]·2HCl | ¹H—NMR(CDCl₃)δ; 1.0~2.1(9H, m), 2.6~3.0(2H, m), 3.41(2H, s), 3.84(2H, m), 6.6~7.2(5H, m), 7.22(5H, s), 8.37(2H, d) mol. form.; $C_{26}H_{28}N_3OF·2HCl$ |
| 108 | [3,5-dimethoxyphenyl-N(CO-4-pyridyl)-CH₂CH₂-(4-piperidyl)-N-CH₂-phenyl]·2HCl | ¹H—NMR(CDCl₃)δ; 1.0~2.1(9H, m), 2.6~3.0(2H, m), 3.43(2H, s), 3.57(6H, s), 3.83(2H, m), 6.0~6.2(3H, m), 7.0~7.4(7H, m), 8.35(2H, d) |
| 109 | [3-methylphenyl-N(COCH₃)-CH₂CH₂-(4-piperidyl)-N-CH₂-phenyl]·HCl | ¹H—NMR(CDCl₃)δ; 1.77(3H, s), 1.0~2.1(9H, m), 2.32(3H, s), 2.6~2.9(2H, m), 3.40(2H, s), 3.63(2H, m), 6.7~7.3(9H, m), mol. form.; $C_{28}H_{33}N_3O_3·HCl$ |

TABLE 7-continued

| Ex. No. | Structural formula | Physicochemical constant (m.p., elem. anal., NMR, etc.) |
|---|---|---|
| 110 | (structure: 3,5-dimethoxyphenyl-N(COCH$_3$)-CH$_2$CH$_2$-[piperidine]-N-CH$_2$-phenyl · HCl) | $^1$H—NMR(CDCl$_3$)δ; 1.85(3H, s), 1.1~2.2(9H, m), 2.6~3.0(2H, m), 3.42(2H, s), 3.60(2H, m), 3.75(6H, s), 6.20 (2H, d), 6.35(1H, m), 7.18(5H, s) mol. form.; C$_{24}$H$_{32}$N$_2$O$_3$·HCl |
| 111 | (structure: 4-pyridyl-CO-N(4-hydroxyphenyl)-CH$_2$CH$_2$-[piperidine]-N-CH$_2$-phenyl · 2HCl) | $^1$H—NMR(CDCl$_3$)δ; 1.1~2.1(9H, m), 2.6~3.0(2H, m), 3.50(2H, s), 3.83(2H, m), 6.58(4H, dd), 7.04(2H, d), 7.19(5H, s), 8.28(2H, d) mol. form.; C$_{26}$H$_{29}$N$_3$O$_2$·2HCl |
| 112 | (structure: 4-pyridyl-CO-N(3-hydroxyphenyl)-CH$_2$CH$_2$-[piperidine]-N-CH$_2$-phenyl · 2HCl) | $^1$H—NMR(CDCl$_3$)δ; 1.07~2.35(9H, m), 2.99(2H, bd), 3.62(2H, s), 3.81(2H, bt), 6.31~6.56(3H, m), 6.84~7.11 (3H, m), 7.25(5H, s), 8.31(2H, bs) mol. form.; C$_{26}$H$_{29}$N$_3$O$_2$·2HCl |
| 113 | (structure: 4-pyridyl-CO-N(4-methoxyphenyl)-CH$_2$CH$_2$-[piperidine]-N-CH$_2$-phenyl · 2HCl) | $^1$H—NMR(CDCl$_3$)δ; 1.1~2.1(9H, m), 2.6~3.0(2H, m), 3.44(2H, s), 3.68(3H, m), 3.85(2H, m), 6.78(4H, dd), 7.02(2H, d), 7.23(5H, s), 8.37(2H, d) mol. form.; C$_{27}$H$_{31}$N$_3$O$_2$·2HCl |
| 114 | (structure: 2-pyridyl-N(phenyl)-CH$_2$CH$_2$-[piperidine]-N-CH$_2$-phenyl · 2HCl) | $^1$H—NMR(CDCl$_3$)δ; 7.20(11H, m), 8.05(1H, m), 1.2~1.83(9H, m), 2.65~2.81(2H, d), 3.4(2H, s), 3.90(2H, m), 6.20~6.52(2H, m) mol. form.; C$_{25}$H$_{29}$N$_3$·2HCl |

TABLE 8

| Ex. No. | Structural formula | Physicochemical constant (m.p., elem. anal., NMR, etc.) |
|---|---|---|
| 115 | (structure: phenyl-CO-N(CH$_2$phenyl)-CH$_2$CH$_2$-[piperidine]-N-CH(CH$_3$)-phenyl · HCl) | $^1$H—NMR(CDCl$_3$)δ; 0.80~2.12(12H,m), 2.52~3.64(8H,m), 7.06~7.52(10H,m) |
| 116 | (structure: 4-aminophenyl-CO-N(CH$_3$)-CH$_2$CH$_2$-[piperidine]-N-CH$_2$-phenyl · 2HCl) | $^1$H—NMR(CDCl$_3$)δ; 1.08~2.10(9H,m), 2.80~2.92(2H,d), 3.00(3H,s), 3.34~3.50(4H,m), 3.90(2H,s), 6.60(2H,d), 7.21~7.28(7H,m) mol. form.; C$_{22}$H$_{29}$N$_3$O·2HCl |
| 117 | (structure: phenyl-CO-N(CH$_3$)-CH$_2$CH$_2$-[piperidine]-N-CH$_2$-(2-methylphenyl) · HCl) | $^1$H—NMR(CDCl$_3$)δ; 1.0~2.1(9H,m), 2.31(3H,s), 2.5~3.1(5H,m), 3.1~3.6(4H,m), 7.0~7.4(9H,m) mol. form.; C$_{23}$H$_{30}$N$_2$O·HCl |

TABLE 8-continued

| Ex. No. | Structural formula | Physicochemical constant (m.p., elem. anal., NMR, etc.) |
|---|---|---|
| 118 | 2-NO2-C6H4-CH2-C(O)-NH-CH2CH2-(4-piperidyl)-N-CH2-C6H5 · HCl | $^1$H—NMR(CDCl$_3$)δ; 1.0~2.2(9H,m), 2.7~3.0(2H,m), 3.29(2H,m), 3.50(2H,s), 3.81(2H,s), 5.8(1H,s), 7.25(5H,s), 7.3~7.7(3H,m), 8.03(1H,d) mol. form.; C$_{22}$H$_{27}$N$_3$O$_3$·HCl |
| 119 | C6H11-C(O)-N(CH3)-CH2CH2-(4-piperidyl)-N-CH2-C6H5 · HCl | $^1$H—NMR(CDCl$_3$)δ; (in free form) 1.10~2.06(17H,m), 2.10~2.32(3H,m), 2.96(3H,s), 3.20~3.52(4H,m), 4.08~4.16(2H,d), 7.36~7.76(5H,m) mol. form.; C$_{22}$H$_{34}$N$_2$O·HCl |
| 120 | 2-furyl-C(O)-N(CH3)-CH2CH2-(4-piperidyl)-N-CH2-C6H5 · HCl | $^1$H—NMR(CDCl$_3$)δ; 1.20~2.08(9H,m), 2.80~2.92(2H,d), 3.12(3H,s), 3.46~3.64(4H,m), 6.42(1H,dd), 7.00(1H,dd), 7.26~7.45(6H,m) mol. form.; C$_{20}$H$_{26}$N$_2$O$_2$·HCl |
| 121 | C6H5-C(O)-N(CH3)-CH2CH2-(4-piperidyl)-N-CH2CH=CH-C6H5 · HCl | $^1$H—NMR(CDCl$_3$)δ; 1.02~2.06(9H,m), 2.71~3.57(9H,m), 6.16~6.54(2H,m), 7.10~7.55(10H,m) mol. form.; C$_{24}$H$_{30}$N$_2$O·HCl |
| 122 | C6H5-O-C(O)-NH-CH2-(4-piperidyl)-N-CH2-C6H5 · HCl | $^1$H—NMR(CDCl$_3$)δ; 1.1~2.1(7H,m), 2.8~3.05(2H,m), 3.05~3.15(2H,m), 3.49(2H,s), 5.1(1H, ), 7.0~7.5(10H,m) mol. form.; C$_{20}$H$_{24}$N$_2$O$_2$·HCl |
| 123 | C6H5-C(O)-N(CH3)-CH2CH2-(4-piperidyl)-N-CH2CH2-C6H5 · HCl | $^1$H—NMR(CDCl$_3$)δ; 1.00~3.08(20H,m), 7.22(5H,bs), 7.37(5H,s) mol. form.; C$_{23}$H$_{30}$N$_2$O·HCl |
| 124 | C6H5-C(O)-NH-CH2CH2-(4-piperidyl)-N-CH2-(2-furyl) · HCl | $^1$H—NMR(CDCl$_3$)δ; 1.30~2.24(9H,m), 2.86(2H,bd), 3.32~3.60(4H,m), 6.08~6.28(2H,m), 7.20~8.02(6H,m) mol. form.; C$_{19}$H$_{24}$N$_2$O$_2$·HCl |
| 125 | C6H5-O-C(O)-CH2-(4-piperidyl)-N-CH2-C6H5 · HCl | $^1$H—NMR(CDCl$_3$)δ; 1.1~2.2(9H,m), 2.8~3.1(2H,m), 3.50(4H,s), 7.30(10H,s) mol. form.; C$_{20}$H$_{23}$NO$_3$·HCl |
| 126 | 2,6-(CH3O)2-C6H3-C(O)-NH-CH2CH2-(4-piperidyl)-N-CH2-C6H5 · HCl | $^1$H—NMR(CDCl$_3$)δ; (in free form) 1.20~2.16(9H,m), 2.64~3.0(2H,bd), 3.46(2H,s), 3.36~3.60(2H,m), 3.80(6H,s), 5.60(1H,bs), 6.50~6.60(2H,d), 7.16~7.40(6H, m) moo. form.; C$_{23}$H$_{30}$N$_2$O$_3$·HCl |
| 127 | 2-OH-6-OCH3-C6H3-C(O)-NH-CH2CH2-(4-piperidyl)-N-CH2-C6H5 · HCl | $^1$H—NMR(CDCl$_3$)δ; (in free form) 1.12~2.16(9H,m), 2.76~3.0(2H,bd), 3.48(2H,s), 3.32~3.60(2H,m), 3.92(3H,s), 6.32~7.40(8H,m), 8.26(1H,bs), 14.0(1H,s) mol. form.; C$_{22}$H$_{28}$N$_2$O$_3$·HCl |
| 128 | C6H5-O-C(O)-NH-CH2CH2-(4-piperidyl)-N-CH2-C6H5 · HCl | $^1$H—NMR(CDCl$_3$)δ; 1.1~2.2(9H,m), 2.7~3.0(2H,m), 3.1~3.4(2H, m), 3.46(2H,s), 4.90(1H), 6.9~7.4(10H,m) mol. form.; C$_{21}$H$_{26}$N$_2$O$_2$·HCl |

TABLE 8-continued

| Ex. No. | Structural formula | Physicochemical constant (m.p., elem. anal., NMR, etc.) |
|---|---|---|
| 129 | Ph-CH₂-C(O)-NHCH₂CH₂-[piperidine]-N-CH₂-Ph · HCl | ¹H—NMR(CDCl₃)δ; 1.1~2.2(9H,m), 2.7~3.0(4H,m), 3.1~3.6(2H,m), 3.55(2H,s), 5.5(1H), 7.30(10H,s) mol. form.; $C_{22}H_{28}N_2O\cdot HCl$ |
| 130 | Ph-CH=CH-C(O)-NHCH₂CH₂-[piperidine]-N-CH₂-Ph · HCl | ¹H—NMR(CDCl₃)δ; 1.1~2.2(9H,m), 2.7~3.0(2H,m), 3.2~3.4(2H,m), 3.40(2H,s) 5.9(1H), 6.39(1H,d), 7.1~7.8(11H,m) mol. form.; $C_{23}H_{28}N_2O\cdot HCl$ |
| 131 | 2-MeO-C₆H₄-C(O)-NHCH₂CH₂-[piperidine]-N-CH₂-Ph · HCl | ¹H—NMR(CDCl₃)δ; (in free form) 1.1~2.2(9H,m), 2.6~3.0(2H,bd), 3.44(2H,s), 3.36~3.6(2H,m), 3.90(3H,s), 6.9~8.30(10H,m) mol. form.; $C_{22}H_{20}N_2O_2\cdot HCl$ |
| 132 | Ph-CH₂CH₂-C(O)-NHCH₂CH₂-[piperidine]-N-CH₂-Ph · HCl | ¹H—NMR(CDCl₃)δ; 1.1~2.2(9H,m), 2.3~2.7(4H,m), 2.7~3.0(2H, m), 3.0~3.5(4H,m), 6.1(1H), 7.0~7.7(10H,m) mol. form.; $C_{23}H_{30}N_2O\cdot HCl$ |
| 133 | CH₃CH₂-C(O)-NHCH₂CH₂-[piperidine]-N-CH₂-Ph · HCl | ¹H—NMR(CDCl₃)δ; 1.17(3H,t), 1.2~2.1(9H,m), 2.17(2H,q), 2.7~3.0(2H,m), 3.1~3.4(2H,m), 3.45(2H,s), 5.3(1H), 7.21(5H,s) mol. form.; $C_{17}H_{26}N_2O\cdot HCl$ |
| 134 | Ph-CH(CH₃)-C(O)-NHCH₂CH₂-[piperidine]-N-CH₂-Ph · HCl | ¹H—NMR(CDCl₃)δ; 1.1~2.0(12H,m), 2.6~3.0(2H,m), 3.0~3.3(2H,m), 3.41(2H,s), 3.3~3.4(1H,m), 7.23(10H,s) mol. form.; $C_{23}H_{30}N_2O\cdot HCl$ |
| 135 | Ph-C(O)-N(CH₂Ph)-CH₂CH₂-[piperidine]-N-CH₂-Ph · HCl | ¹H—NMR(CDCl₃)δ; 0.90~2.10(9H,m), 2.78(2H,bd), 3.00~3.70(2H,m), 3.43(2H,s), 4.40~4.85(2H,m), 7.27(10H,s), 7.38(5H,s) mol. form.; $C_{28}H_{32}N_2O\cdot HCl$ |
| 136 | Ph-C(O)-COCH₂CH₂-[piperidine]-N-CH₂-Ph | ¹H—NMR(CDCl₃)δ; 1.0~2.1(9H,m), 2.7~3.0(2H,m), 3.48(2H,s), 4.36(2H,t), 7.0~7.7(8H,m), 7.8~8.2(2H,m) mol. form.; $C_{21}H_{25}NO_2$ |
| 137 | 4-O₂N-C₆H₄-C(O)-N(CH₂Ph)-CH₂CH₂-[piperidine]-N-CH₂-Ph · HCl | ¹H—NMR(CDCl₃)δ; 0.86~1.90(9H,m), 2.56~3.05(4H,m), 3.38(2H,d), 4.56(1H,s) 4.68(1H,s), 7.00~7.56(12H,m), 8.10(2H,m) mol. form.; $C_{28}H_{31}N_3O_3\cdot HCl$ |
| 138 | CH₂=CH-C(O)-NHCH₂CH₂-[piperidine]-N-CH₂-Ph · HCl | ¹H—NMR(CDCl₃)δ; 1.0~2.1(9H,m), 2.7~3.0(2H,m), 3.1~3.4(2H,m), 3.47(2H,s), 5.58(1H,dd), 5.9~6.1(2H,m), 7.29(5H,s) mol. form.; $C_{17}H_{24}N_2O\cdot HCl$ |

TABLE 8-continued

| Ex. No. | Structural formula | Physicochemical constant (m.p., elem. anal., NMR, etc.) |
|---|---|---|
| 139 | (benzoyl)-N(CH3)-CH2CH2-(piperidine)-N-benzoyl | $^1$H—NMR(CDCl$_3$)δ; 1.00~4.08(16H,m), 7.38(10H,s) mol. form.; C$_{22}$H$_{26}$N$_2$O$_2$ |
| 140 | (benzoyl)-N(CH3)-CH2CH2-(piperidine)-N-CH2-C6H4-NO2 .HCl | $^1$H—NMR(CDCl$_3$)δ; 0.90~2.10(9H,m), 2.55~3.50(7H,m), 3.52(2H,s), 7.38(5H,s), 7.80(4H,ABq) mol. form.; C$_{22}$H$_{27}$N$_3$O$_3$.HCl |
| 141 | (3-benzoylphenyl)-C(O)-N(CH3)-CH2CH2-(piperidine)-N-CH2-C6H5 | $^1$H—NMR(CDCl$_3$)δ; 0.96~2.08(3H,m), 2.60~3.10(6H,m), 3.48(2H,d), 7.16~7.92(14H,m) |
| 142 | (2-benzoylphenyl)-C(O)-NHCH2CH2-(piperidine)-N-CH2-C6H5 .HCl | $^1$H—NMR(CDCl$_3$)δ; 0.80~2.04(9H,m), 2.48~2.88(2H,m), 3.12~3.52(4H,m) 7.03~7.72(14H,m) |
| 143 | (benzoyl)-N(CH3)-CH2CH2-(piperidine)-N-CH2-C6H4-CH2 .HCl | $^1$H—NMR(CDCl$_3$)δ; 1.01~2.01(19H,m), 2.33(3H,s), 2.63~3.04(5H,bd), 3.42(2H,bd), 7.15(4H,bs), 7.35(5H,s) mol. form.; C$_{23}$H$_{30}$N$_2$O.HCl |
| 144 | (benzoyl)-N(CH3)-CH2CH2-(piperidine)-N-CH2-C6H4(m-CH3) | $^1$H—NMR(CDCl$_3$)δ; 1.00~1.96(11H,m), 2.30(3H,s), 3.38(2H,bd), 7.02(4H,bd), 7.28(5H,s) mol. form.; C$_{23}$H$_{30}$N$_2$O |
| 145 | (benzoyl)-N(CH3)-CH2CH2-(piperidine)-N-CH2-C6H4(o-NO2) | $^1$H—NMR(CDCl$_3$)δ; 0.90~2.18(9H,m), 2.52~3.70(7H,m), 3.72(2H,s), 7.10~7.88(4H,m), 7.38(5H,s) mol. form.; C$_{22}$H$_{27}$N$_3$O$_3$ |
| 146 | (benzoyl)-N(CH3)-CH2CH2-(piperidine)-N-CH2-C6H4(m-NO2) .HCl | m.p. (°C.); 216~217 (dec.) elem. anal.: C$_{22}$H$_{27}$N$_3$O$_3$.HCl<br>　　　　C　　H　　N<br>calcd. (%)　63.23　6.75　10.05<br>found (%)　62.95　6.69　9.88 |
| 147 | (benzoyl)-N(CH3)-CH2CH2-(piperidine)-N-CH2-C(CH3)3 .HCl | $^1$H—NMR(CDCl$_3$)δ; 0.82(9H,s), 1.02~2.28(9H,m), 2.60~3.60(9H,m), 7.28(5H,s) mol. form.; C$_{20}$H$_{32}$N$_2$O.HCl |

TABLE 8-continued

| Ex. No. | Structural formula | Physicochemical constant (m.p., elem. anal., NMR, etc.) |
|---|---|---|
| 148 | [Ph-C(=O)-NHCH₂CH₂-(piperidine)-N-CH₂-C(CH₃)₃] · HCl | ¹H—NMR(CDCl₃)δ; 0.85(9H,s), 1.12~2.28(9H,m), 2.76(2H,bd), 3.42(2H,q), 7.38(3H,m), 7.67(2H,dd) mol. form.; $C_{19}H_{30}N_2O \cdot HCl$ |
| 149 | [Ph-C(=O)-N(CH₃)CH₂CH₂-(piperidine)-N-CH₂-C₆H₄-F] · HCl | ¹H—NMR(CDCl₃)δ; 1.0~2.2(9H,m), 1.62~2.1(5H,m), 2.2~2.6(4H,m), 6.8~7.7(9H,m) mol. form.; $C_{22}H_{27}N_2O \cdot HCl$ |
| 150 | [Ph-C(=O)-N(CH₂Ph)CH₂CH₂-(piperidine)-N-CH₂-Ph] · HCl | ¹H—NMR(CDCl₃)δ; 1.00~2.05(9H,m), 2.08, 2.12(total 3H, each s), 2.82(2H,bd), 3.03~3.43(2H,m), 3.44(2H,s), 4.47, 4.56(total 3H, each s), 7.35(10H,s) mol. form.; $C_{23}H_{30}N_2O \cdot HCl$ |
| 151 | [Ph-CH₂-C(=O)-N(CH₃)CH₂CH₂-(piperidine)-N-CH₂-Ph] · HCl | ¹H—NMR(CDCl₃)δ; 1.00~2.08(9H,m), 2.78(2H,bd), 2.88(3H,s), 3.10~3.45(2H,m), 3.43(2H,s), 3.57(2H,s), 7.22(10H,s) mol. form.; $C_{23}H_{30}N_2O \cdot HCl$ |
| 152 | [CH₃-C(=O)-N(CH₃)CH₂CH₂-(piperidine)-N-CH₂-Ph] · HCl | ¹H—NMR(CDCl₃)δ; 1.00~2.00(9H,m), 2.03(3H,s), 2.80(2H,bd), 2.88, 2.91(total 3H, each s), 3.05~3.40(2H,m), 3.43(3H,s), 7.20(5H,s) mol. form.; $C_{17}H_{26}N_2O \cdot HCl$ |
| 153 | [4-O₂N-C₆H₄-CH=CH-C(=O)-N(CH₃)CH₂CH₂-(piperidine)-N-CH₂-Ph] · HCl | ¹H—NMR(CDCl₃)δ; 1.1~2.2(9H,m), 2.6~3.2(5H,m), 3.2~3.6(4H,m), 6.8~7.1(1H,m), 7.3(5H,s), 7.5~7.8(3H,m), 8.24(2H,d) mol. form.; $C_{26}H_{29}N_3O_3 \cdot HCl$ |
| 154 | [Ph-C(=O)-N(CH₃)CH₂CH₂-(piperidine)-N-CH₂-(furan)] · HCl | ¹H—NMR(CDCl₃)δ; 1.00~2.08(10H,m), 2.72~3.08(5H,m), 3.33(2H,bd), 6.16(1H,bs), 7.07(7H,bs) mol. form.; $C_{20}H_{26}N_2O_2 \cdot HCl$ |
| 155 | [Ph-C(=O)-N(CH₃)CH₂CH₂-(piperidine)-N-CH₂-cyclopropyl] · HCl | ¹H—NMR(CDCl₃)δ; 0.15(2H,m), 0.56(2H,m), 0.90~2.23(10H,m), 3.00(5H,m), 3.34(4H,m), 7.40(5H,s) mol. form.; $C_{19}H_{28}N_2O \cdot HCl$ |
| 156 | [Ph-C(=O)-N(CH₃)CH₂CH₂-(piperidine)-N-CH₂-(3-pyridyl)] · 2HCl | ¹H—NMR(CDCl₃)δ; 1.00~2.02(9H,m), 2.64~3.00(5H,m), 3.41(4H,m), 7.15(1H,m), 7.27(5H,s), 7.50(1H,d), 8.41(2H,m) mol. form.; $C_{21}H_{27}N_3O \cdot 2HCl$ |
| 157 | [Ph-C(=O)-N(CH₃)CH₂CH₂-(piperidine)-N-CH₂-(2-pyridyl)] · 2HCl | ¹H—NMR(CDCl₃)δ; 1.04~1.04(11H,m), 2.64~3.00(5H,m), 3.58(2H,s), 7.01(1H,m), 7.27(5H,s), 7.58(2H,m), 8.44(1H,d) mol. form.; $C_{21}H_{27}N_3O \cdot 2HCl$ |

TABLE 8-continued

| Ex. No. | Structural formula | Physicochemical constant (m.p., elem. anal., NMR, etc.) |
|---|---|---|
| 158 | 4-O₂N-C₆H₄-CH₂C(O)NHCH₂CH₂-[piperidine]-N-CH₂-C₆H₅ · HCl | $^1$H—NMR(CDCl$_3$)δ; 1.00~2.00(4H,m), 2.83(2H,bd), 3.24(2H,bd), 3.45(2H,s), 3.59(2H,s), 5.85(1H,bs), 7.27(5H,s), 7.77(4H,ABq) mol. form.; C$_{22}$H$_{27}$N$_3$O$_3$·HCl |
| 159 | 2-naphthyl-C(O)N(CH₃)CH₂CH₂-[piperidine]-N-CH₂-C₆H₅ · HCl | $^1$H—NMR(CDCl$_3$)δ; 1.0~2.1(9H,m), 2.6~3.2(5H,m), 3.2~3.7(4H,m), 7.25(5H,s), 7.3~8.1(7H,m) mol. form.; C$_{26}$H$_{30}$N$_2$O·HCl |
| 160 | 4-CH₃COO-C₆H₄-C(O)N(CH₃)CH₂CH₂-[piperidine]-N-CH₂-C₆H₅ · HCl | $^1$H—NMR(CDCl$_3$)δ; 1.00~2.10(9H,m), 2.25(3H,s), 2.81(2H,bd), 2.97(3H,bs), 3.10~3.45(2H,m), 3.43(2H,s), 7.23(4H,ABq), 7.27(5H,s) mol. form.; C$_{24}$H$_{30}$N$_2$O$_3$·HCl |
| 161 | C₆H₅-C(O)N(CH₃)CH₂CH₂-[piperidine]-N-CH₂-(4-pyridyl) · HCl | $^1$H—NMR(CDCl$_3$)δ; 1.06~1.92(9H,m), 2.70~2.99(5H,m), 3.44(2H,s), 7.22(2H,d), 7.38(5H,s), 8.50(2H,d) mol. form.; C$_{21}$H$_{27}$N$_3$O·2HCl |
| 162 | 1-naphthyl-C(O)N(CH₃)CH₂CH₂-[piperidine]-N-CH₂-C₆H₅ · HCl | $^1$H—NMR(CDCl$_3$)δ; 0.90~1.05(9H,m), 2.70(3H,s), 3.00(2H,d), 3.22(2H,s), 3.37(1H,s), 3.46(1H,s), 7.18~7.60(9H,m), 7.78(3H,m) mol. form.; C$_{26}$H$_{30}$N$_2$O·HCl |
| 163 | 4-O₂N-C₆H₄-C(O)NHCH₂CH₂-[piperidine]-N-CH₂-cyclohexyl | $^1$H—NMR(CDCl$_3$)δ; 0.7~2.2(20H,m), 2.8~3.2(4H, ), 3.55(2H,m), 6.95(1H,s), 8.02(2H,d), 8.34(2H,d) mol. form.; C$_{21}$H$_{31}$N$_3$O$_2$ |
| 164 | EtOOCCH=CHC(O)N(CH₃)CH₂CH₂-[piperidine]-N-CH₂-C₆H₅ · HCl | $^1$H—NMR(CDCl$_3$)δ; 1.1~2.1(12H,m), 2.7~3.1(5H,m), 3.2~3.6(4H, m), 4.22(2H,q), 6.7(1H,m), 7.2~7.4(6H,m) mol. form.; C$_{21}$H$_{30}$N$_2$O$_3$·HCl |
| 165 | C₆H₅CH₂SO₂-C₆H₄-C(O)N(CH₃)CH₂CH₂-[piperidine]-N-CH₂-cyclohexyl · HCl | $^1$H—NMR(CDCl$_3$)δ; 0.56~3.36(23H,m), 3.40~3.68(2H,m), 4.28(2H,s), 7.18(5H,s), 8.34(2H,d), 8.58(2H,d) |
| 166 | phenanthridinone-N-CH₂CH₂-[piperidine]-N-CH₂-C₆H₅ · HCl | $^1$H—NMR(CDCl$_3$)δ; 1.16~2.12(9H,m), 2.89(2H,bd), 3.47(2H,s), 4.35(2H,bt), 7.08~7.74(11H,m), 8.08(1H, bd), 8.23(1H,dd) |

TABLE 8-continued

| Ex. No. | Structural formula | Physicochemical constant (m.p., elem. anal., NMR, etc.) |
|---|---|---|
| 167 | 4-CHO-C6H4-CO-N(CH3)-CH2CH2-[piperidine]-N-CH2-C6H5 · HCl | $^1$H—NMR(CDCl$_3$)δ; 1.08~1.94(9H,m), 2.68~3.02(7H,m), 3.40(2H,d), 7.27(5H,s), 7.41(2H,d), 7.78(2H,d), 10.0(1H,s) mol. form.; C$_{23}$H$_{28}$N$_2$O$_2$·HCl |
| 168 | 4-(iPr)-C6H4-CO-N(CH3)-CH2CH2-[piperidine]-N-CH2-C6H5 · HCl | $^1$H—NMR(CDCl$_3$)δ; 1.10~1.98(15H,m), 2.77~2.98(6H,m), 3.12~3.46(4H,m), 7.26(9H,m) mol. form.; C$_{25}$H$_{34}$N$_2$O·HCl |
| 169 | 4-(F3C)-C6H4-CO-N(CH3)-CH2CH2-[piperidine]-N-CH2-C6H5 · HCl | $^1$H—NMR(CDCl$_3$)δ; 1.00~2.00(9H,m), 2.60~3.00(7H,m), 3.45(2H,m), 6.95(2H,d), 7.26(5H,s), 7.90(2H,d) mol. form.; C$_{23}$H$_{27}$N$_2$OF$_3$·HCl |
| 170 | 4-HO-C6H4-CO-N(CH3)-CH2CH2-[piperidine]-N-CH2-C6H5 · HCl | $^1$H—NMR(CDCl$_3$)δ; 1.00~2.10(3H,m), 2.87(2H,bd), 2.99(3H,s), 3.10~3.50(2H,m), 3.48(3H,s) 6.35~7.35(5H,m), 7.83(5H,s) mol. form.; C$_{22}$H$_{28}$N$_2$O$_2$·HCl |
| 171 | 4-EtO-C6H4-CO-N(CH3)-CH2CH2-[piperidine]-N-CH2-C6H5 · HCl | $^1$H—NMR(CDCl$_3$)δ; 1.10~1.88(12H,m), 2.80(2H,d), 2.98(3H,s), 3.23~3.44(4H,m), 4.02(2H,m), 6.84(2H,d), 7.26(7H,m) mol. form.; C$_{24}$H$_{32}$N$_2$O$_2$·HCl |
| 172 | 4-(4-pyridyl-CH2O)-C6H4-CO-N(CH3)-CH2CH2-[piperidine]-N-CH2-C6H5 · 2HCl | $^1$H—NMR(CDCl$_3$)δ; 1.00~2.08(9H,m), 2.83(2H,bd), 2.98(3H,s), 3.12~3.50(2H,m), 3.47(2H,s), 5.08(2H,s), 7.15(4H,ABq), 7.38(5H,s), 7.96(2H,ABq) |
| 173 | 4-pyridyl-CO-N(CH3)-CH2CH2-[piperidine]-N-C6H5 · HCl | $^1$H—NMR(CDCl$_3$)δ; 1.04~1.98(7H,m), 2.20~3.80(7H,m), 6.60~7.34(7H,m), 8.67(2H,d) |
| 174 | CH3OOC-C6H4-CO-N(CH3)-CH2CH2-[piperidine]-N-CH2-C6H5 · HCl | $^1$H—NMR(CDCl$_3$)δ; 0.90~2.20(11H,m), 2.60~3.30(2H,m), 2.85, 3.03(total 3H, each bs), 3.48,3.55(total 2H, each bs), 3.88(3H,s), 7.19, 7.21(total 5H, each s), 7.67(4H,ABq) mol. form.; C$_{24}$H$_{30}$N$_2$O$_2$·HCl |
| 175 | CH3CH2OCH2-C6H4-CO-N(CH3)-CH2CH2-[piperidine]-N-CH2-C6H5 · HCl | $^1$H—NMR(CDCl$_3$)δ; 0.90~2.06(9H,s), 2.70~3.02(10H,m), 3.20~3.62(4H,m), 4.50(2H,s), 7.21~7.30(9H,d) mol. form.; C$_{25}$H$_{34}$N$_2$O$_2$·HCl |
| 176 | dibenzoxepine-CO-N-CH2CH2-[piperidine]-N-CH2-C6H5 · HCl | $^1$N—NMR(CDCl$_3$)δ; 9.90~2.10(9H,m), 2.81(2H,bd), 3.45(2H,s), 4.11(2H,t), 6.98~7.82(8H,m), 7.21(5H,s) mol. form.; C$_{27}$H$_{28}$N$_2$O$_2$·HCl |

TABLE 8-continued

| Ex. No. | Structural formula | Physicochemical constant (m.p., elem. anal., NMR, etc.) |
|---|---|---|
| 177 | 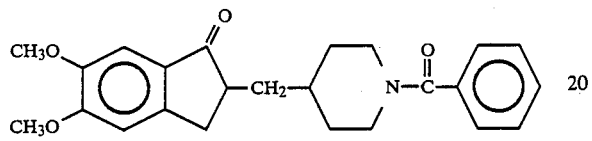 .HCl | $^1$H—NMR(CDCl$_3$)δ; 1.29(3H,s), 1.40(3H,s), 1.40~2.20(9H,m), 2.83(2H,bd), 3.00(3H,s), 3.20~3.50(2H,m), 3.48(2H,s), 4.56(1H, quirtet), 7.08 (4H, ABq), 7.28(5H,s) mol. form.; C$_{25}$H$_{34}$N$_2$O$_2$.HCl |

EXAMPLE 178

1-Benzoyl-4-[(5,6-dimethoxy-1-indanon)-2-yl]methyl-piperidine

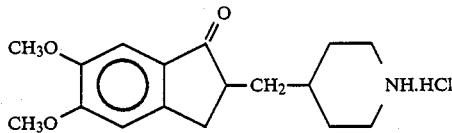

0.85 g of 5,6-dimethoxy-1-indanone and 1.38 g of 1-benzoyl-4-piperidinecarbaldehyde were dissolved in 20 ml of anhydrous THF to obtain a solution. 1.02 g of 28% sodium methylate was added to the solution at 0° C. The obtained mixture was stirred at a room temperature for 2 hours, diluted with ethyl acetate, washed with a saturated aqueous solution of common salt, dried over magnesium sulfate and concentrated in a vacuum. The obtained residue was purified through a silica gel column to obtain 1.23 g of 1-benzoyl-4-[(5,6-dimethoxy-1-indanon)-2-ylidenyl]methylpiperidine (yield: 71%).

1.23 g of this compound was dissolved in 20 ml of THF, followed by the addition of 0.3 g of 10% palladium/carbon. After the hydrogenation had been carried out at a room temperature under an ordinary pressure for one day, the catalyst was filtered out and the filtrate was concentrated in a vacuum. The residue was recrystallized from methylene chloride/hexane to obtain 1.10 g of the title compound (yield: 89%). The characteristics thereof are as follows:

m.p.(°C.): 151 to 152,
elemental analysis as C$_{24}$H$_{27}$NO$_4$,

|  | C | H | N |
|---|---|---|---|
| calculated (%) | 73.26 | 6.92 | 3.56 |
| found (%) | 73.30 | 6.85 | 3.32 |

EXAMPLE 179

4-[(5,6-Dimethoxy-1-indanon)-2-yl]methylpiperidine hydrochloride 9.00 g of 1-benzoyl-4-[(5,6-dimethoxy-1-indanon)2-yl]methylpiperidine was dissolved in 90 ml of dioxane, followed by the addition of 90 ml of 6N hydrochloric acid. The obtained mixture was heated under reflux for 10 hours and concentrated in a vacuum. The residue was diluted with water and extracted with ethyl acetate. The pH of the aqueous layer was adjusted to 12 with a 50% aqueous solution of sodium hydroxide and extracted with methylene chloride. The organic layer was washed with a saturated aqueous solution of common salt, dried over magnesium sulfate and concentrated in a vacuum. The obtained residue was converted into its hydrochloride by an ordinary method. The obtained product was recrystallized from methanol/ethanol to obtain 6.30 g of the title compound (yield: 85%). The characteristics thereof are as follows:

m.p.(°C.): 249 to 250 (dec.),
elemental analysis as C$_{17}$H$_{23}$NO$_3$.HCl,

|  | C | H | N |
|---|---|---|---|
| calculated (%) | 62.67 | 7.42 | 4.30 |
| found (%) | 62.75 | 7.31 | 4.52 |

EXAMPLE 180

1-(3-Fluorobenzyl)-4-[(5,6-dimethoxy-1-indanon)-2-yl]methylpiperidine hydrochloride

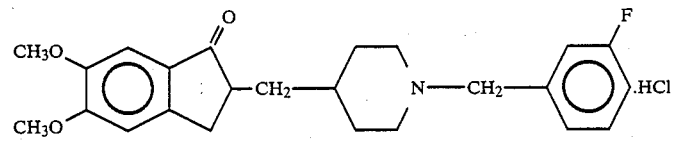

0.25 g of 4-[(5,6-dimethoxy-1-indanon)-2-yl]methylpiperidine was dissolved in 6 ml of THF, followed by the addition of 0.29 ml of triethylamine and 0.13 ml of 3-fluorobenzyl bromide. The obtained mixture was heated under reflux for 2 hours and concentrated in a vacuum. The residue was diluted with ethyl acetate, washed with a 10% aqueous solution of sodium carbonate and a saturated aqueous solution of common salt successively, dried over magnesium sulfate and concentrated in a vacuum. The obtained residue was purified through a silica gel column and converted into its hydrochloride by an ordinary method. The obtained product was recrystallized from methylene chloride/IPE to obtain 0.27 g of the title compound (yield: 72%). The characteristics thereof are as follows:

m.p.(°C.): 230 to 232 (dec.,)
elemental analysis as $C_{24}H_{28}NO_3 \cdot HCl$,

|  | C | H | N |
| --- | --- | --- | --- |
| calculated (%) | 66.43 | 6.74 | 3.23 |
| found (%) | 66.18 | 6.79 | 3.11 |

EXAMPLE 181

1-Benzyl-4-[(5,6-dimethoxy-1-indanon)-2-yl]methyl-piperidine dihydrochloride

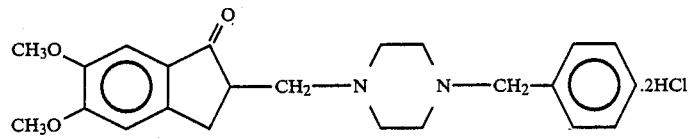

1.00 g of 5,6-dimethoxy-1-indanone, 0.31 g of paraformaldehyde and 0.90 ml of 1-benzylpiperazine were suspended in a mixture comprising 30 ml of ethanol and 2 ml of water. The pH of the obtained suspension was adjusted to 3 with concentrated hydrochloric acid, heated under reflux for 3 hours, cooled by allowing to stand and filtered to obtain a white solid. This solid was suspended in methylene chloride, washed with a 10% aqueous solution of sodium carbonate and a saturated aqueous solution of common salt successively, dried over magnesium sulfate and concentrated in a vacuum. The obtained residue was purified through a silica gel column and converted into its hydrochloride by an ordinary method. The product was recrystallized from methanol to obtain 0.55 g of the title compound (yield: 23%). The characterization thereof are as follows:

m.p.(°C.) 227 to 228 (dec.),
elemental analysis as $C_{23}H_{29}N_2O_3 \cdot 2HCl$,

|  | C | H | N |
| --- | --- | --- | --- |
| calculated (%) | 60.79 | 6.88 | 6.16 |
| found (%) | 60.31 | 6.95 | 6.06 |

EXAMPLE 182

4-[(5,6-Dimethoxy-1-indanon)-2-yl]methyl-1-ethoxycarbonylpiperidine

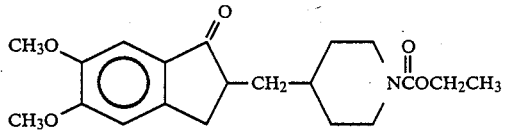

0.50 g of 1-benzyl-4-[(5,6-dimethoxy-1-indanon)-2-yl]methylpiperidine was dissolved in 8 ml of benzene, followed by the addition of 0.15 ml of ethyl chloroformate. The obtained mixture was heated under reflux for 3 hours, diluted with ethyl acetate, washed with a saturated aqueous solution of sodium bicarbonate and a saturated aqueous solution of common salt successively, dried over magnesium sulfate and concentrated in a vacuum. The obtained residue was recrystallized from ethyl acetate/hexane to obtain 0.45 g of the title compound (yield: 94%). The characteristics thereof are as follows:

m.p.(°C.): 132 to 133,
elemental analysis as $C_{20}H_{27}NO_5$,

|  | C | H | N |
| --- | --- | --- | --- |
| calculated (%) | 66.46 | 7.53 | 3.88 |
| found (%) | 66.79 | 7.53 | 4.00 |

EXAMPLE 183

4-[(5,6-Dimethoxy-1-indenon)-2-yl]methyl-1-ethoxycarbonylpiperidine

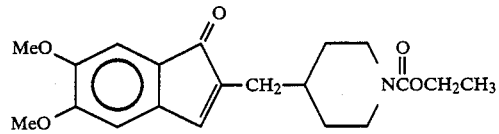

2.00 g of 4-[(5,6-dimethoxy-1-indanon)-2-yl]methyl-1-ethoxycarbonylpiperidine was dissolved in 30 ml of carbon tetrachloride, followed by the addition of 0.98 g of N-bromosuccinimide and 0.02 g of benzoyl peroxide. The obtained mixture was heated under reflux for 5 hours, diluted with carbon tetrachloride, washed with a saturated aqueous solution of sodium bicarbonate and a saturated aqueous solution of common salt successively, dried over magnesium sulfate and concentrated in a vacuum.

The obtained residue was dissolved in 20 ml of THF, followed by the addition of 1.66 ml of 1,8-diazabicyclo[5.4.0]undec-7-ene. The obtained mixture was heated under reflux for 30 minutes and concentrated in a vacuum. The residue was diluted with ethyl acetate, washed with a saturated aqueous solution of common salt, dried over magnesium sulfate and concentrated in a vacuum. The obtained residue was purified through a silica gel column to obtain 1.12 g of the title compound as an oil (yield: 56%).

molecular formula: $C_{20}H_{25}NO_5$
$^1$H-NMR(CDCl$_3$)δ; 1.23(3H,t), 1.41~2.90(11H,m), 3.84(3H,S), 3.88(3H,S), 4.10(2H,g), 6.60(1H,S), 6.97(1H,S), 7.03(1H,S).

EXAMPLE 184

1-Benzyl-4-[(1,3-indanedion)-2-ylidenyl]methylpiperidine

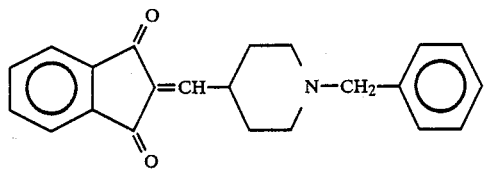

0.17 ml of diisopropylamine was added to 3 ml of anhydrous THF. 0.75 ml of a 1.6M solution of n-butyllithium in hexane was added to the obtained mixture at 0° C. The obtained mixture was stirred at 0° C. for 10 minutes and cooled to −78° C., followed by the addition of a solution of 0.18 g of 1,3-indanedione in 8 ml of anhydrous THF and 0.21 ml of hexamethylphosphoramide. The obtained mixture was stirred at −78° C. for 15 minutes, followed by the addition of a solution of 0.35 g of 1-benzyl-4-piperidinecarbaldehyde in 3 ml of anhydrous THF. The obtained mixture was gradually heated to a room temperature, stirred at that temperature overnight, diluted with methylene chloride, washed with a saturated aqueous solution of common salt, dried over magnesium sulfate and concentrated in a vacuum. The obtained residue was recrystallized from methylene chloride/IPE to obtain 0.12 g of the title compound (yield: 29%). The characteristics thereof are as follows:

m.p.(°C.): 1.73 to 174 (dec.),
elemental analysis as $C_{22}H_{21}NO_2$,

|  | C | H | N |
|---|---|---|---|
| calculated (%) | 79.73 | 6.39 | 4.23 |
| found (%) | 79.43 | 6.20 | 4.31 |

EXAMPLE 185

1-Benzyl-4-[(5,6-dimethoxyinden)-2-yl]methylpiperidine hydrochloride

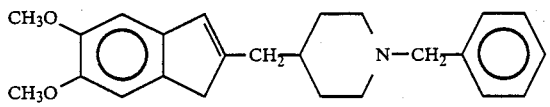

0.24 g of 1-benzyl-4-[(5,6-dimethoxy-1-indanol)-2-yl]methylpiperidine was dissolved in 5 ml of methylene chloride, followed by the addition of a 10% solution of hydrochloric acid in ethyl acetate. The obtained mixture was concentrated in a vacuum. The obtained residue was recrystallized from methylene chloride/IPE to obtain 0.24 g of the title compound (yield: 95%). The characteristics thereof are as follows:

m.p.(°C.): 216 to 217 (dec.),
elemental analysis as $C_{24}H_{29}NO_2,HCl$,

|  | C | H | N |
|---|---|---|---|
| calculated (%) | 72.07 | 7.56 | 3.50 |
| found (%) | 71.82 | 7.63 | 3.33 |

EXAMPLE 186

1-Benzyl-4-[3-[(5,6-dimethoxy-1-indanon)-2-ylidenyl]]propylpiperidine hydrochloride

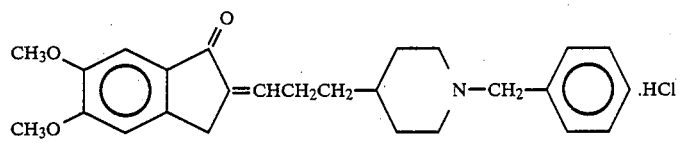

0.31 ml of diisopropylamine was added to 5 ml of anhydrous THF. 1.39 ml of a 1.6M solution of n-butyllithium in hexane was further added to the obtained mixture at 0° C. The obtained mixture was stirred at 0° C. for 10 minutes and cooled to −78° C., followed by the addition of a solution of 0.39 g of 5,6-dimethoxy-1-indanone in 5 ml of anhydrous THF and 0.35 ml of hexamethylphosphoramide. The obtained mixture was stirred at −78° C. for 15 minutes, followed by the addition of a solution of 0.50 g of 3-(1-benzyl-4-piperidine)propionaldehyde in 5 ml of anhydrous THF. The obtained mixture was gradually heated to a room temperature, stirred at that temperature for 3 ours, diluted with ethyl acetate, washed with a saturated aqueous solution of common salt, dried over magnesium sulfate and concentrated in a vacuum. The obtained residue was purified through a silica gel column and converted into its hydrochloride by an ordinary method of obtain 0.55 g of the title compound as an oil (yield: 61%).

molecular formula: $C_{26}H_{31}NO_3.HCl$,
$^1H$-NMR(CDCl$_3$)δ; 1.10~3.00(13H,m), 3.45(2H,S), 3,50(2H,S), 3.90(3H,S), 3.95(3H,S), 6.58~7.20 (3H,m), 7.27(5H,S).

EXAMPLE 187

1-Benzyl-4-[3-[(5,6-dimethoxy-1-indanon)-2-yl]]propylpiperidine hydrochloride

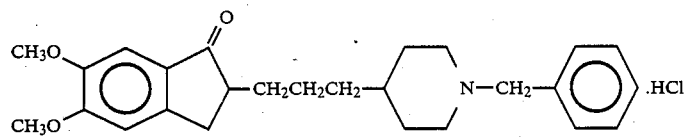

0.40 g of 1-benzyl-4-[3-[(5,6-dimethoxy-1-indanon)-2-ylidenyl]]propylpiperidine was dissolved in 15 ml of THF, followed by the addition of 0.1 g of 10% palladium/carbon. After the hydrogenation had been carried out at a room temperature under an ordinary pressure for 2 hours, the catalyst was filtered out and the filtrate was concentrated in a vacuum. The residue was purified through a silica gel column and converted into its hydrochloride by an ordinary method to obtain 0.37 g of the title compound as an oil (yield: 84%).

molecular formula $C_{26}H_{33}NO_3 \cdot HCl$,
$^1H$-NMR(CDCl$_3$)δ; 1.00~3.30(18H, m), 3.38, 3.43(total 2H, each S), 3.85(3H,S), 3.90(3H,S), 6.77, 6.83 (total 1H, each S), 7.05, 7.10 (total 1H, each S), 7.18, 7.20 (total 5H, each S).

EXAMPLES 188 to 249

The compounds listed in Table 9 were each synthesized and analyzed.

TABLE 9

| Example | Structural formula | Physicochemical constants (m.p., elemental analysis, NMR etc.) |
|---|---|---|
| 188 | [structure] | $^1H$—NMR(CDCl$_3$) δ; 1.00~3.40(14H,m), 3.47(2H, S), 3.78(3H,S), 6.90~7.50(3H,m), 7.23(5H,S). molecular formula: $C_{23}H_{27}NO_2 \cdot HCl$ |
| 189 | [structure] | $^1H$—NMR(CDCl$_3$) δ; 1.05~2.12(9H,m), 2.50~3.40(5H,m), 3.48(2H,S), 3.88(3H,S), 6.98(1H,q), 7.15~7.32(2H,m), 7.23(5H,S), molecular formula: $C_{23}H_{27}NO_2 \cdot HCl$ |
| 190 | [structure] | m.p. (°C.): 199 to 200 (dec.) elemental analysis as $C_{24}H_{29}NO_3 \cdot HCl$<br>　　　　　C　　H　　N<br>calculated (%)　69.30　7.27　3.37<br>found (%)　　　69.24　7.40　3.38 |
| 191 | [structure] | m.p. (°C.): 198 to 199 elemental analysis as $C_{24}H_{29}NO_3 \cdot HCl$<br>　　　　　C　　H　　N<br>calculated (%)　69.30　7.27　3.37<br>found (%)　　　69.15　7.42　3.47 |
| 192 | [structure] | m.p. (°C.): 200 to 201 elemental analysis as $C_{25}H_{31}NO_4 \cdot HCl$<br>　　　　　C　　H　　N<br>calculated (%)　67.33　7.23　3.14<br>found (%)　　　67.10　7.16　3.00 |
| 193 | [structure] | $^1H$—NMR(CDCl$_3$) δ; 1.05~2.15(9H,m), 2.55~3.43(5H,m), 3.48(2H,S), 7.23(5H,S), 7.23~7.43 (3H,m). molecular formula: $C_{22}H_{24}NOF \cdot HCl$ |
| 194 | [structure] | m.p. (°C.): 175 to 177 elemental analysis as $C_{23}H_{27}NO \cdot HCl$<br>　　　　　C　　H　　N<br>calculated (%)　74.68　7.63　3.79<br>found (%)　　　72.77　7.64　3.62<br>½H$_2$O (%)　　72.90　7.71　3.70 |

TABLE 9-continued

| Example | Structural formula | Physicochemical constants (m.p., elemental analysis, NMR etc.) |
|---|---|---|
| 195 | 2-[(1-benzylpiperidin-4-yl)methyl]-4-methyl-indan-1-one · HCl | m.p. (°C.): 211 to 213 (dec.)<br>elemental analysis as C₂₃H₂₇NO·HCl<br>　　　　　　C　　H　　N<br>calculated (%)　74.68　7.63　3.79<br>found (%)　　　72.68　7.49　3.70<br>½H₂O (%)　　　72.90　7.71　3.70 |
| 196 | 5-hydroxy-6-methoxy-2-[(1-benzylpiperidin-4-yl)methyl]indan-1-one | m.p. (°C.): 153 to 154<br>elemental analysis as C₂₃H₂₇NO₃<br>　　　　　　C　　H　　N<br>calculated (%)　75.59　7.45　3.83<br>found (%)　　　75.77　7.28　3.64 |
| 197 | 5-methoxy-6-hydroxy-2-[(1-benzylpiperidin-4-yl)methyl]indan-1-one | m.p. (°C.): 170 to 171 (dec.)<br>elemental analysis as C₂₃H₂₇NO₃<br>　　　　　　C　　H　　N<br>calculated (%)　75.59　7.45　3.83<br>found (%)　　　75.61　7.47　3.55 |
| 198 | 5,6-diethoxy-2-[(1-benzylpiperidin-4-yl)methyl]indan-1-one · HCl | m.p. (°C.): 175 to 176<br>elemental analysis as C₂₆H₃₃NO₃·HCl<br>　　　　　　C　　H　　N<br>calculated (%)　70.33　7.72　3.15<br>found (%)　　　70.20　7.46　3.35 |
| 199 | 5,6-methylenedioxy-2-[(1-benzylpiperidin-4-yl)methyl]indan-1-one · HCl | m.p. (°C.): 236 to 237 (dec.)<br>elemental analysis as C₂₃H₂₅NO₃·HCl<br>　　　　　　C　　H　　N<br>calculated (%)　69.08　6.55　3.50<br>found (%)　　　68.97　6.82　3.29 |
| 200 | 2-[(1-benzylpiperidin-4-yl)methyl]-3,4-dihydronaphthalen-1(2H)-one · HCl | m.p. (°C.): 195 to 196<br>elemental analysis as C₂₃H₂₇NO·HCl<br>　　　　　　C　　H　　N<br>calculated (%)　74.68　7.63　3.79<br>found (%)　　　74.72　7.77　3.78 |
| 201 | 2-[(1-benzylpiperidin-4-yl)methyl]benzosuberone · HCl | ¹H—NMR(CDCl₃) δ;<br>1.10~2.10(13H,m), 2.60~3.08(5H,m),<br>3.41(2H,S), 7.00~7.85(4H,m),<br>7.19(5H,S).<br>molecular formula: C₂₄H₂₉NO·HCl |
| 202 | 2-methyl-3-(1-benzylpiperidin-4-yl)-1-phenylpropan-1-one · HCl | ¹H—NMR(CDCl₃) δ;<br>1.17(3H,d), 1.12~2.10(9H,m),<br>2.60~2.93(2H,m), 3.41(2H,S),<br>3.51(1H,q), 7.20(5H,S), 7.30~7.92<br>(5H,m).<br>molecular formula: C₂₂H₂₇NO·HCl |
| 203 | 6-methoxy-5-isopropoxy-2-[(1-benzylpiperidin-4-yl)methyl]indan-1-one · HCl | m.p. (°C.): 126 to 127<br>elemental analysis as C₂₆H₃₃NO₃·HCl<br>　　　　　　C　　H　　N<br>calculated (%)　70.33　7.72　3.15<br>found (%)　　　70.41　7.48　2.85 |

TABLE 9-continued

| Example | Structural formula | Physicochemical constants (m.p., elemental analysis, NMR etc.) |
|---|---|---|
| 204 | 5,6-dimethoxy-2-[(CH$_2$)$_4$-(4-piperidyl)-N-benzyl]indan-1-one · HCl | $^1$H—NMR(CDCl$_3$) δ; 1.00~3.40(20H,m), 3.50(2H,S), 3.90(3H,S), 3.97(3H,S), 6.88(1H,S), 7.18(1H,S), 7.31(5H,S). molecular formula: C$_{27}$H$_{35}$NO$_3$·HCl |
| 205 | 5,6-dimethoxy-2-[(CH$_2$)$_5$-(4-piperidyl)-N-benzyl]indan-1-one · HCl | $^1$H—NMR(CDCl$_3$) δ; 1.05~3.36(22H,m), 3.45(2H,S), 3.85(3H,S), 3.90(3H,S), 6.78(1H,S), 7.08(1H,S), 7.21(5H,S). molecular formula: C$_{28}$H$_{37}$NO$_3$·HCl |
| 206 | 6-methoxy-2-[CH$_2$-(4-piperidyl)-N-benzyl]indan-1-one · HCl | $^1$H—NMR(CDCl$_3$) δ; 1.10~2.50(7H,m), 2.70~3.02(2H,m), 3.48(2H,S), 3.56(2H,S), 3.79(3H,S), 6.69(1H,dt), 7.02~7.50(3H,m), 7.21(5H,m). molecular formula: C$_{23}$H$_{25}$NO$_2$·HCl |
| 207 | 4-methoxy-2-[=CH-(4-piperidyl)-N-benzyl]indan-1-one · HCl | $^1$H—NMR(CDCl$_3$) δ; 1.50~3.57(11H,m), 3.48, 3.50(total 2H, each S), 3.83, 3.85(total 3H, each S), 6.57~7.39(4H,m), 7.22(5H,m). molecular formula: C$_{23}$H$_{25}$NO$_2$·HCl |
| 208 | 4,5-dimethoxy-2-[=CH-(4-piperidyl)-N-benzyl]indan-1-one · HCl | $^1$H—NMR(CDCl$_3$) δ; 1.58~2.55(7H,m), 2.79~3.02(2H,m), 3.50(2H,S), 3.63(2H,d), 3.90(6H,S), 6.63(1H,dt), 6.93(1H,d), 7.22(5H,S), 7.57(1H,d). molecular formula: C$_{24}$H$_{27}$NO$_3$·HCl |
| 209 | 6,7-dimethoxy-2-[=CH-(4-piperidyl)-N-benzyl]indan-1-one · HCl | $^1$H—NMR(CDCl$_3$) δ; 1.50~2.55(7H,m), 2.78~3.03(2H,m), 3.48(2H,S), 3.56(2H,d), 3.85(3H,S), 4.00(3H,S), 6.62(1H,dt), 7.07(1H,d), 7.21(1H,d), 7.22(5H,S). molecular formula: C$_{24}$H$_{27}$NO$_3$·HCl |
| 210 | 4,5,7-trimethoxy-2-[=CH-(4-piperidyl)-N-benzyl]indan-1-one · HCl | $^1$H—NMR(CDCl$_3$) δ; 1.50~2.50(7H,m), 2.78~3.03(2H,m), 3.48(2H,S), 3.53(2H,d), 3.82(3H,S), 3.90(3H,S), 4.03(3H,S), 6.58(1H,dt), 6.61(1H,S), 7.25(5H,S). molecular formula: C$_{25}$H$_{29}$NO$_4$·HCl |
| 211 | 6-fluoro-2-[=CH-(4-piperidyl)-N-benzyl]indan-1-one · HCl | $^1$H—NMR(CDCl$_3$) δ; 1.52~2.55(7H,m), 2.78~3.02(2H,m), 3.50(2H,S), 3.59(2H,S), 6.72(1H,dt), 7.05~7.55(3H,m), 7.22(5H,S). molecular formula: C$_{22}$H$_{22}$NOF·HCl |

TABLE 9-continued

| Example | Structural formula | Physicochemical constants (m.p., elemental analysis, NMR etc.) |
|---|---|---|
| 212 | 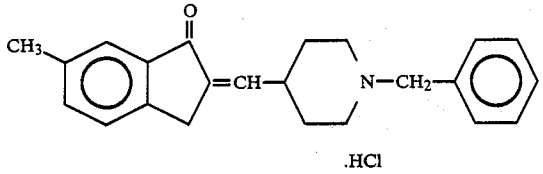 .HCl | $^1$H—NMR(CDCl$_3$) δ; 1.50~2.55(7H,m), 2.38(3H,S), 2.78~3.02(2H,m), 3.48(2H,S), 3.57(2H,S), 6.66(1H,dt), 7.38~7.60 (3H,m), 7.21(5H,S). molecular formula: C$_{23}$H$_{25}$NO.HCl |
| 213 | 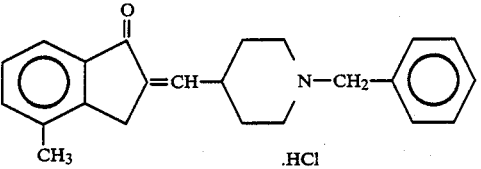 .HCl | $^1$H—NMR(CDCl$_3$) δ; 1.48~2.60(7H,m), 2.32(3H,S), 2.77~3.02(2H,m), 3.49(4H,S), 6.69(1H,dt), 7.10~7.67(3H,m), 7.22(5H,S). molecular formula: C$_{23}$H$_{25}$NO.HCl |
| 214 | 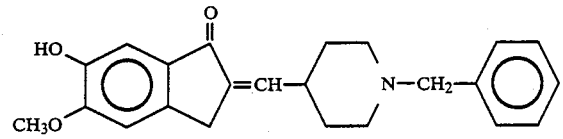 | m.p. (°C.): 174 to 175 elemental analysis as C$_{23}$H$_{25}$NO$_3$<br>　　　　　　C　　H　　N<br>calculated (%)　69.08　6.55　3.50<br>found (%)　　　69.12　6.41　3.43 |
| 215 | 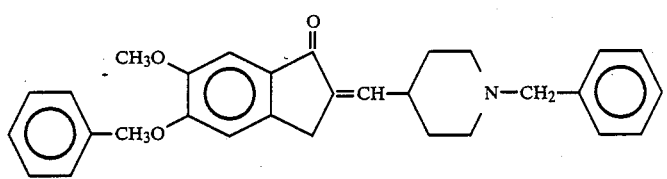 | m.p. (°C.): 175 to 176 elemental analysis as C$_{30}$H$_{31}$NO$_3$<br>　　　　　　C　　H　　N<br>calculated (%)　79.44　6.89　3.09<br>found (%)　　　79.04　6.87　2.77 |
| 216 | 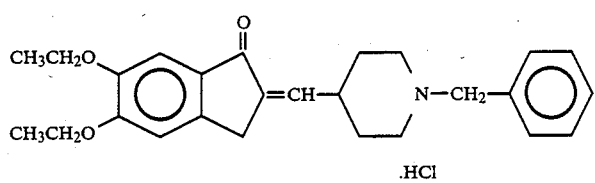 .HCl | m.p. (°C.): 180 to 181 elemental analysis as C$_{26}$H$_{31}$NO$_3$.HCl<br>　　　　　　C　　H　　N<br>calculated (%)　70.65　7.30　3.17<br>found (%)　　　70.34　7.05　3.07 |
| 217 | 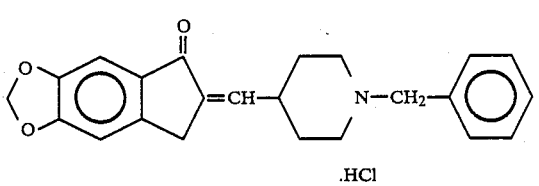 .HCl | m.p. (°C.): 228 to 230 (dec.) elemental analysis as C$_{23}$H$_{23}$NO$_3$.HCl<br>　　　　　　C　　H　　N<br>calculated (%)　69.43　6.08　3.52<br>found (%)　　　67.89　5.97　3.45<br>½H$_2$O (%)　　67.89　6.19　3.44 |
| 218 | 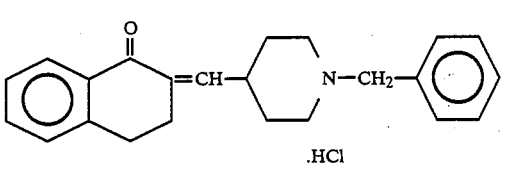 .HCl | $^1$H—NMR(CDCl$_3$) δ; 2.48~3.02(13H,m), 3.48(2H,S), 6.73(1H,dt), 7.10~8.10(4H,m), 7.22(5H,S). molecular formula: C$_{23}$H$_{25}$NO.HCl |
| 219 | 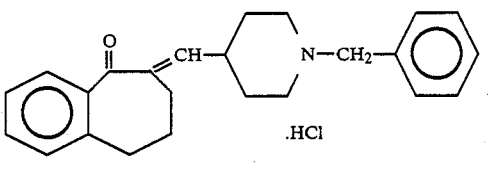 .HCl | m.p. (°C.): 211 to 213 (dec.) elemental analysis as C$_{24}$H$_{27}$NO.HCl<br>　　　　　　C　　H　　N<br>calculated (%)　75.47　7.39　3.67<br>found (%)　　　75.22　7.41　3.57 |
| 220 | 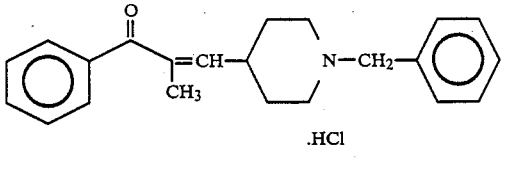 .HCl | $^1$H—NMR(CDCl$_3$) δ; 1.20~2.60(7H,m), 1.96(3H,d), 2.70~2.97(2H,m), 3.46(3H,S), 6.67(1H,dd), 7.21(5H,S), 7.21~7.61(5H,m). molecular formula: C$_{22}$H$_{25}$NO.HCl |

TABLE 9-continued

| Example | Structural formula | Physicochemical constants (m.p., elemental analysis, NMR etc.) |
|---|---|---|
| 221 | (CH3O, (CH3)2CHO-substituted indanone)=CH—(4-piperidinyl)—N—CH2—Ph | m.p. (°C.): 170 to 171<br>elemental analysis as C26H31NO3<br>　　　　C　　H　　N<br>calculated (%)　77.01　7.70　3.45<br>found (%)　　　77.10　7.67　3.43 |
| 222 | (5,6-dimethoxyindanone)=CHCH2CH2—(4-piperidinyl)—N—CH2—Ph ·HCl | $^1$H—NMR(CDCl$_3$) δ;<br>1.10~2.40(13H,m), 2.70~3.00(2H,m),<br>3.45(2H,S), 3.48(2H,S), 3.86(3H,S),<br>3.91(3H,S), 6.68(1H,tt), 6.80(1H,S),<br>7.20(6H,S).<br>molecular formula: C27H33NO3·HCl |
| 223 | (5,6-dimethoxyindanone)=CHCH2CH2CH2CH2—(4-piperidinyl)—N—CH2—Ph ·HCl | $^1$H—NMR(CDCl$_3$) δ;<br>1.10~2.40(15H,m), 2.68~3.00(2H,m),<br>3.46(2H,S), 3.50(2H,S), 3.88(3H,S),<br>3.93(3H,S), 6.68(1H,tt), 6.83(1H,S),<br>7.19(1H,S), 7.21(5H,S).<br>molecular formula: C28H35NO3·HCl |
| 224 | (5,6-dimethoxyindanone)=CH—CH=CH—(4-piperidinyl)—N—CH2—Ph ·HCl | m.p. (°C.): 130 to 135<br>elemental analysis as C26H29NO3·HCl<br>　　　　C　　H　　N<br>calculated (%)　70.98　6.87　3.18<br>found (%)　　　70.81　6.72　3.10 |
| 225 | (5,6-dimethoxyindanone)—CH2—N(4-benzyl-piperidinyl) ·HCl | $^1$H—NMR(CDCl$_3$) δ;<br>1.10~3.50(16H,m), 3.87(3H,S),<br>3.93(3H,S), 6.80(1H,S), 7.00~7.25<br>(6H,m).<br>molecular formula: C24H29NO3·HCl |
| 226 | (5,6-dimethoxyindanone)—CH2—(4-piperidinyl)—N(→O)—CH2—Ph | m.p. (°C.): 186 to 188 (dec.)<br>$^1$H—NMR(CDCl$_3$) δ; 1.65~2.10(7H,m),<br>2.65~2.75(2H,m), 3.25~3.83(5H,m),<br>3.92(3H,S), 3.98(3H,S), 4.60(2H,S),<br>6.88(1H,S), 7.19(1H,S), 7.26~<br>7.60(5H,m).<br>molecular formula: C24H29NO4 |
| 227 | (5,6-dimethoxyindanone)—CH2—(4-piperidinyl)—N—CH2—(2-methylphenyl) ·HCl | m.p. (°C.): 220 to 221<br>elemental analysis as C25H31NO3·HCl<br>　　　　C　　H　　N<br>calculated (%)　69.83　7.50　3.26<br>found (%)　　　70.03　7.51　3.26 |
| 228 | (5,6-dimethoxyindanone)—CH2—(4-piperidinyl)—N—CH2—(3-methylphenyl) ·HCl | m.p. (°C.): 212 to 213<br>elemental analysis as C25H31NO3·HCl<br>　　　　C　　H　　N<br>calculated (%)　69.83　7.50　3.26<br>found (%)　　　69.62　7.38　3.15 |

TABLE 9-continued

| Example | Structural formula | Physicochemical constants (m.p., elemental analysis, NMR etc.) |
|---|---|---|
| 229 | (structure) · HCl | m.p. (°C.): 229 to 230 (dec.)<br>elemental analysis as C₂₅H₃₁NO₃·HCl<br>　　　　　C　　H　　N<br>calculated (%)　69.83　7.50　3.26<br>found (%)　　　69.91　7.48　3.28 |
| 230 | (structure) · HCl | ¹H—NMR(CDCl₃) δ;<br>1.00~3.50(14H,m), 3.73(2H,S),<br>3.86(3H,S), 3.93(3H,S), 6.82(1H,S),<br>7.12(1H,S), 7.22~7.80(4H,m),<br>molecular formula: C₂₄H₂₈N₂O₅·HCl |
| 231 | (structure) · HCl | m.p. (°C.): 210 to 211<br>elemental analysis as C₂₄H₂₈N₂O₅·HCl<br>　　　　　C　　H　　N<br>calculated (%)　62.54　6.34　6.08<br>found (%)　　　62.48　6.34　5.96 |
| 232 | (structure) · HCl | m.p. (°C.): 234 to 236 (dec.)<br>elemental analysis as C₂₄H₂₈N₂O₅·HCl<br>　　　　　C　　H　　N<br>calculated (%)　62.54　6.34　6.08<br>found (%)　　　62.56　6.25　5.83 |
| 233 | (structure) · HCl | ¹H—NMR(CDCl₃) δ;<br>1.10~3.43(14H,m), 3.52(2H,S),<br>3.84(3H,S), 3.91(3H,S), 6.35~7.08<br>(7H,m).<br>molecular formula: C₂₄H₂₉NO₄·HCl |
| 234 | (structure) · HCl | m.p. (°C.): 146 to 148<br>elemental analysis as C₂₄H₂₉NO₄·HCl<br>　　　　　C　　H　　N<br>calculated (%)　66.51　7.29　3.53<br>found (%)　　　66.73　7.00　3.24 |
| 235 | (structure) · HCl | m.p. (°C.): 193 to 194<br>elemental analysis as C₂₅H₃₁NO₄·HCl<br>　　　　　C　　H　　N<br>calculated (%)　67.33　7.23　3.14<br>found (%)　　　67.43　7.22　3.13 |
| 236 | (structure) · HCl | m.p. (°C.): 226 to 228 (dec.)<br>elemental analysis as C₂₅H₃₁NO₄·HCl<br>　　　　　C　　H　　N<br>calculated (%)　67.33　7.23　3.14<br>found (%)　　　67.21　7.29　2.97 |

TABLE 9-continued

| Example | Structural formula | Physicochemical constants (m.p., elemental analysis, NMR etc.) |
|---|---|---|
| 237 | [Structure: 5,6-dimethoxy-indanone-CH₂-piperidine-N-CH₂-phenyl-OCH₂-phenyl] · HCl | $^1$H—NMR(CDCl$_3$) δ; 0.78~3.40(14H,m), 3.46(2H,S), 3.85(3H,S), 3.91(3H,S), 5.01(2H,S), 6.78(1H,S), 6.80~7.43(9H,m), 7.09(1H,S). molecular formula: C$_{31}$H$_{35}$NO$_4$·HCl |
| 238 | [Structure: 5,6-dimethoxy-indanone-CH₂-piperidine-N-CH₂-pyridyl] · 2HCl | m.p. (°C.): 224 to 226 (dec.) elemental analysis as C$_{23}$H$_{28}$N$_2$O$_3$·2HCl<br>　　　　　　C　　H　　N<br>calculated (%)　60.93　6.67　6.18<br>found (%)　　　58.72　6.98　5.56<br>H$_2$O (%)　　　58.60　6.84　5.94 |
| 239 | [Structure: 5,6-dimethoxy-indanone-CH₂-piperidine-N-CH₂CH₂-phenyl] · HCl | m.p. (°C.): 253 to 256 (dec.) elemental analysis as C$_{25}$H$_{31}$NO$_3$·HCl<br>　　　　　　C　　H　　N<br>calculated (%)　69.83　7.50　3.26<br>found (%)　　　69.60　7.49　3.27 |
| 240 | [Structure: 5,6-dimethoxy-indanone-CH₂-piperidine-N-CH₂-cyclohexyl] · HCl | m.p. (°C.): 225 to 226 (dec.) elemental analysis as C$_{24}$H$_{35}$NO$_3$·HCl<br>　　　　　　C　　H　　O<br>calculated (%)　68.31　8.60　3.32<br>found (%)　　　68.17　8.49　3.51 |
| 241 | [Structure: 5,6-dimethoxy-indanone-CH₂-piperidine-N-CH₂-naphthyl] · HCl | m.p. (°C.): 226 to 227 (dec.) elemental analysis as C$_{28}$H$_{31}$NO$_3$·HCl<br>　　　　　　C　　H　　N<br>calculated (%)　72.17　6.92　3.01<br>found (%)　　　71.71　7.07　2.85 |
| 242 | [Structure: 5,6-dimethoxy-indanone-CH₂-piperidine-N-CH₂-naphthyl] · HCl | m.p. (°C.): 243 to 245 (dec.) elemental analysis as C$_{28}$H$_{31}$NO$_3$·HCl<br>　　　　　　C　　H　　N<br>calculated (%)　72.17　6.92　3.01<br>found (%)　　　71.75　6.92　3.01 |
| 243 | [Structure: 5,6-dimethoxy-indanone-CH₂-piperidine-N-CH₂-(3,4-dimethoxyphenyl)] · HCl | m.p. (°C.): 191 to 192 elemental analysis as C$_{26}$H$_{33}$NO$_5$·HCl<br>　　　　　　C　　H　　N<br>calculated (%)　65.60　7.20　2.94<br>found (%)　　　65.34　7.27　2.79 |
| 244 | [Structure: 5,6-dimethoxy-indanone-CH₂-piperidine-N-CH₂-(3,4,5-trimethoxyphenyl)] · HCl | m.p. (°C.): 219 to 221 elemental analysis as C$_{27}$H$_{35}$NO$_6$·HCl<br>　　　　　　C　　H　　N<br>calculated (%)　64.09　7.17　2.77<br>found (%)　　　63.27　7.19　2.51<br>½H$_2$O (%)　　62.96　7.24　2.72 |

TABLE 9-continued

| Example | Structural formula | Physicochemical constants (m.p., elemental analysis, NMR etc.) |
|---|---|---|
| 245 | [Structure: 5-hydroxy-6-methoxy-indanone with CH2-piperidine-NH.HCl] | $^1$H—NMR(D$_2$O) δ; 1.10~3.12(14H,m), 3.84(3H,S), 6.70(1H,S), 6.84(1H,S). molecular formula: C$_{16}$H$_{21}$NO$_3$.HCl |
| 246 | [Structure: 5,6-dimethoxyindanone-2,4-dinitrophenylhydrazone with CH2-piperidine-N-CH2-phenyl] | m.p. (°C.): 182 to 183 elemental analysis as C$_{30}$H$_{33}$N$_5$O$_6$<br>     C    H    N<br>calculated (%) 64.39  5.94  12.51<br>found (%)     64.42  5.78  12.52 |
| 247 | [Structure: 5,6-dimethoxyindane dithiolane with CH2-piperidine-N-CH2-phenyl .HCl] | m.p. (°C.): 240 to 241 (dec.) elemental analysis as C$_{26}$H$_{33}$NO$_2$S$_2$.HCl<br>     C    H    N<br>calculated (%) 63.46  6.96  2.85<br>found (%)     63.18  6.78  2.80 |
| 248 | [Structure: 5,6-dimethoxyindanone-2-NH-piperidine-N-CH2-phenyl .2HCl] | m.p. (°C.): 180 to 185 (dec.) elemental analysis as C$_{23}$H$_{28}$N$_2$O$_3$.2HCl<br>     C    H    N<br>calculated (%) 60.73  6.45  6.25<br>found (%)     60.92  6.67  6.18 |
| 249 | [Structure: bis(5,6-dimethoxyindanonyl)-CH-piperidine-N-CH2-phenyl .HCl] | m.p. (°C.): 230 to 232 (dec.) elemental analysis as C$_{35}$H$_{39}$NO$_6$.HCl<br>     C    H    N<br>calculated (%) 69.35  6.65  2.31<br>found (%)     69.21  6.59  2.33 |

The compounds obtained in Examples 178 to 249 were each examined according to the above shown experimental test in view of the inhibitory activity. Results are shown in Table 10.

TABLE 10

Inhibitory effect against acetylcholinesterase in vitro

| Compound | Inhibitory activity on AChE IC$_{50}$ (μM) | Compound | Inhibitory activity on AChE IC$_{50}$ (μM) | Compound | Inhibitory activity on AChE IC$_{50}$ (μM) |
|---|---|---|---|---|---|
| 178 | >10 | 202 | 1.2 | 226 | 0.0049 |
| 179 | 5.4 | 203 | 0.009 | 227 | 0.01 |
| 180 | 0.001 | 204 | 0.035 | 228 | 0.002 |
| 181 | 0.094 | 205 | 0.014 | 229 | 0.04 |
| 182 | 0.8 | 206 | 0.41 | 230 | 0.16 |
| 183 | 5.3 | 207 | 0.049 | 231 | 0.004 |
| 184 | >5 | 208 | 0.062 | 232 | 0.1 |
| 185 | 0.00082 | 209 | 0.43 | 233 | 0.046 |
| 186 | 0.0015 | 210 | 0.06 | 234 | 0.0018 |
| 187 | 4.4 | 211 | 2 | 235 | 0.22 |
| 188 | 0.081 | 212 | 0.5 | 236 | 3.6 |
| 189 | 0.012 | 213 | 0.05 | 237 | 2.6 |
| 190 | 0.02 | 214 | 0.0084 | 238 | 0.072 |
| 191 | 0.085 | 215 | 0.0042 | 239 | 0.18 |
| 192 | 0.013 | 216 | 0.017 | 240 | 0.0089 |
| 193 | 0.2 | 217 | 0.14 | 241 | 0.22 |
| 194 | 0.069 | 218 | 20 | 242 | 2.9 |
| 195 | 0.0071 | 219 | 19 | 243 | 4 |
| 196 | 0.0013 | 220 | 11 | 244 | 4.9 |
| 197 | 0.38 | 221 | 0.033 | 245 | 5 |
| 198 | 0.0054 | 222 | 0.011 | 246 | 4.4 |
| 199 | 0.023 | 223 | 0.0054 | 247 | — |
| 200 | 2.1 | 224 | 0.003 | 248 | 1.4 |
| 201 | 15 | 225 | 0.48 | 249 | 0.62 |

We claim:

1. A cyclic amine compound having the formula

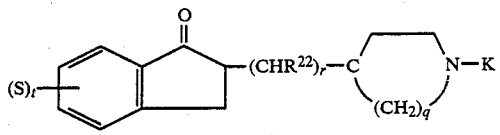

wherein
- r is an integer of 1 to 10, $R^{22}$ is hydrogen or methyl, and the $R^{22}$ radicals can be the same or different when r is from 2 to 10;
- K is phenylalkyl or phenylalkyl having a substituent on the phenyl ring;
- S is hydrogen or a substituent on the phenyl ring, and t is an integer of 1 to 4, with the proviso that $(S)_t$ can be a methylenedioxy group or an ethylenedioxy group joined to two adjacent carbon atoms of the phenyl ring; and
- q is an integer of 1 to 3, or a pharmacologically acceptable salt thereof.

2. A cyclic amine compound as claimed in claim 1 in which q is 2.

3. A cyclic amine compound as claimed in claim 1 in which K is benzyl, m-nitrobenzyl or m-fluorobenzyl.

4. A cyclic amine compound as claimed in claim 2 in which K is benzyl.

5. A cyclic amine compound as claimed in claim 1 in which S is lower alkyl having 1 to 6 carbon atoms or lower alkoxy having 1 to 6 carbon atoms.

6. A cyclic amine compound as claimed in claim 1 in which S is methoxy and t is an integer of from 1 to 3.

7. A cyclic amine compound as claimed in claim 1 in which r is an integer of 1 to 3.

8. A cyclic amine compound as claimed in claim 1, or a pharmacologically acceptable salt thereof, which is 1-benzyl-4-((5,6-dimethoxy-1-indanon)-2-yl)methylpiperidine.

9. A cyclic amine compound as claimed in claim 1, or a pharmacologically acceptable salt thereof, which is selected from the group consisting of:
1-benzyl-4-((5-methoxy-1-indanon)-2-yl)methylpiperidine,
1-benzyl-4-((5,6-diethoxy-1-indanon)-2-yl)methylpiperidine,
1-benzyl-4-((5,6-methylenedioxy-1-indanon)-2-yl)methylpiperidine,
1-(m-nitrobenzyl)-4-((5,6-dimethoxy-1-indanon)-2-yl)methylpiperidine,
1-(m-fluorobenzyl)-4-((5,6-dimethoxy-1-indanon)-2-yl)methylpiperidine,
1-benzyl-4-((5,6-dimethoxy-1-indanon)-2-yl)propylpiperidine and
1-benzyl-4-((5-isopropoxy-6-methoxy-1-indanon)-2-yl)methylpiperidine.

10. A therapeutic composition for treatment of a disease caused by acetylcholinesterase activity which comprises a pharmacologically effective amount of the cyclic amine compound as defined in claim 1 or a pharmacologically acceptable salt thereof, and pharmacologically acceptable carrier.

11. A method for treating a disease caused by acetylcholinesterase activity which comprises administering to a human patient having the disease, an effective amount of the cyclic amine compound as defined in claim 1, or a pharmacologically acceptable salt thereof.

12. A method as claimed in claim 11, in which the disease is the senile dementia.

13. A method as claimed in claim 11, in which the disease is senile dementia of the Alzheimer type.

* * * * *

UNITED STATES PATENT AND TRADEMARK OFFICE

CERTIFICATE EXTENDING PATENT TERM
UNDER 35 U.S.C. § 156

PATENT NO.      :   4,895,841

ISSUED          :   January 23, 1990

INVENTOR(S)     :   Hachiro Sugimoto et al.

PATENT OWNER    :   Eisai Co., Ltd.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 888 days from June 20, 2008, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 2nd day of September 1998.

Bruce A. Lehman
Assistant Secretary of Commerce and
  Commissioner of Patents and Trademarks